United States Patent
Lee et al.

(10) Patent No.: US 8,921,832 B2
(45) Date of Patent: Dec. 30, 2014

(54) COMPOUND AND ORGANIC DEVICE USING SAME

(75) Inventors: Dae-Woong Lee, Daejeon (KR);
Sung-Kil Hong, Daejeon (KR);
Tae-Yoon Park, Daejeon (KR);
Yeon-Hwan Kim, Seoul (KR);
Seong-So Kim, Paju-si (KR)

(73) Assignee: LG Chem, Ltd., Seoul (KR)

( * ) Notice: Subject to any disclaimer, the term of this patent is extended or adjusted under 35 U.S.C. 154(b) by 831 days.

(21) Appl. No.: 13/123,162

(22) PCT Filed: Oct. 8, 2009

(86) PCT No.: PCT/KR2009/005736
§ 371 (c)(1),
(2), (4) Date: Apr. 7, 2011

(87) PCT Pub. No.: WO2010/041872
PCT Pub. Date: Apr. 15, 2010

(65) Prior Publication Data
US 2011/0193074 A1  Aug. 11, 2011

(30) Foreign Application Priority Data
Oct. 8, 2008  (KR) .......................... 10-2008-0098493

(51) Int. Cl.
*H01L 51/54*  (2006.01)
*C07D 209/82*  (2006.01)
*H01L 51/00*  (2006.01)
*H01L 51/50*  (2006.01)

(52) U.S. Cl.
CPC ........... *C07D 209/82* (2013.01); *H01L 51/5012* (2013.01); *Y02E 10/549* (2013.01); *H01L 51/0072* (2013.01); *H01L 51/5048* (2013.01); *H01L 51/006* (2013.01); *H01L 51/0058* (2013.01); *H01L 51/5088* (2013.01)

USPC .............. 257/40; 257/E51.018; 257/E51.024; 548/442; 548/406; 548/159; 548/224; 546/276.7; 546/256

(58) Field of Classification Search
USPC ............. 257/40, E51.018, E51.024; 548/442, 548/406, 159, 224; 546/276.7, 256
See application file for complete search history.

(56) References Cited

U.S. PATENT DOCUMENTS

| 7,737,627 B2 | 6/2010 | Hwang et al. |
| 2005/0221124 A1 | 10/2005 | Hwang et al. |
| 2008/0106188 A1 | 5/2008 | Hwang et al. |

(Continued)

FOREIGN PATENT DOCUMENTS

| CN | 1702065 A | 11/2005 |
| EP | 1 985 613 A2 | 10/2008 |
| JP | 2008179614 A | 8/2008 |
| KR | 10-0573137 B1 | 4/2006 |
| KR | 10-0822212 B1 | 4/2008 |

(Continued)

OTHER PUBLICATIONS

Shen J Y et al: "High Tg blue emitting materials for electroluminescent devices", Journal of Materials Chemistry, The Royal Society of Chemistry, Cambridge, GB, vol. 15, No. 25, May 12, 2005, pp. 2455-2463, XP003011710, ISSN: 0959-9428, DOI: 10.1039/B501819F figure 1; compounds 4,5*.
Journal of Materials Chemistry, 2005, vol. 15, pp. 2455-2463.

*Primary Examiner* — Long Pham
(74) *Attorney, Agent, or Firm* — McKenna, Long & Aldridge LLP

(57) ABSTRACT

The present invention relates to a novel compound and an organic light emitting device using the compound, and the compound according to the present invention may largely improve a life span, efficiency, electrochemical stability and thermal stability of the organic light emitting device.

16 Claims, 1 Drawing Sheet

(56) References Cited

U.S. PATENT DOCUMENTS

2008/0169755 A1 7/2008 Kim et al.
2008/0171227 A1 7/2008 Kwak et al.
2009/0004506 A1 1/2009 Nomura et al.

FOREIGN PATENT DOCUMENTS

| KR | 10-0846590 B1 | 5/2008 |
| KR | 10-2008-0067165 A | 7/2008 |
| WO | WO 2009/035295 A2 | 3/2009 |
| WO | WO 2009/035296 A2 | 3/2009 |

COMPOUND AND ORGANIC DEVICE USING SAME

TECHNICAL FIELD

This application is a national stage application of PCT/KR2009/005736, filed Oct. 8, 2009, which claims the priority to Korean Patent Application No. KR-10-2008-0098493, filed on Oct. 8, 2008, all of which are hereby incorporated by reference in their entirety. The present invention relates to a novel compound that is capable of largely improving a life span, efficiency, electrochemical stability, and thermal stability of an organic light emitting device, and an organic electronic device in which the compound is comprised in an organic compound layer.

BACKGROUND ART

An organic light emission phenomenon is an example of a conversion of current into visible rays through an internal process of a specific organic molecule. The organic light emission phenomenon is based on the following mechanism. When an organic material layer is disposed between an anode and a cathode, if voltage is applied between two electrodes, electrons and holes are injected from the cathode and the anode to the organic material layer. The electrons and the holes which are injected into the organic material layer are recombined to form an exciton, and the exciton is reduced to a bottom state to emit light. The organic light emitting device using the principle may be generally constituted by a cathode, an anode, and an organic material layer that is interposed therebetween, for example, an organic material layer that comprises a hole injection layer, a hole transport layer, a light emitting layer, and an electron transport layer.

The materials used in the organic light emitting device are mostly pure organic materials or complexes of organic material and metal. The material used in the organic light emitting device may be classified as a hole injection material, a hole transport material, a light emitting material, an electron transport material, or an electron injection material, according to its use. In connection with this, an organic material having a p-type property, which is easily oxidized and is electrochemical stable when it is oxidized, is mostly used as the hole injection material or the hole transport material. Meanwhile, an organic material having an n-type property, which is easily reduced and is electrochemical stable when it is reduced, is used as the electron injection material or the electron transport material. As the light emitting layer material, an organic material having both p-type and n-type properties is preferable, which is stable when it is oxidized and when it is reduced. Also a material having high light emission efficiency for conversion of the exciton into light when the exciton is formed is preferable.

In addition, it is preferable that the material used in the organic light emitting device further have the following properties.

First, it is preferable that the material used in the organic light emitting device have excellent thermal stability. The reason is that joule heat is generated by movement of electric charges in the organic light emitting device. NPB, which has recently been used as the hole transport layer material, has a glass transition temperature of 100° C. or lower, thus it is difficult to apply to an organic light emitting device requiring a high current.

Second, in order to produce an organic light emitting device that is capable of being actuated at low voltage and has high efficiency, holes and electrons which are injected into the organic light emitting device must be smoothly transported to a light emitting layer, and must not be released out of the light emitting layer. To achieve this, a material used in the organic light emitting device must have a proper band gap and a proper HOMO or LUMO energy levels. A LUMO energy level of PEDOT:PSS, which is currently used as a hole transport material of an organic light emitting device produced using a solution coating method, is lower than that of an organic material used as a light emitting layer material, thus it is difficult to produce an organic light emitting device having high efficiency and a long lifespan.

Moreover, the material used in the organic light emitting device must have excellent chemical stability, electric charge mobility, and interfacial characteristic with an electrode or an adjacent layer. That is to say, the material used in the organic light emitting device must be little deformed by moisture or oxygen. Furthermore, proper hole or electron mobility must be assured so as to balance densities of the holes and of the electrons in the light emitting layer of the organic light emitting device to maximize the formation of excitons. Additionally, it has to be able to have a good interface with an electrode comprising metal or metal oxides so as to assure stability of the device.

Accordingly, there is a need to develop an organic material having the above-mentioned requirements in the art.

DISCLOSURE

Technical Problem

The present invention has been made to solve the problems in the related art, and it is an object of the present invention to provide a heterocompound derivative that can satisfy conditions required in a material capable of being used in an organic light emitting device, for example, an appropriate energy level, electrochemical stability and thermal stability, and has a chemical structure that is capable of performing various functions required in the organic light emitting device according to a substituent group, and an organic light emitting device comprising the same.

Technical Solution

In order to accomplish the above object, an aspect of the present invention provides a compound that is represented by the following Formula 1.

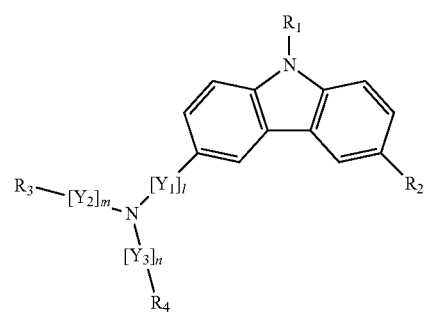

[Formula 1]

wherein l, m and n are each independently an integer in the range of 0 to 5, $Y_1$ to $Y_3$ are each independently selected from the group consisting of $C_{2-40}$ alkenylene group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{6-40}$ arylene group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{4-40}$ divalent hetero ring group that is unsubstituted or substituted by one or more substituent groups selected from the group consisting of halogen group, alkyl group, alkenyl group, alkoxy group, substituted or unsubstituted arylamine group, substituted or unsubstituted aryl group, substituted or unsubstituted arylalkyl group, substituted or unsubstituted arylalkenyl group, substituted or unsubstituted hetero ring group, nitrile group and acetylene group and has O, N or S as a heteroatom; divalent amine group that is substituted by one or more substituent groups selected from the group consisting of alkyl group, alkenyl group, substituted or unsubstituted aryl group, substituted or unsubstituted arylalkyl group, substituted or unsubstituted arylalkenyl group; fluorenylene group that is unsubstituted or substituted by one or more substituent groups selected from the group consisting of alkyl group, alkenyl group, substituted or unsubstituted aryl group, substituted or unsubstituted arylalkyl group, substituted or unsubstituted arylalkenyl group; amide group; ester group; silane group and germanium group, $R_1$, $R_3$ and $R_4$ are each independently selected from the group consisting of $C_{1-40}$ alkyl group that is unsubstituted or substituted by one or more substituent groups selected from the group consisting of alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{1-40}$ alkoxy group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{2-40}$ alkenyl group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{6-40}$ aryl group that is unsubstituted or substituted by one or more substituent groups selected from the group consisting of halogen group, alkyl group, alkenyl group, alkoxy group, substituted or unsubstituted arylamine group, substituted or unsubstituted aryl group, substituted or unsubstituted arylalkyl group, substituted or unsubstituted arylalkenyl group, substituted or unsubstituted hetero ring group, nitrile group and acetylene group; $C_{4-40}$ hetero ring group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group and has O, N or S as a heteroatom; amine group that is unsubstituted or substituted by one or more substituent groups selected from the group consisting of alkyl group, alkenyl group, substituted or unsubstituted aryl group, substituted or unsubstituted arylalkyl group, substituted or unsubstituted arylalkenyl group; fluorenyl group that is substituted by one or more substituent groups selected from the group consisting of alkyl group, alkenyl group, substituted or unsubstituted aryl group, substituted or unsubstituted arylalkyl group, substituted or unsubstituted arylalkenyl group; bisspirofluorenyl group; nitrile group; cyano group; nitro group; amide group; ester group; silane group and germanium group, $R_2$ is selected from the group consisting of $C_{1-40}$ alkyl group that is unsubstituted or substituted by one or more substituent groups selected from the group consisting of alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{1-40}$ alkoxy group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted, hetero ring group, nitrile group and acetylene group; $C_{6-40}$ aryl group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{4-40}$ hetero ring group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group and has O, N or S as a heteroatom; fluorenyl group that is substituted by one or more substituent groups selected from the group consisting of alkyl group, alkenyl group, substituted or unsubstituted aryl group, substituted or unsubstituted arylalkyl group, and substituted or unsubstituted arylalkenyl group; bisspirofluorenyl group; nitrile group; cyano group; nitro group; ester group; silane group; germanium group and halogen group, at least one of $R_3$ or $R_4$ comprises the structure of the following Formula 2,

[Formula 2]

wherein $R_5$ to $R_7$ are each independently selected from the group consisting of hydrogen; halogen group; $C_{1-40}$ alkyl group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{1-40}$ alkoxy group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{2-40}$ alkenyl group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{6-40}$ aryl group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{4-40}$ hetero ring group that is unsubstituted or substituted by one or more substituent groups selected from the group consisting of halogen group, alkyl group, alkenyl group, alkoxy group, substituted or unsubstituted arylamine group, substituted or unsubstituted aryl group, substituted or unsubstituted arylalkyl group, substituted or unsubstituted arylalkenyl group, substituted or unsubstituted hetero ring group, nitrile group and acetylene group and has O, N or S as a heteroatom; amine group that is substituted by one or more substituent groups selected from the group consisting of alkyl group, alkenyl group, substituted or unsubstituted aryl group, substituted or unsubstituted arylalkyl group, substituted or unsubstituted arylalkenyl group; nitrile group; nitro group; amide group; ester group; silane group and germanium group, and they may form an aliphatic or hetero condensation ring in conjunction with adjacent groups.

In order to accomplish the above object, another aspect of the present invention provides an organic electronic device in which the compound is comprised in an organic material layer.

Advantageous Effects

A compound according to the present invention may be used as an organic material layer material, particularly, a hole injection material and/or a hole transport material in an organic light emitting device, and in the case of when the compound is used in the organic light emitting device, driving voltage of the device is lowered, light efficiency is improved, and a life span property of the device is improved because of thermal stability of the compound.

BEST MODE

Figure 1:
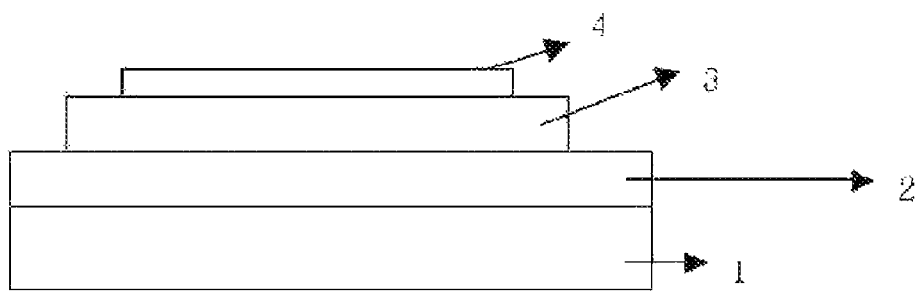
FIG. 1 illustrates an example of an organic light emitting device that comprises a substrate 1, an anode 2, a light emitting layer 3, and a cathode 4.
Figure 2:
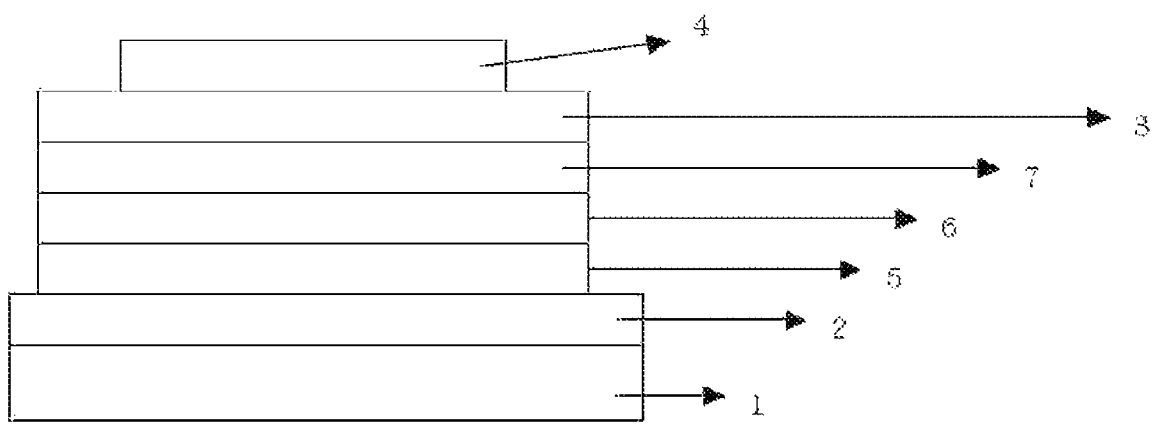
FIG. 2 illustrates an example of an organic light emitting device that comprises a substrate 1, an anode 2, a hole injection layer 5, a hole transport layer 6, a light emitting layer 7, an electron transport layer 8, and a cathode 4.

Hereinafter, the present invention will be described in more detail.

An aspect of the present invention relates to a compound that is represented by Formula 1.

The substituent group of Formula 1 will be described in detail.

l, m and n of Formula 1 are an integer in the range of 0 to 5.

In addition, the number of carbon atoms of alkyl group, alkylene group, and alkoxy group of Formula 1 is not particularly limited, but preferably in the range of 1 to 40 and more preferably 1 to 20.

In addition, the number of carbon atoms of alkenyl group, alkenylene group, acetyl group, acetylene group of Formula 1 is not particularly limited, but preferably in the range of 2 to 40 and more preferably 2 to 20.

In addition, the number of carbon atoms of aryl group, and arylene group of Formula 1 is not particularly limited, but preferably in the range of 6 to 40 and more preferably 6 to 20.

In addition, the number of carbon atoms of hetero ring group of Formula 1 is not particularly limited, but preferably in the range of 4 to 40 and more preferably 4 to 20, and the hetero ring group has preferably O, N or S as a heteroatom.

In addition, the number of carbon atoms of arylalkyl group of Formula 1 is not particularly limited, but preferably in the range of 7 to 40 and more preferably 7 to 20.

In addition, the number of carbon atoms of arylalkenyl group of Formula 1 is not particularly limited, but preferably in the range of 7 to 40 and more preferably 7 to 20.

In addition, the number of carbon atoms of arylamine group of Formula 1 is not particularly limited, but preferably in the range of 6 to 40 and more preferably 6 to 20.

In the case of when there is no specific description in Formula 1, the term "substituted or unsubstituted" means that it is unsubstituted or substituted by one or more substituent groups that are selected from the group consisting of halogen group, alkyl group, alkenyl group, alkoxy group, aryl group, arylalkyl group, arylalkenyl group, heteroring group, carbazolyl group, fluorenyl group, nitrile group and acetylene group, but they are not limited thereto.

The length of the alkyl group that is comprised in the compound does not affect the conjugation length of the compound, but incidentally may affect an application method of the compound to the organic light emitting device, for example, application of a vacuum deposition method or a solution coating method.

In Formula 1, it is preferable that $Y_1$ to $Y_3$ are each independently selected from the group consisting of $C_{6-20}$ arylene group that is unsubstituted or substituted by one or more substituent groups selected from the group consisting of halogen group, $C_{1-20}$ alkyl group, $C_{6-20}$ aryl group, $C_{7-20}$ arylalkyl group and $C_{4-20}$ hetero ring group; $C_{4-20}$ divalent hetero ring group that is unsubstituted or substituted by one or more substituent groups selected from the group consisting of halogen group, $C_{1-20}$ alkyl group, $C_{6-24}$ arylamine group, $C_{6-20}$ aryl group, $C_{7-20}$ arylalkyl group and $C_{4-20}$ hetero ring group and has O, N or S as a heteroatom; and fluorenylene group that is unsubstituted or substituted by one or more substituent groups selected from the group consisting of $C_{1-20}$ alkyl group, $C_{6-20}$ aryl group and $C_{7-20}$ arylalkyl group.

In addition, in Formula 1, $Y_1$ to $Y_3$ may be each independently selected from the group consisting of phenyl group, biphenyl group, terphenyl group, stilbene, naphthyl group, anthracenyl group, phenanthrene group, pyrenyl group, perylenyl group, fluorene group, thiophene group, furane group, pyrol group, imidazole group, thiazol group, oxazole group, oxadiazole group, triazole group, pyridyl group, pyradazine group, quinolinyl group, isoquinoline group and acrydyl group.

In addition, in Formula 1, as examples of the divalent hetero ring group of $Y_1$ to $Y_3$, there are a thiophene group, a furane group, a pyrol group, an imidazole group, a thiazol group, an oxazol group, an oxadiazol group, a triazol group, a pyridyl group, a pyradazine group, a quinolynyl group, an isoquinoline group, an acrydyl group and the like, but they are not limited thereto.

In Formula 1, $R_1$, $R_3$ and $R_4$ may be each independently selected from the group consisting of $C_{1-20}$ alkyl group that is unsubstituted or substituted by one or more substituent groups selected from the group consisting of $C_{1-20}$ alkyl group, $C_{6-20}$ aryl group, $C_{7-20}$ arylalkyl group and $C_{4-20}$ hetero ring group; $C_{6-20}$ aryl group that is unsubstituted or substituted by one or more substituent groups selected from the group consisting of halogen group, $C_{1-20}$ alkyl group, $C_{12-24}$ arylamine group, $C_{6-20}$ aryl group, $C_{7-20}$ arylalkyl group and $C_{4-20}$ hetero ring group; $C_{4-20}$ hetero ring group that is unsubstituted or substituted by one or more substituent groups selected from the group consisting of halogen group, $C_{1-20}$ alkyl group, $C_{6-24}$ arylamine group, $C_{6-20}$ aryl group, $C_{7-20}$ arylalkyl group and $C_{4-20}$ hetero ring group and has O, N or S as a heteroatom; amine group that is substituted by one or more substituent groups selected from the group consisting of $C_{1-20}$ alkyl group, $C_{6-20}$ aryl group and $C_{7-20}$ arylalkyl group; fluorenyl group that is substituted by $C_{1-20}$ alkyl group or $C_{6-20}$ aryl group; bisspirofluorenyl group; cyano group; nitro group; and silane group that is substituted by $C_{6-20}$ aryl group.

In Formula 1, $R_2$ may be selected from the group consisting of $C_{1-20}$ alkyl group that is unsubstituted or substituted by one or more substituent groups selected from the group consisting of $C_{1-20}$ alkyl group, $C_{6-20}$ aryl group, $C_{7-20}$ arylalkyl group and $C_{4-20}$ hetero ring group; $C_{6-20}$ aryl group that is unsubstituted or substituted by one or more substituent groups selected from the group consisting of halogen group, $C_{1-20}$ alkyl group, $C_{6-20}$ aryl group, $C_{7-20}$ arylalkyl group and $C_{4-20}$ hetero ring group; $C_{4-20}$ hetero ring group that is unsubstituted or substituted by one or more substituent groups selected from the group consisting of halogen group, $C_{1-20}$ alkyl group, $C_{6-20}$ aryl group, $C_{7-20}$ arylalkyl group and $C_{4-20}$ hetero ring group and has O, N or S as a heteroatom; fluorenyl group that is substituted by $C_{1-20}$ alkyl group or $C_{6-20}$ aryl group; bisspirofluorenyl group; cyano group; nitro group; silane group that is unsubstituted or substituted by $C_{6-20}$ aryl group; and halogen group.

In Formula 2, $R_5$ to $R_7$ are each independently selected from the group consisting of hydrogen; halogen group; $C_{1-20}$ alkyl group that is unsubstituted or substituted by one or more substituent groups selected from the group consisting of halogen group, $C_{1-20}$ alkyl group, $C_{6-20}$ aryl group, $C_{7-20}$ arylalkyl group and $C_{4-20}$ hetero ring group; $C_{6-20}$ aryl group that is unsubstituted or substituted by one or more substituent groups selected from the group consisting of halogen group, $C_{1-20}$ alkyl group, $C_{6-20}$ aryl group, $C_{7-20}$ arylalkyl group and $C_{4-20}$ hetero ring group; and $C_{4-40}$ hetero ring group that is unsubstituted or substituted by one or more substituent groups selected from the group consisting of halogen group, $C_{1-20}$ alkyl group, $C_{12-24}$ arylamine group, $C_{6-20}$ aryl group, $C_{7-20}$ arylalkyl group and $C_{4-20}$ hetero ring group and has O, N or S as a heteroatom, and they may form an aliphatic or hetero condensation ring in conjunction with adjacent groups.

In Formulas 1 and 2, $R_1$ to $R_7$ may be each independently selected from the group consisting of phenyl group, biphenyl group, terphenyl group, stilbene, naphthyl group, anthracenyl group, phenanthrene group, pyrenyl group, perylenyl group, fluorene group, thiophene group, furane group, pyrol group, imidazole group, thiazol group, oxazole group, oxadiazole group, triazole group, pyridyl group, pyradazine group, quinolinyl group, isoquinoline group and acrydyl group.

In addition, in Formulas 1 and 2, $R_1$ to $R_7$ are preferably monocyclic aromatics such as phenyl group, biphenyl group, terphenyl group, stilbene and polycyclic aromatics such as naphthyl group, anthracenyl group, phenanthrene group, pyrenyl group, perylenyl group, and fluorene group as the aryl group, but they are not limited thereto.

In addition, in Formulas 1 and 2, $R_1$ to $R_7$ are preferably thiophen group, furane group, pyrol group, imidazole group, thiazol group, oxazole group, oxadiazole group, triazole group, pyridyl group, pyradazine group, quinolinyl group, isoquinoline group and acrydyl group as the hetero ring group, but they are not limited thereto.

In addition, in Formula 1, it is preferable that $R_2$ is selected from the group consisting of alkyl group that is selected from the group consisting of methyl group, ethyl group and propyl group; aryl group that is selected from the group consisting of phenyl group, biphenyl group and naphthyl group; fluorenyl group; and bisspirofluorenyl group, but is not limited thereto.

In addition, in Formula 1, it is preferable that $R_2$ is selected from the group consisting of hetero ring that is selected from the group consisting of thiophene group and furane group; alkoxy group that is selected from the group consisting of methoxy group and ethoxy group; cyano group; nitro group; silane group; and halogen group, but is not limited thereto.

As described above, in the case of when $R_2$ of Formula 1 is selected from the group consisting of alkyl group that is selected from the group consisting of methyl group, ethyl group and propyl group; aryl group that is selected from the group consisting of phenyl group, biphenyl group and naphthyl group; fluorenyl group; bisspirofluorenyl group; hetero ring that is selected from the group consisting of thiophene group and furane group; alkoxy group that is selected from the group consisting of methoxy group and ethoxy group; cyano group; nitro group; silane group; and halogen group, when the compound according to the present invention is used in the organic light emitting device, it is possible to reduce driving voltage of the device, and improve light efficiency, and a life span of the device due to thermal stability of the compound.

It is preferable that the compound that is represented by Formula 2 is any one of the following Structural Formulas, but it is not limited thereto.

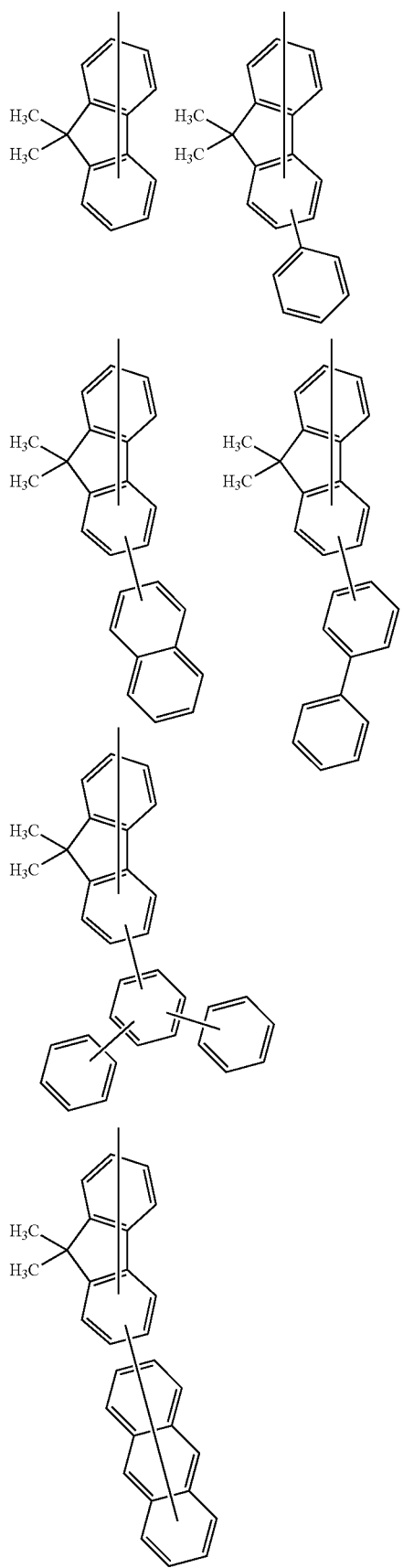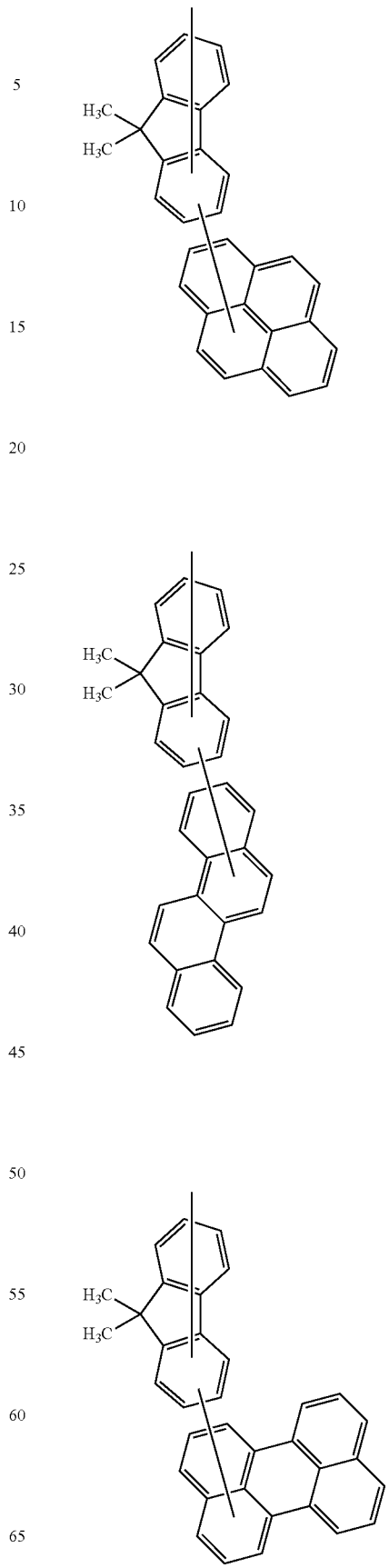

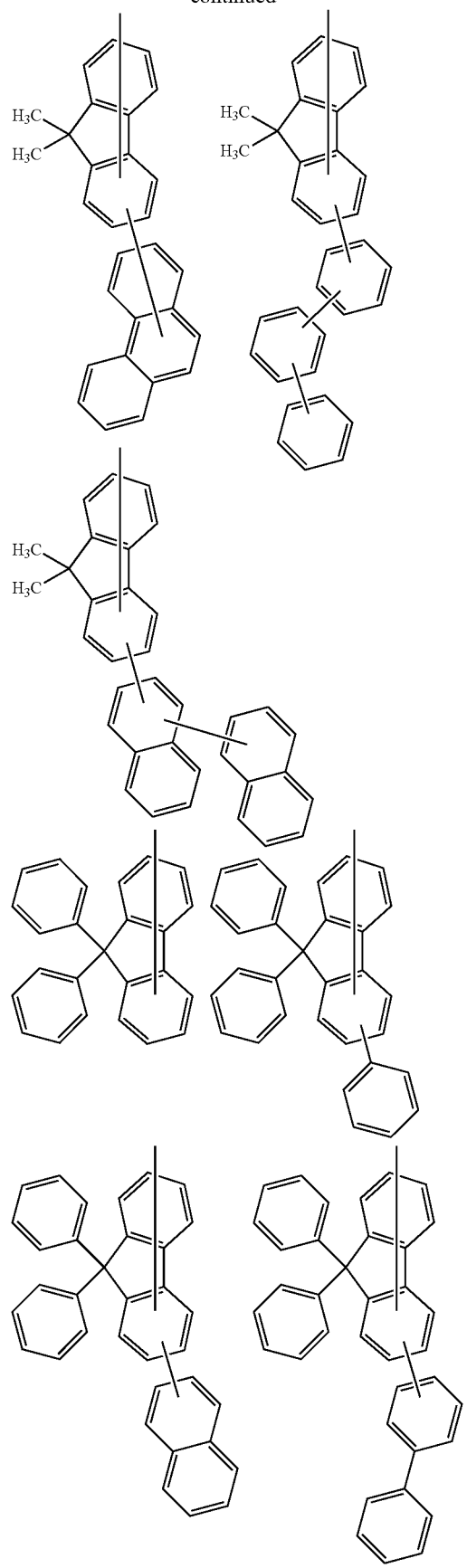
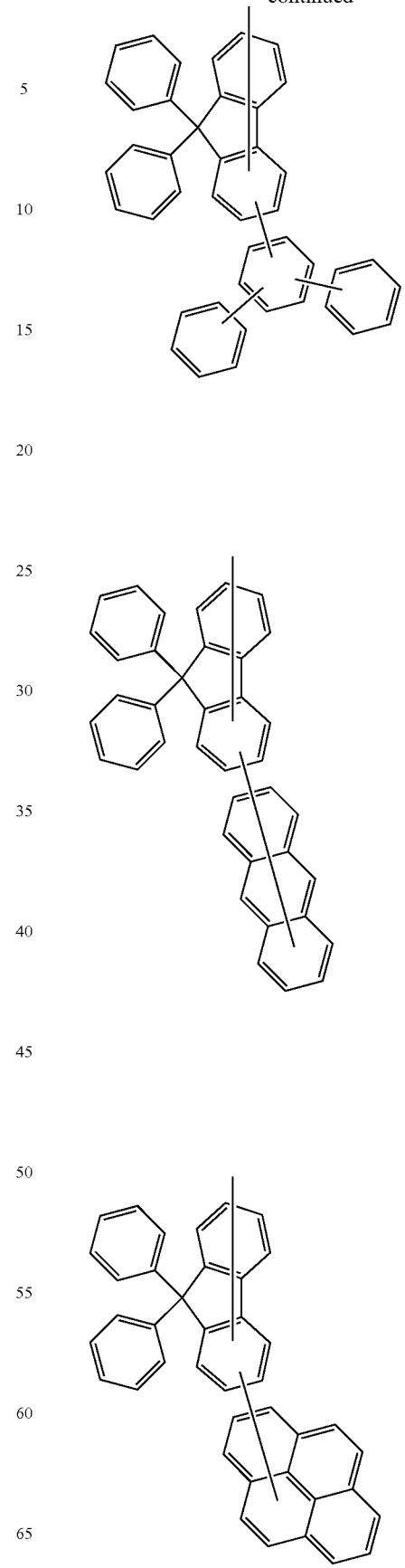

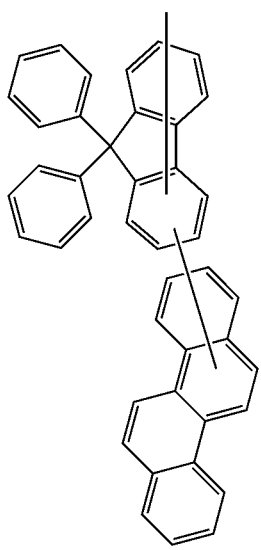
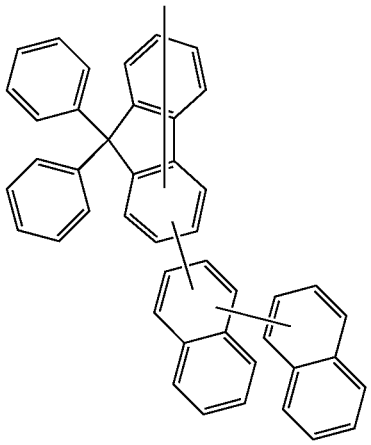
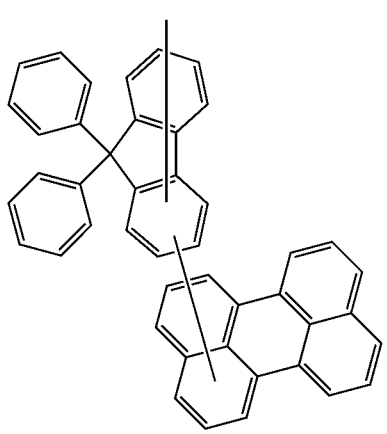
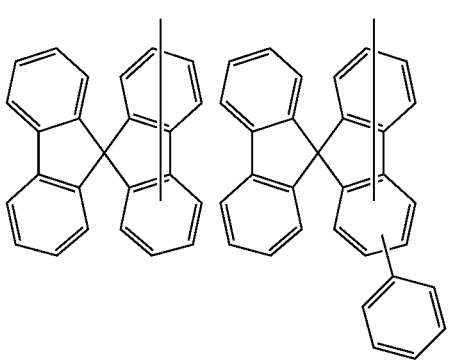
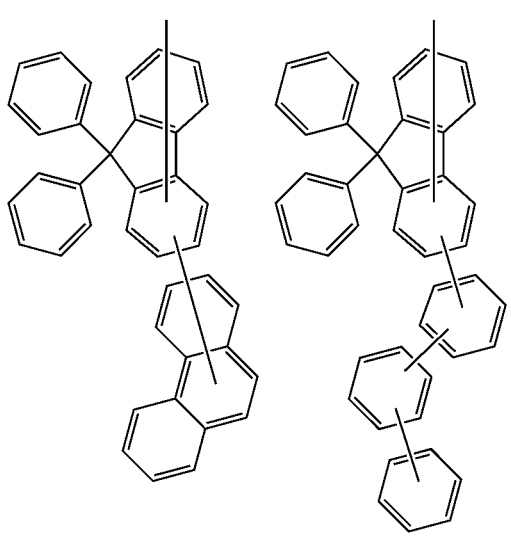
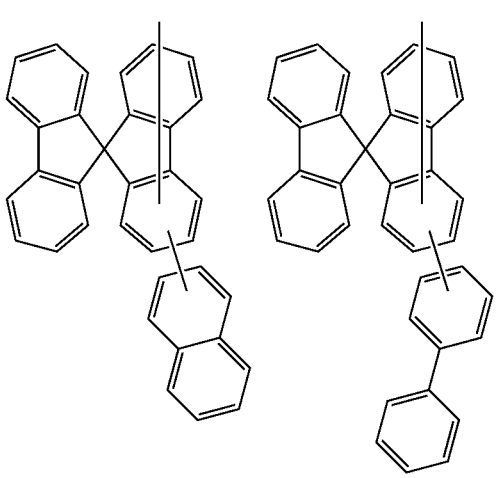

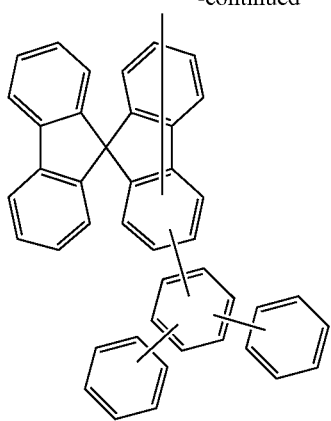
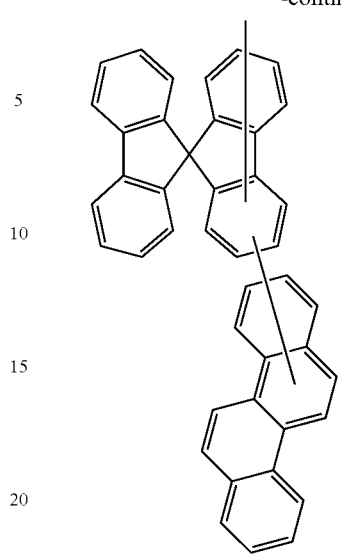
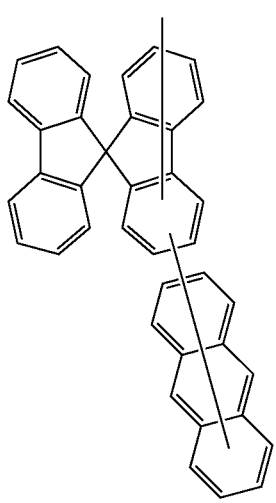
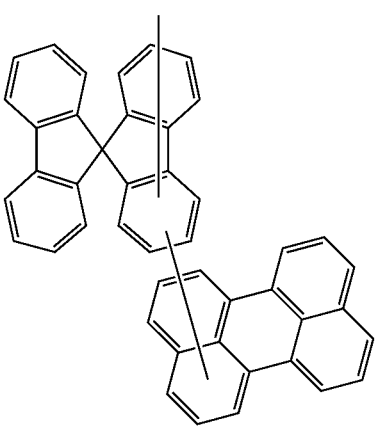
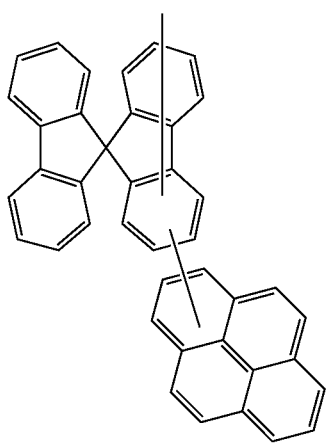
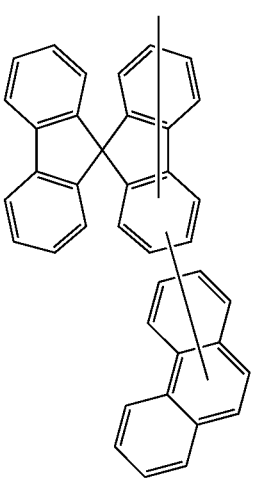

-continued
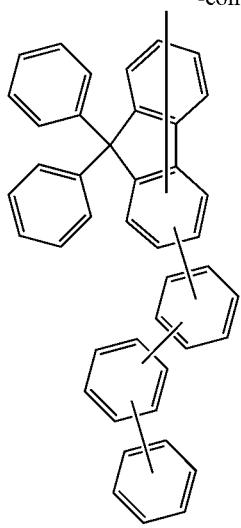
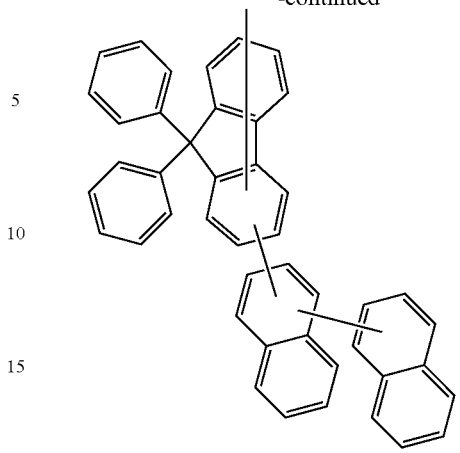
It is preferable that the compound that is represented by Formula 1 is represented by any one of the following Structural Formulas 1 to 80, but it is not limited thereto.
Structural Formula 1
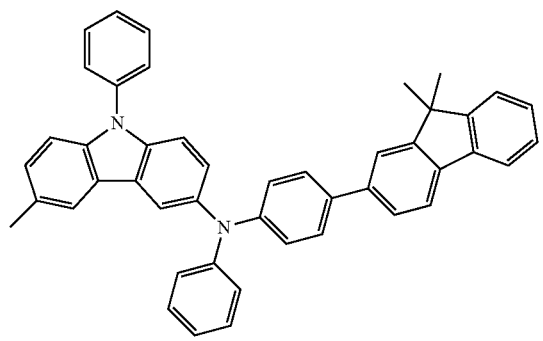
Structural Formula 2
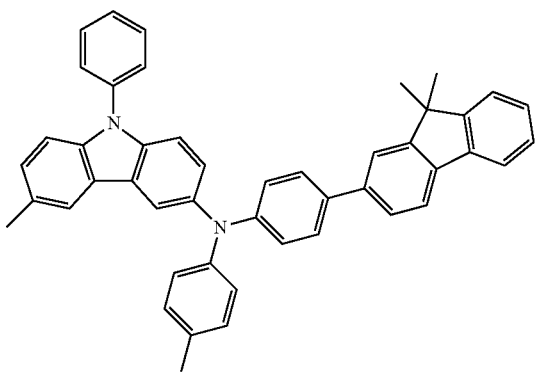
Structural Formua 3
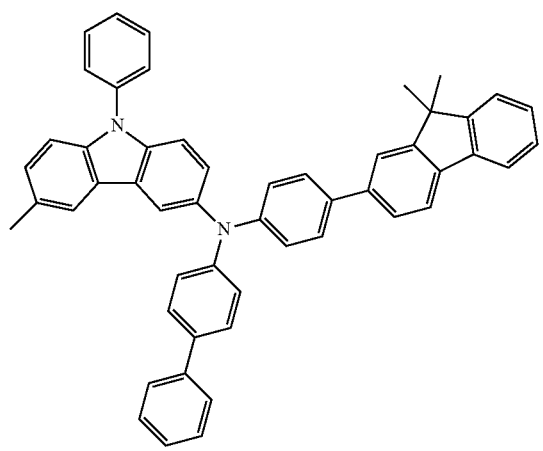
Structural Formula 4
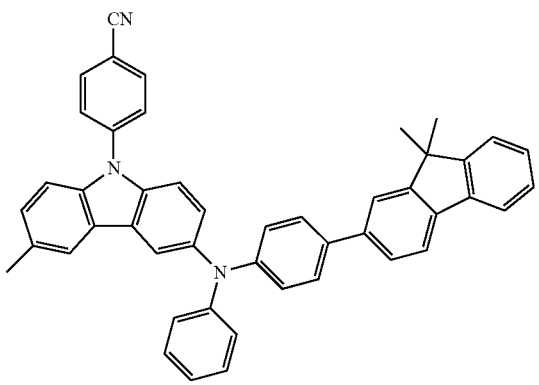

-continued
Structural Formula 5
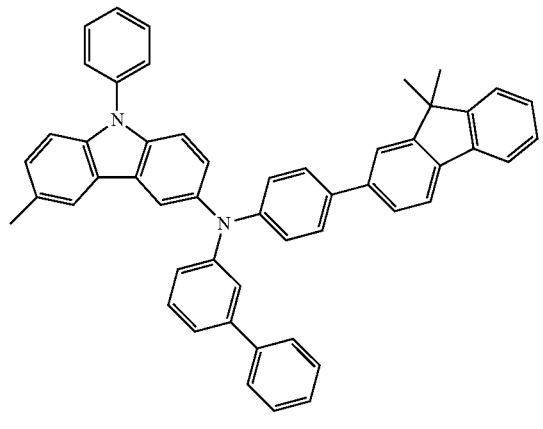
Structural Formula 6
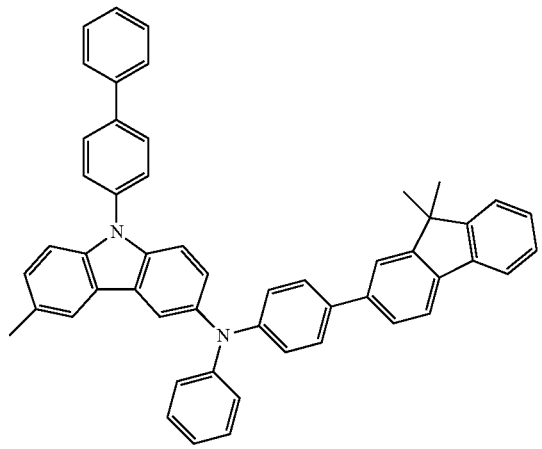
Structural Formula 7
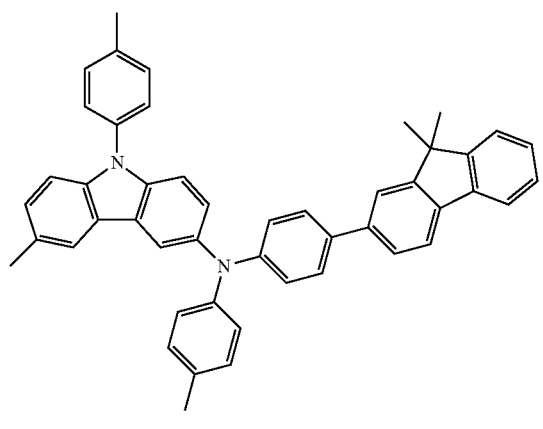
Structural Formula 8
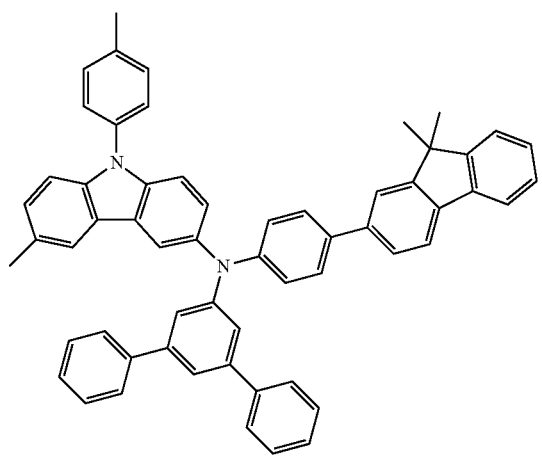
Structural Formula 9
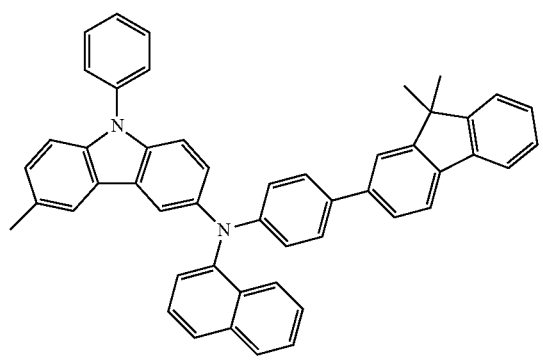
Structural Formual 10
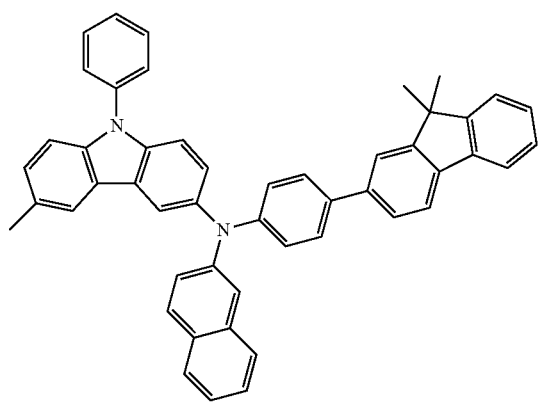

Structural Formula 11
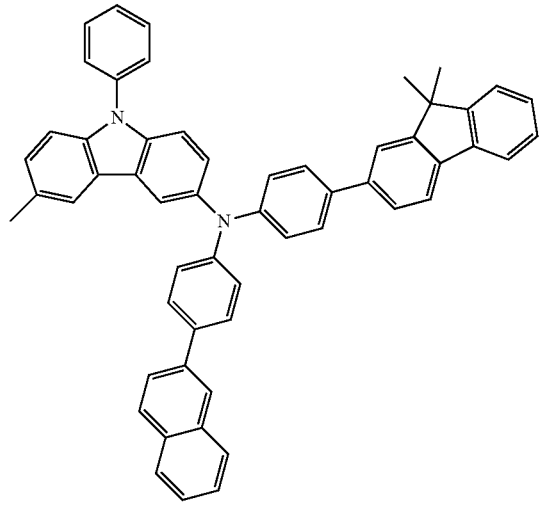
Structural Formula 12
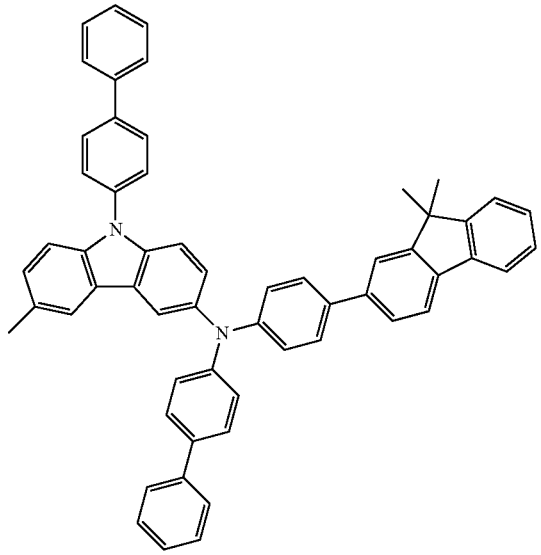
Structural Formula 13
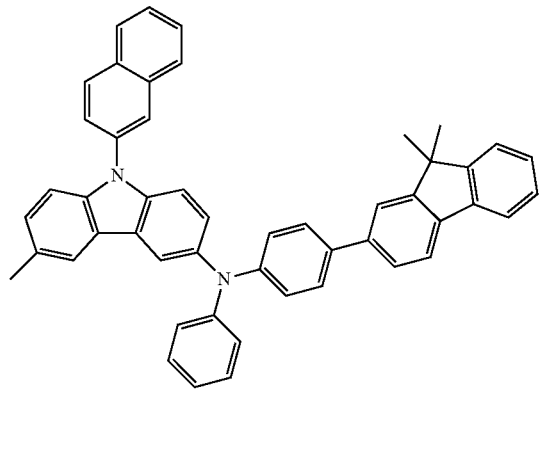
Structural Formula 14
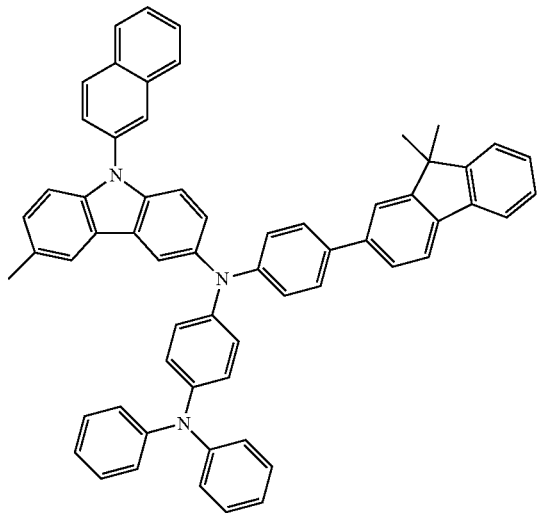
Structural Formula 15
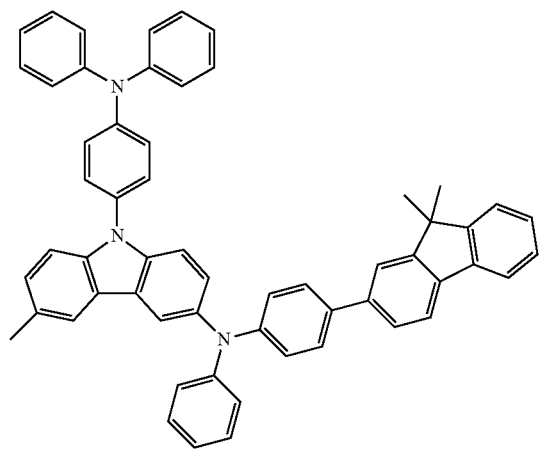
Structural Formula 16
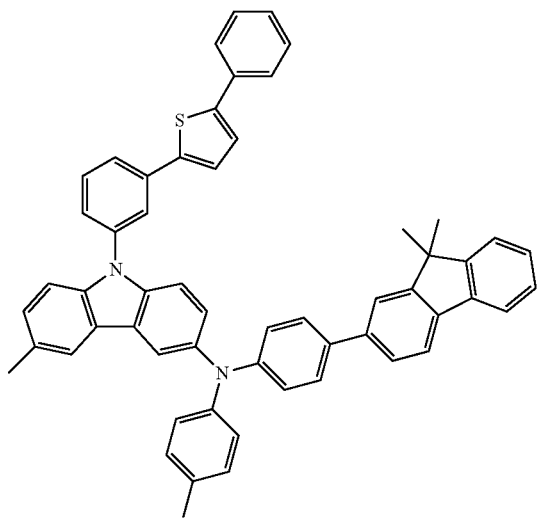

-continued
Structural Formula 17
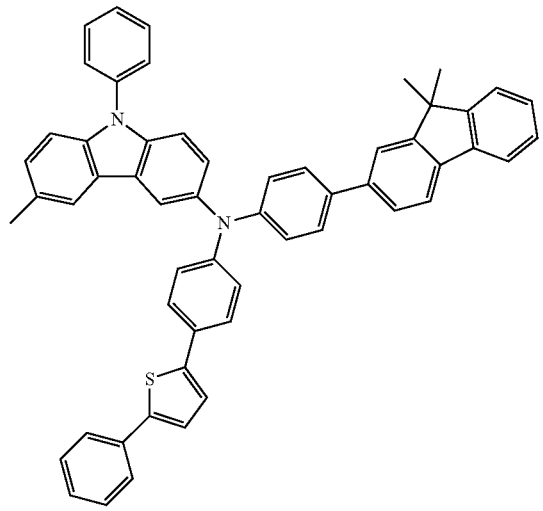
Structural Formula 18
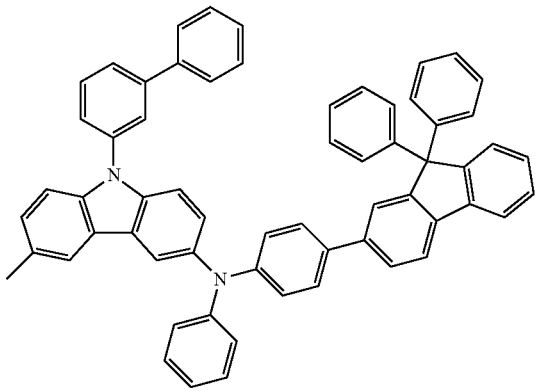
Structural Formula 19
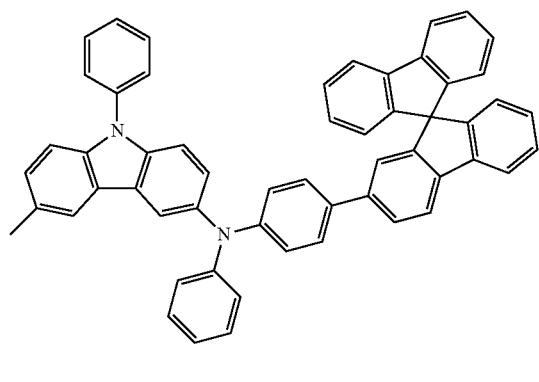
Structural Formula 20
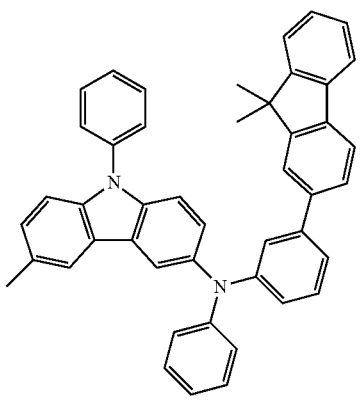
Structural Formula 21
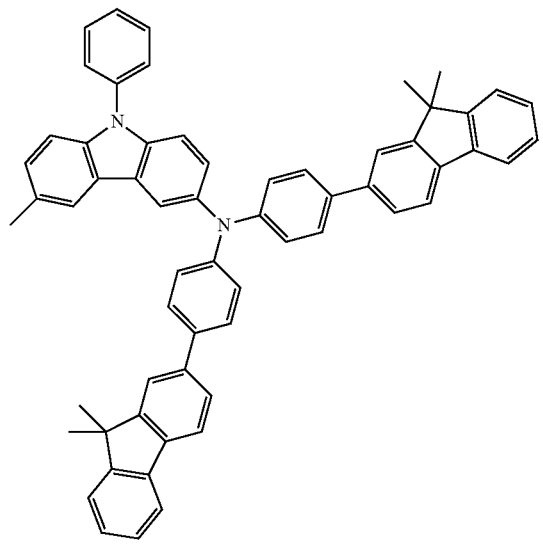
Structural Formula 22
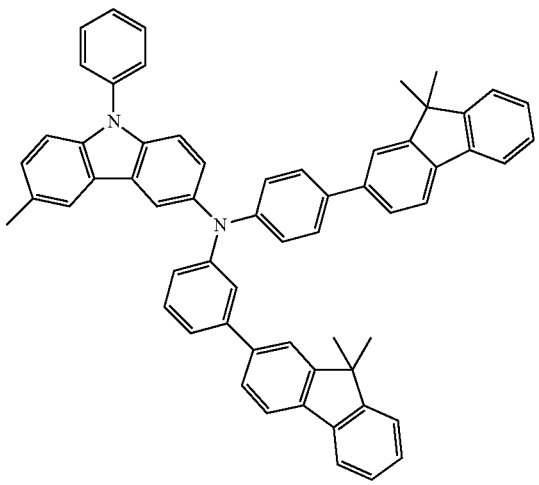

-continued
Structural Formula 23
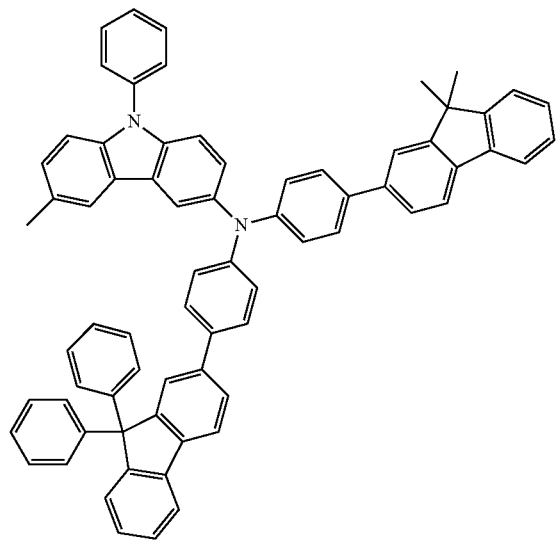
Structural Formula 24
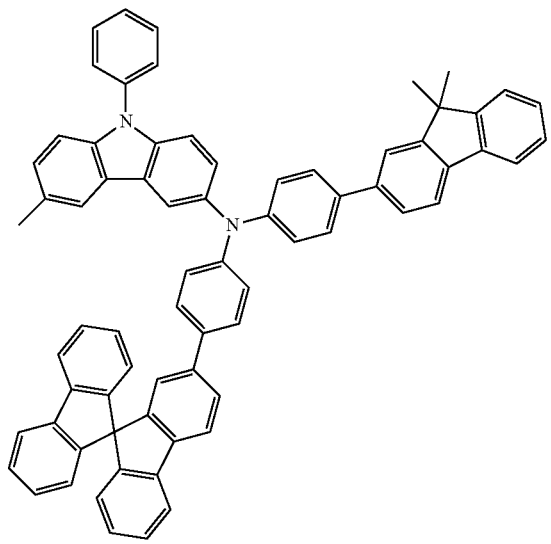
Structural Formula 25
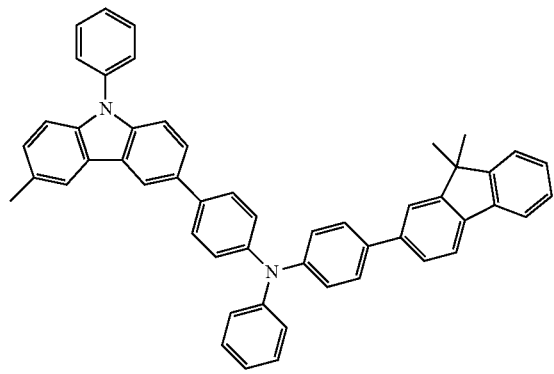
Structural Formula 26
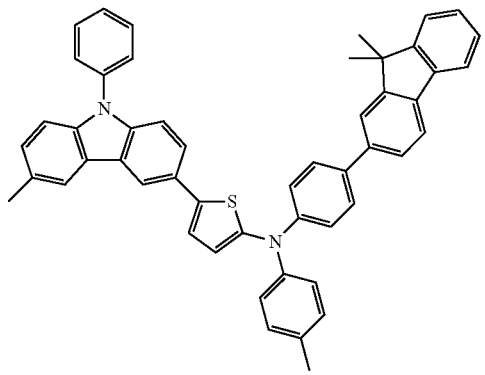
Structural Formula 27
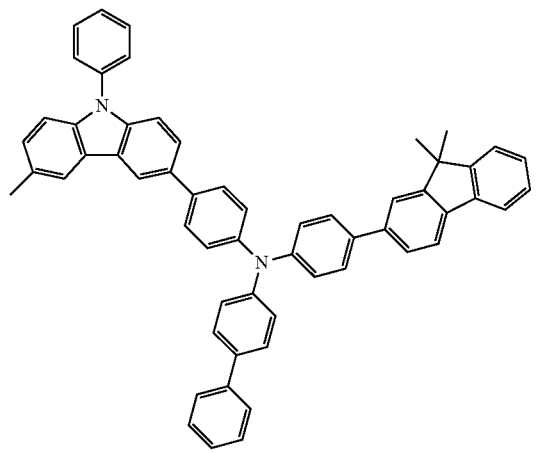
Structural Formula 28
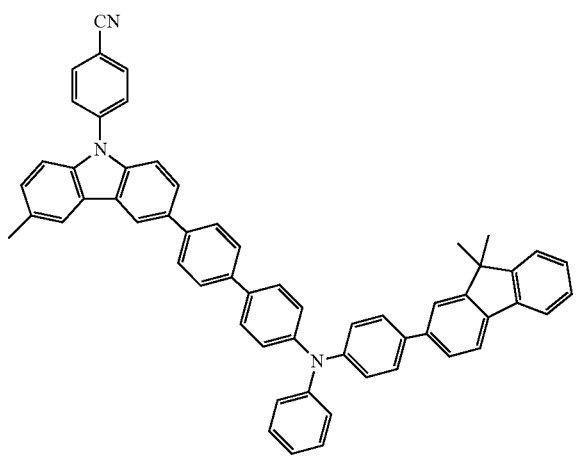

-continued
Structural Formula 29
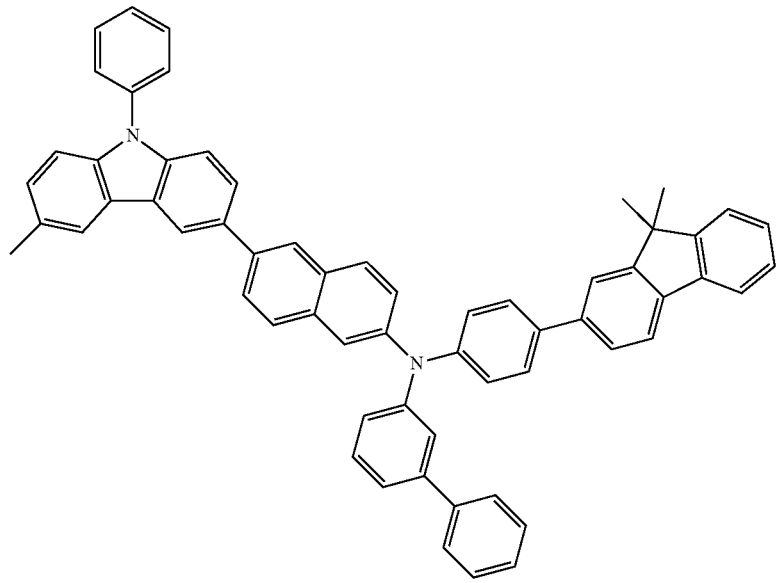
Structural Formula 30
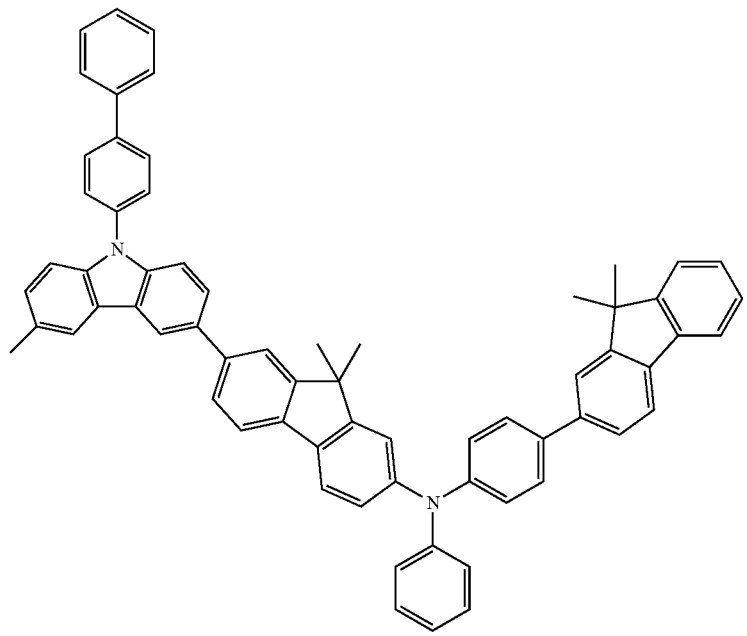
Structural Formula 31
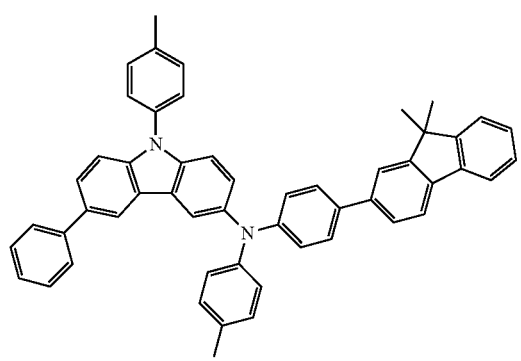
Structural Formula 32
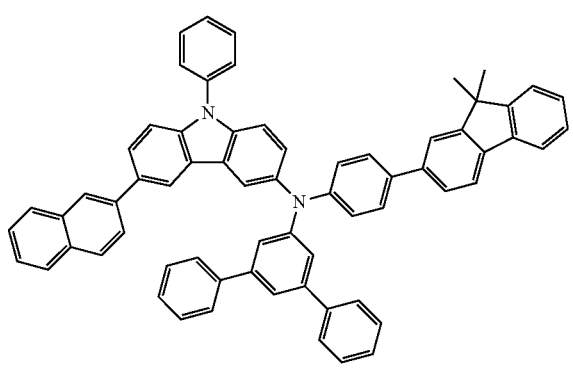

Structural Formula 33
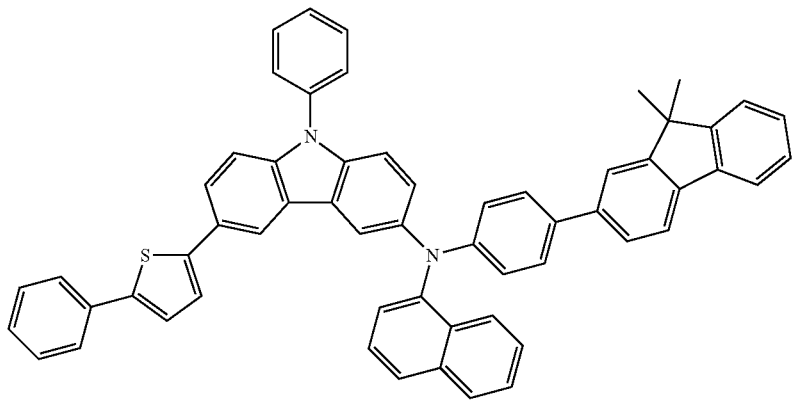
Structural Formula 34
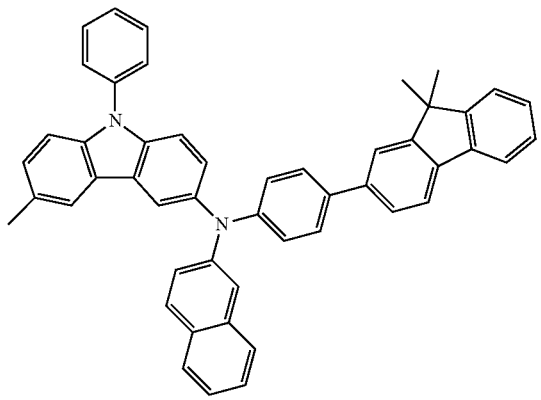
Structural Formula 35
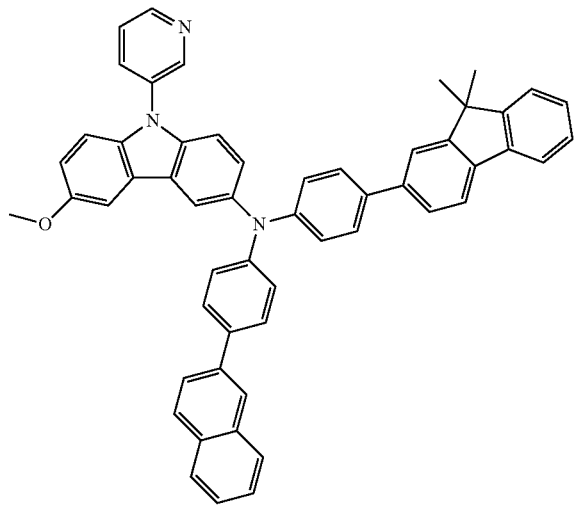
Structural Formula 36
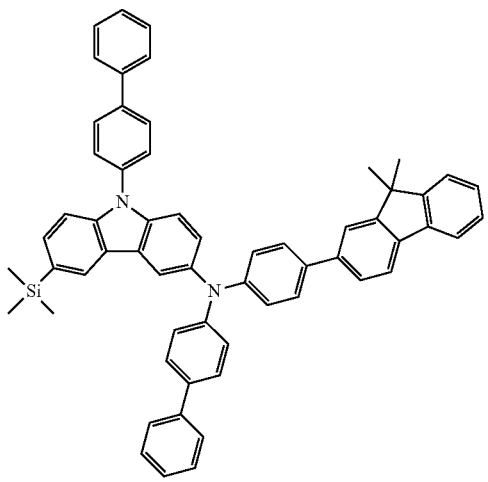
Structural Formula 37
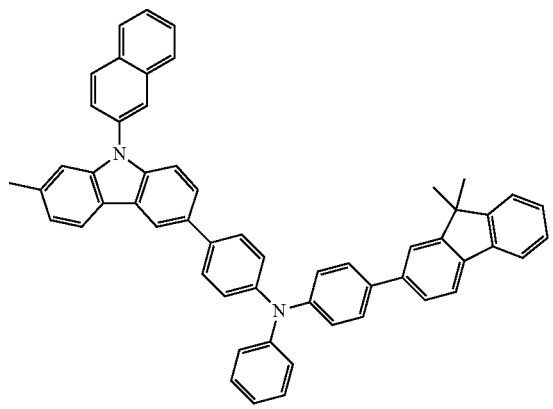

Structural Formula 38
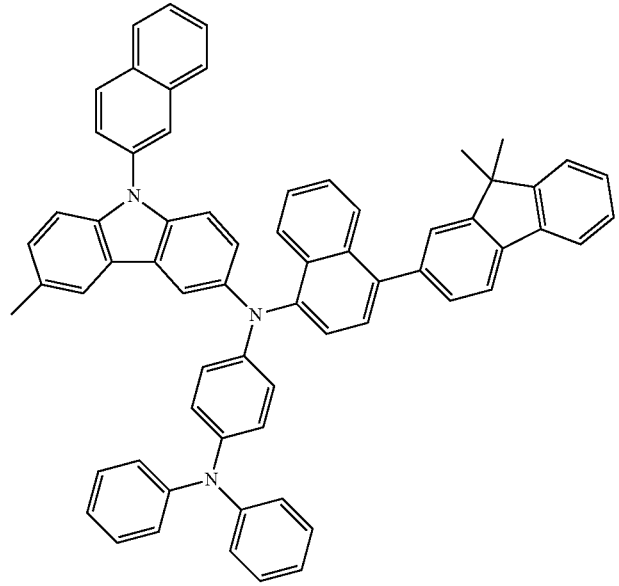
Structural Formula 39
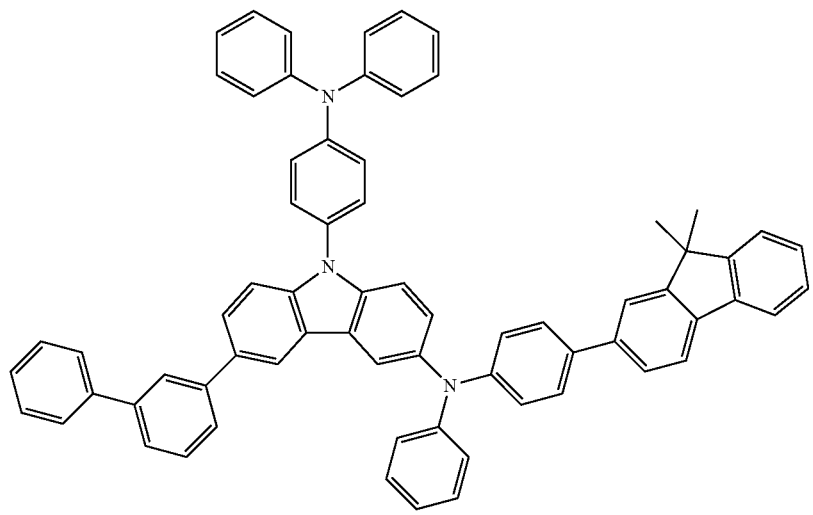
Structural Formula 40
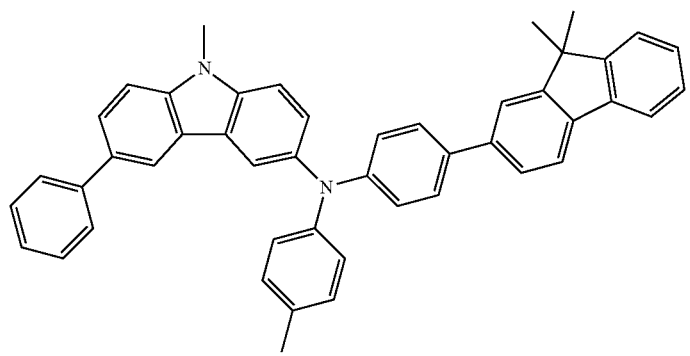

-continued
Structural Formula 41
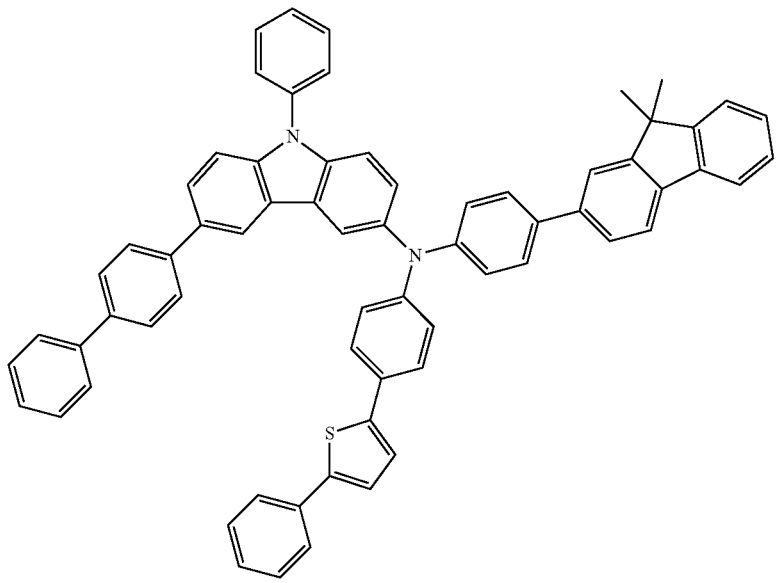
Structural Formula 42
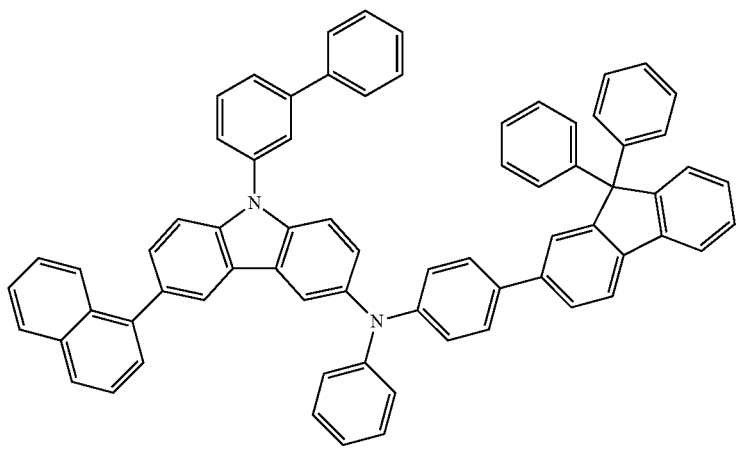
Structural Formula 43
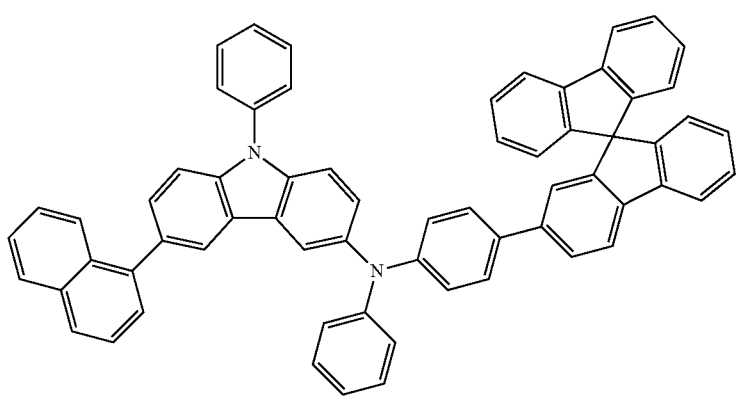

Structural Formula 44
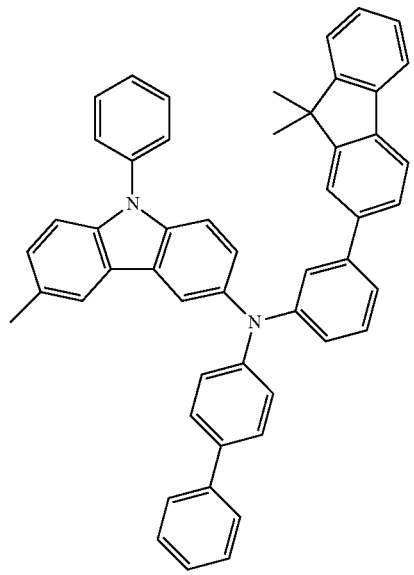
Structural Formula 45
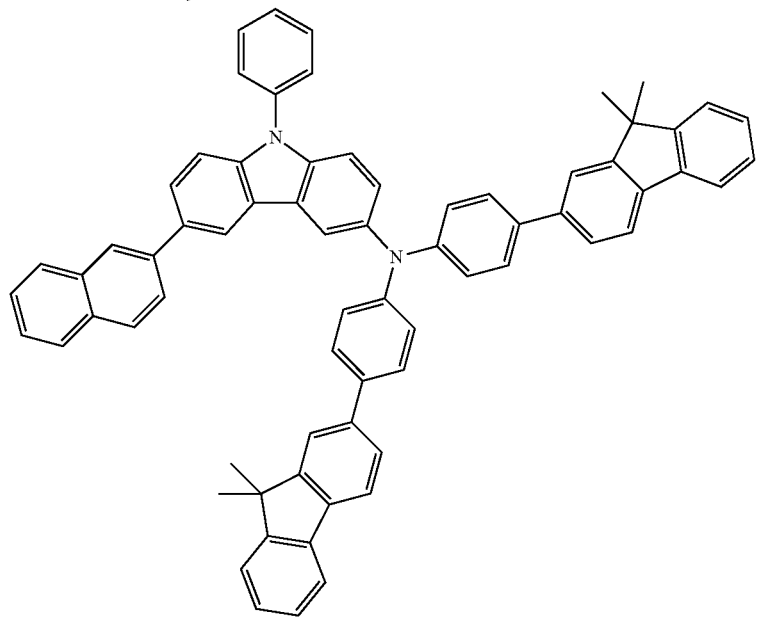
Structural Formula 46
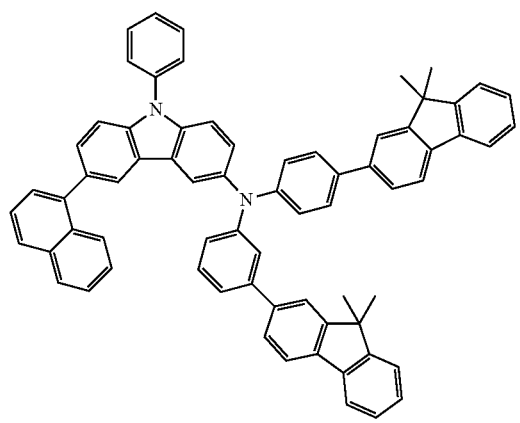
Structural Formula 47
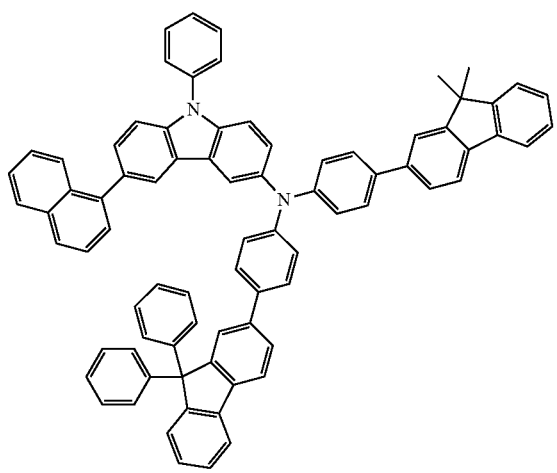

-continued
Structural Formula 48
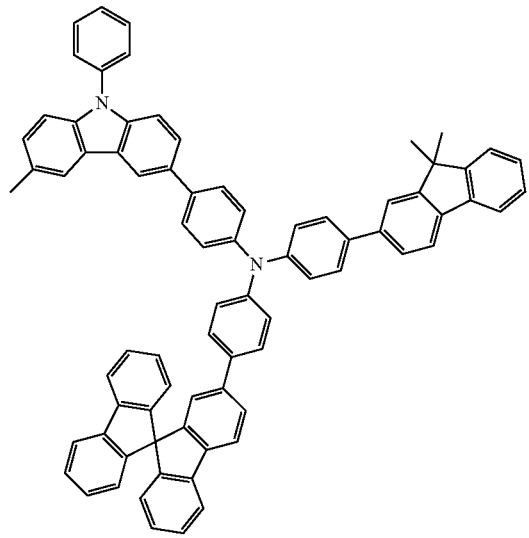
Structural Formula 49
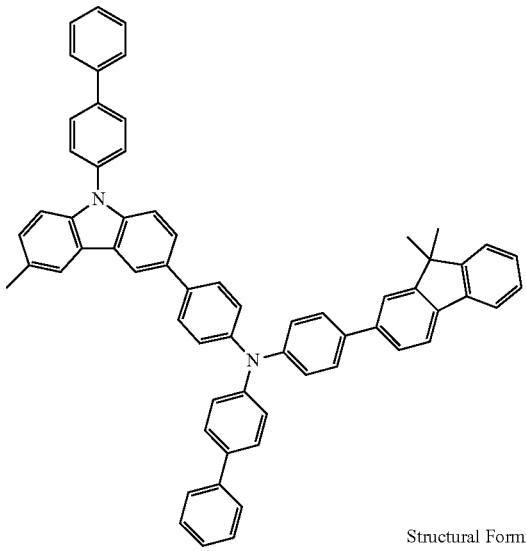
Structural Formula 50
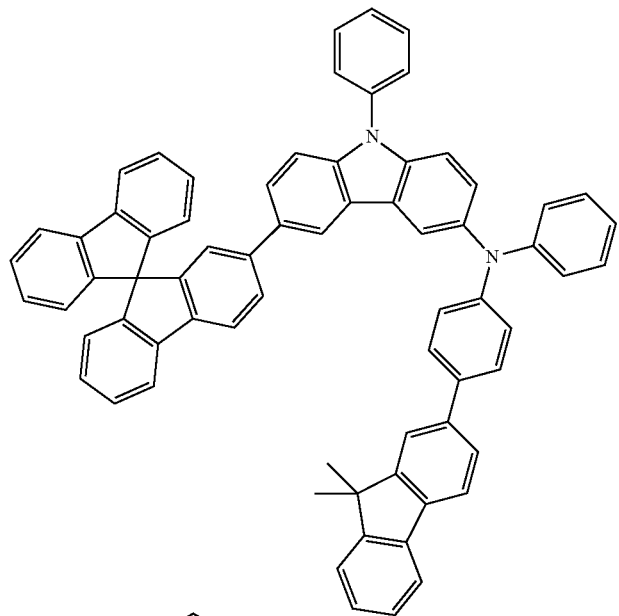
Structural Formula 51
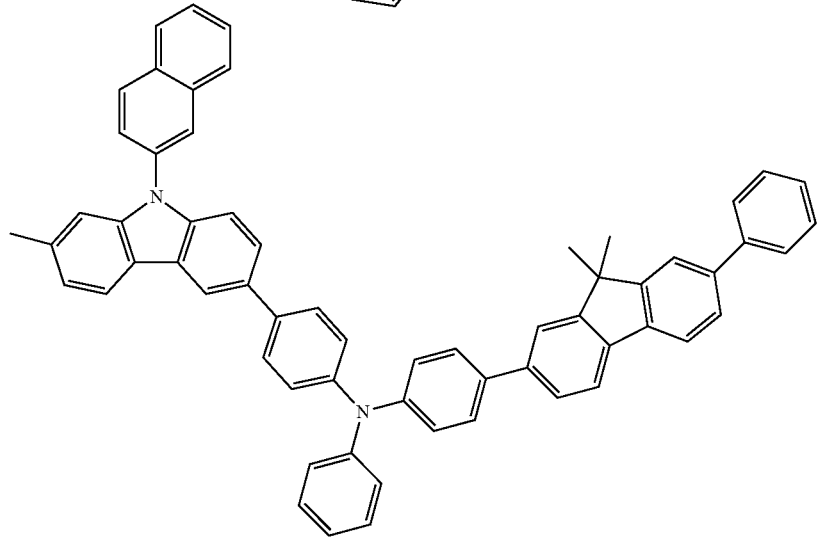

Structural Formula 52
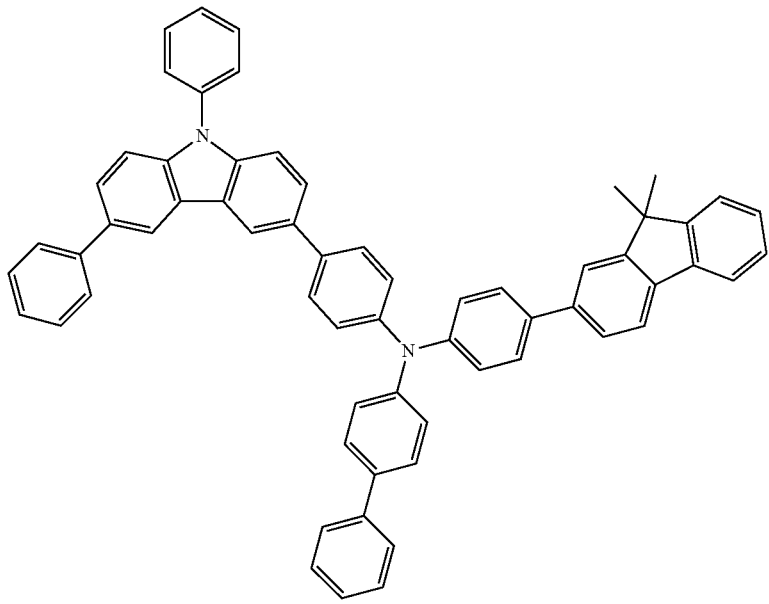
Structural Formula 53
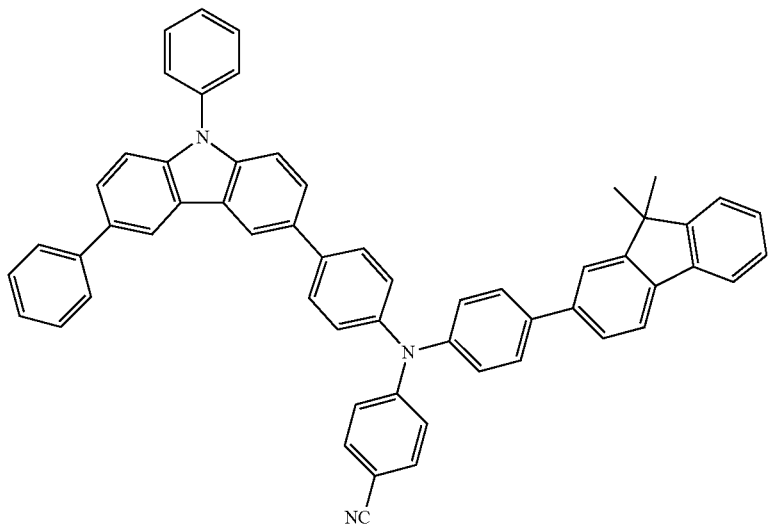
Structural Formula 54
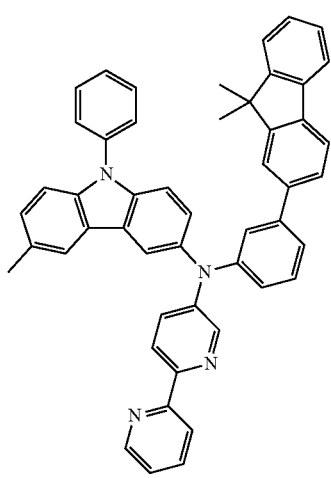
Structural Formula 55
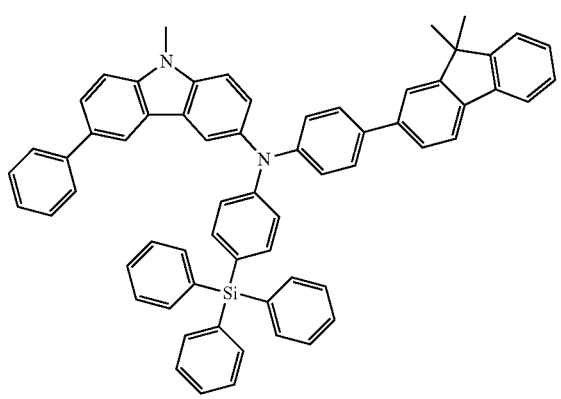

-continued
Structural Formula 56
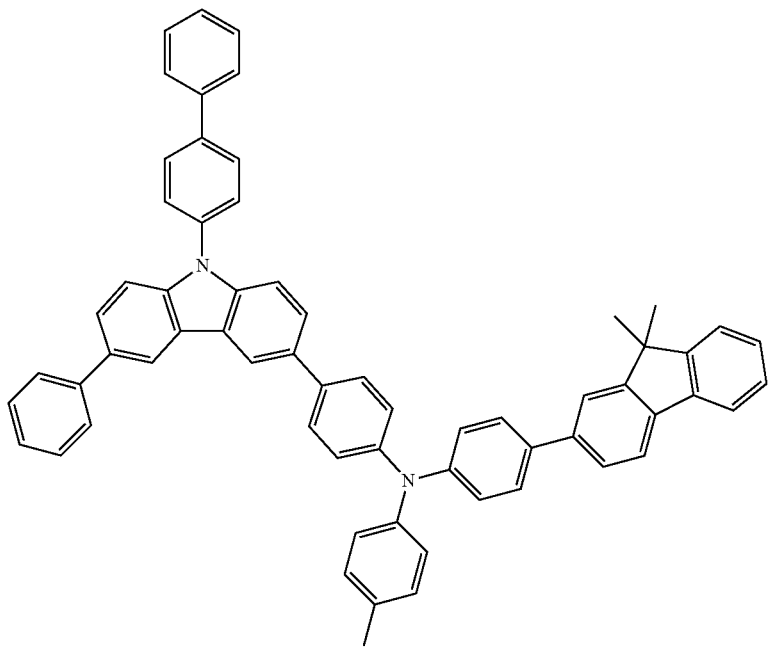
Structural Formula 57
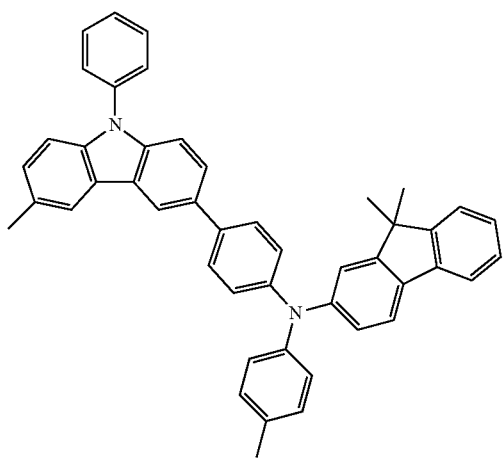
Structural Formula 58
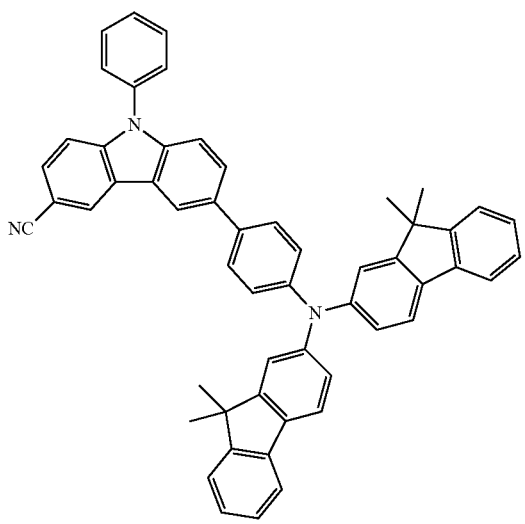
Structural Formula 59
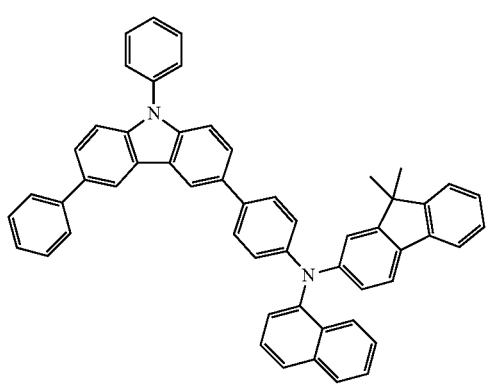
Structural Formula 60
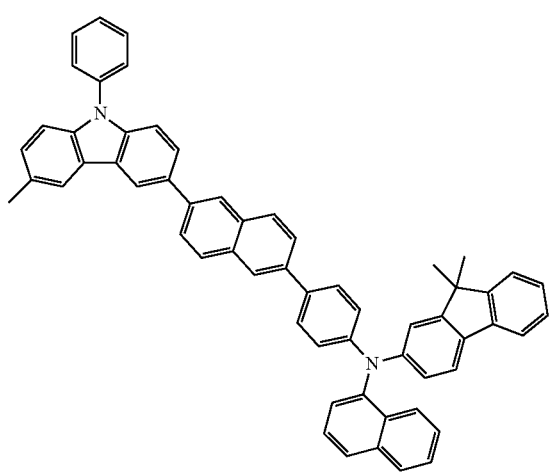

Structural Formula 61
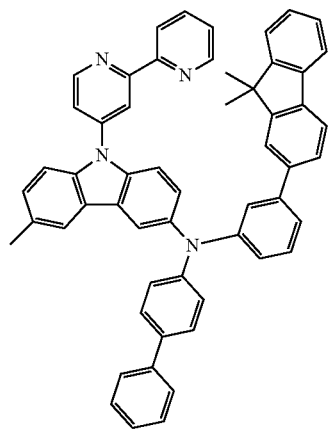
Structural Formula 62
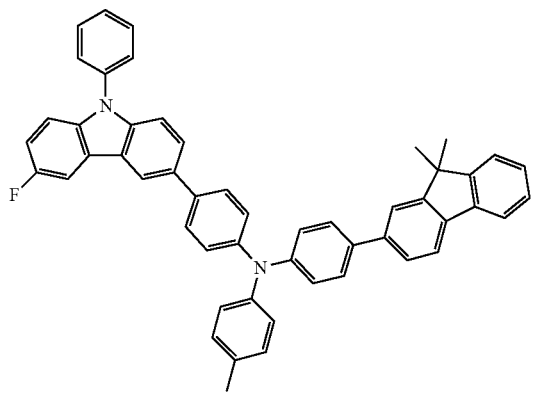
Structural Formula 63
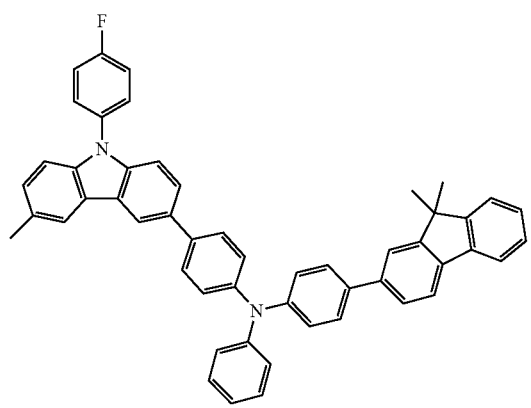
Structural Formula 64
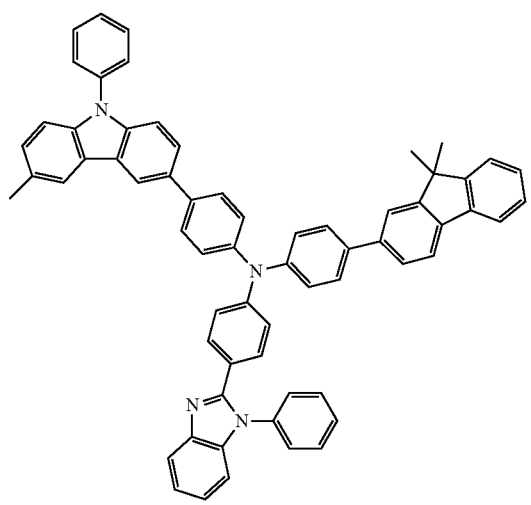
Structural Formula 65
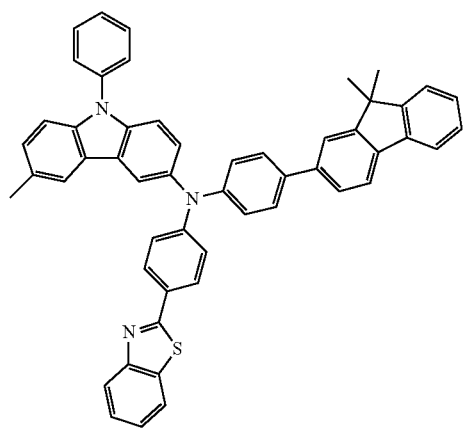
Structural Formula 66
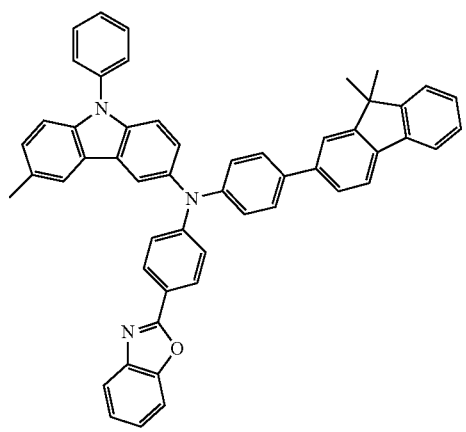

Structural Formula 67
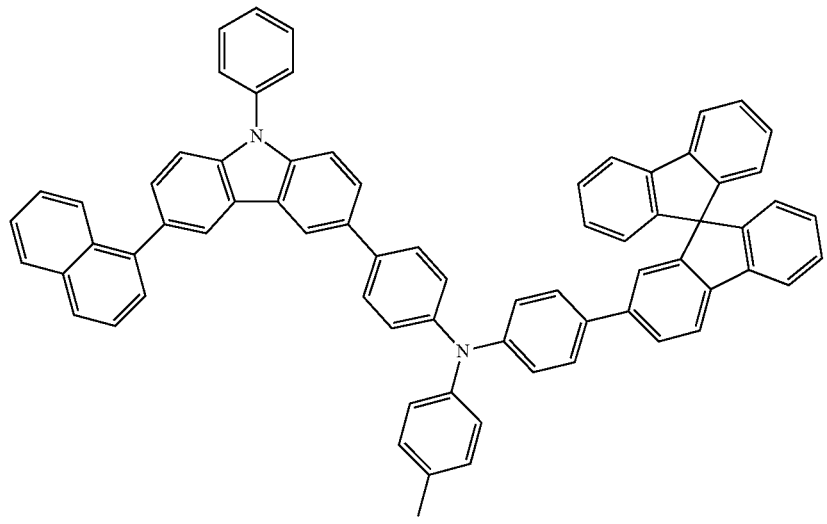
Structural Formula 68
Structural Formula 69
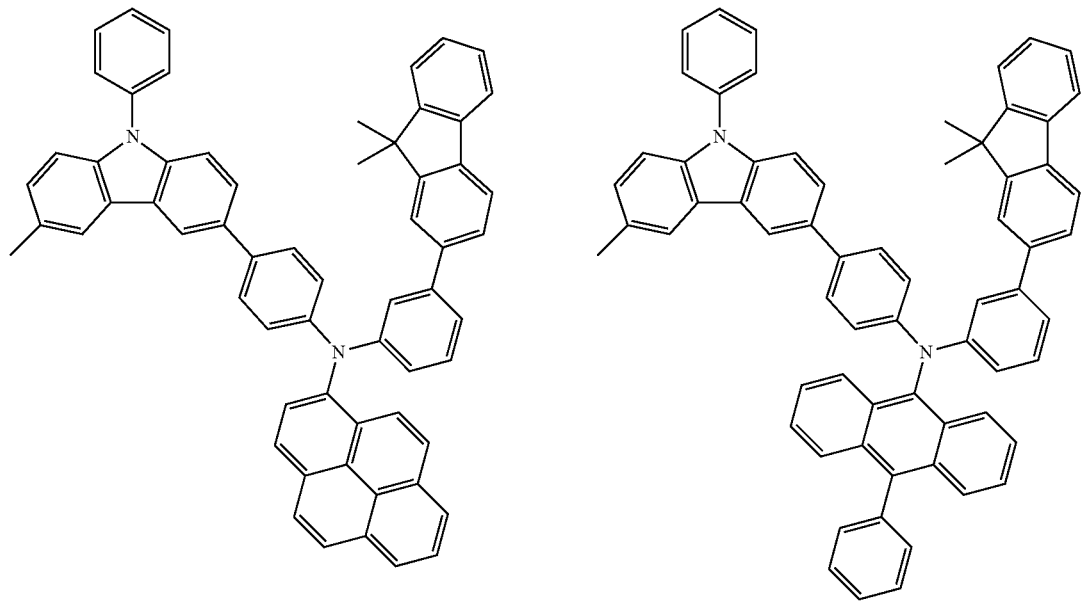
Structural Formula 70
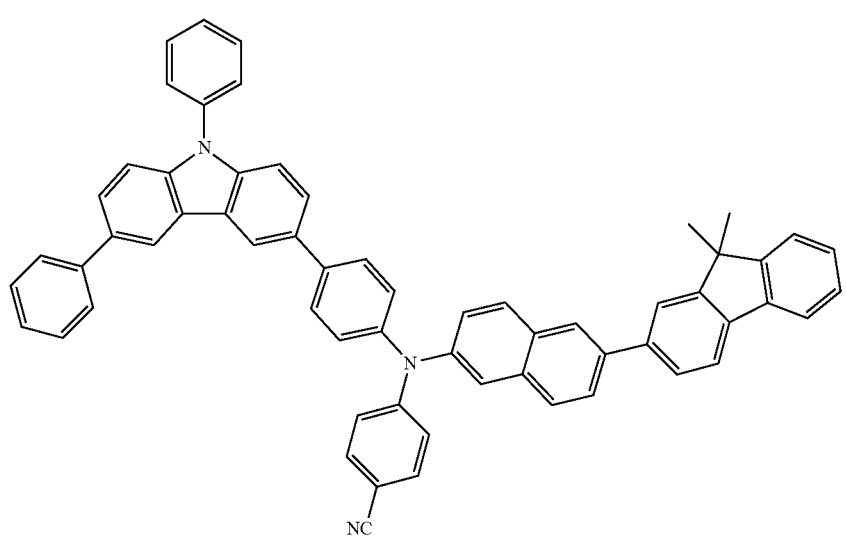

Structural Formula 71
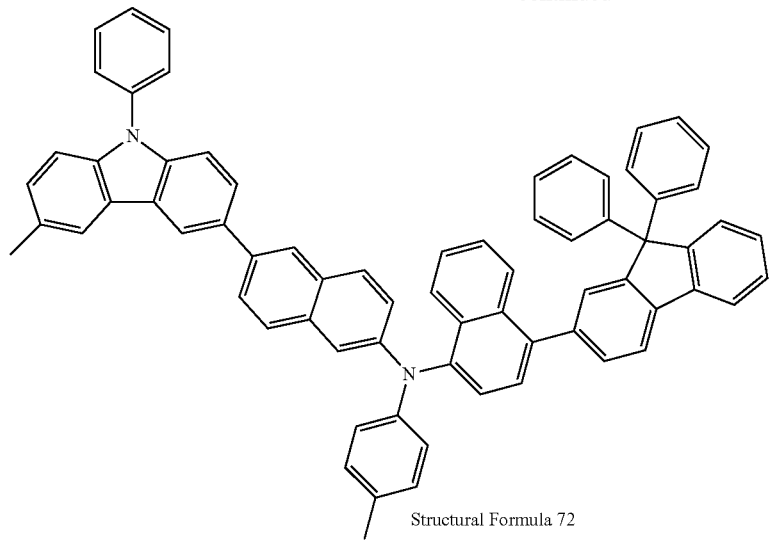
Structural Formula 72
Structural Formula 73
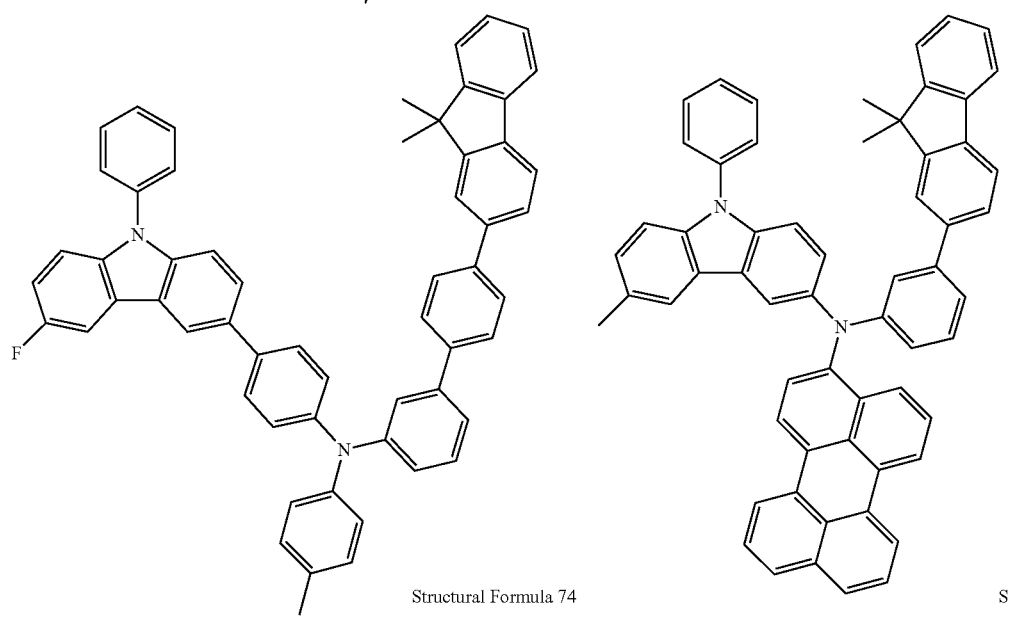
Structural Formula 74
Structural Formula 75
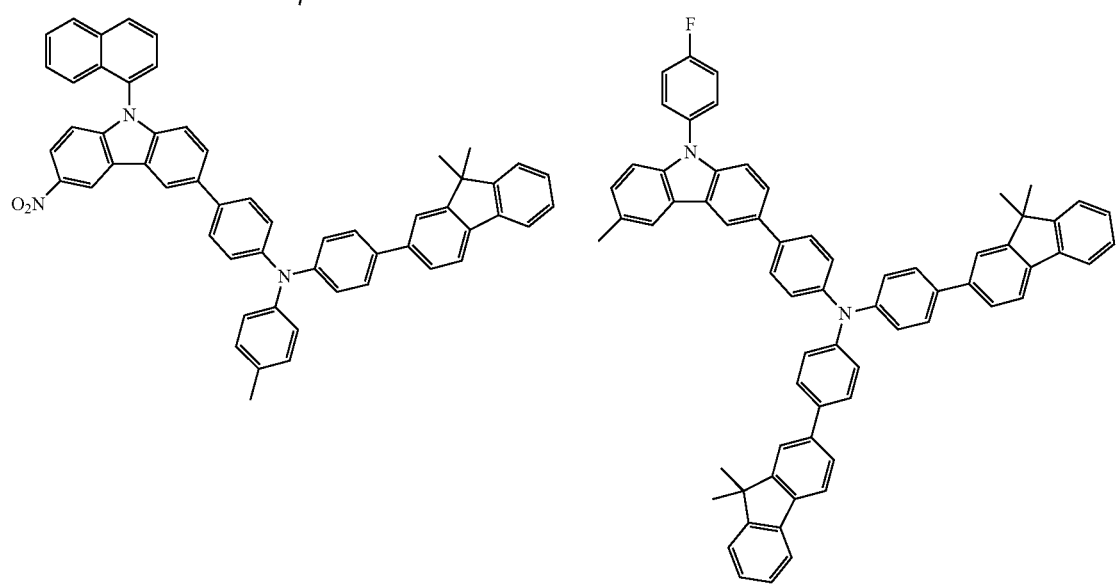

Structural Formula 76
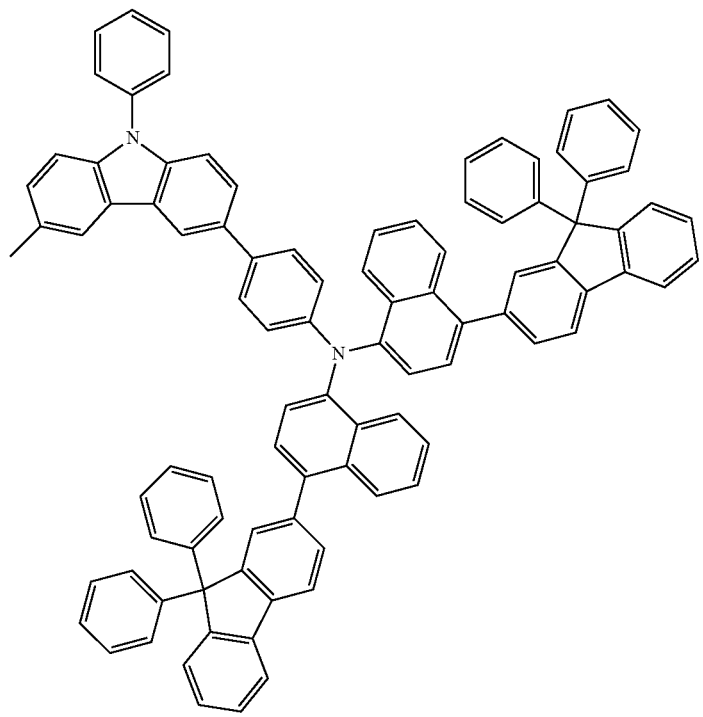
Structural Formula 77
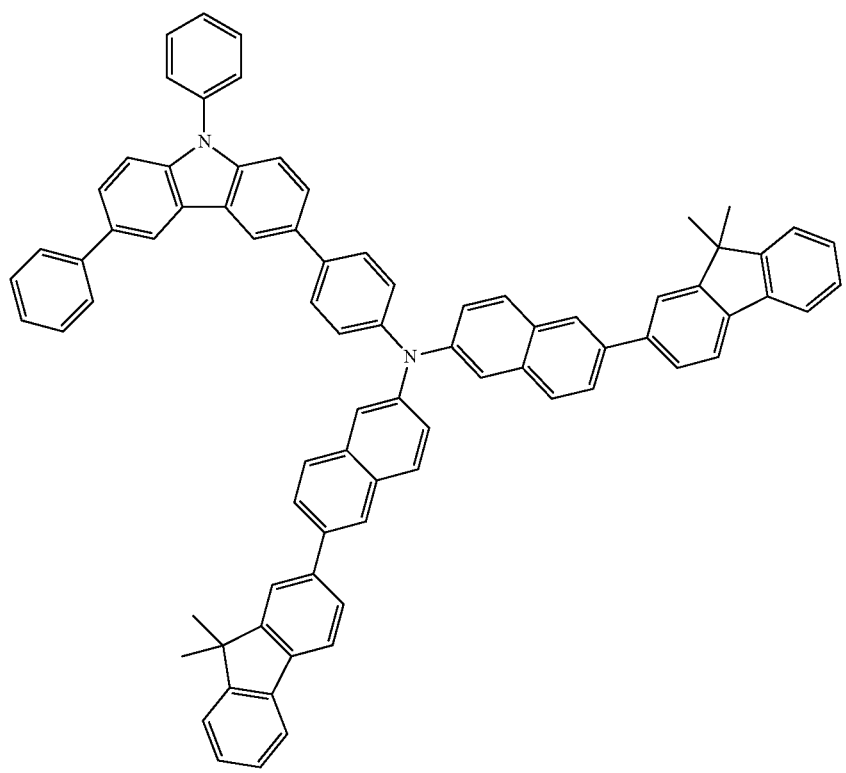

Structural Formula 78
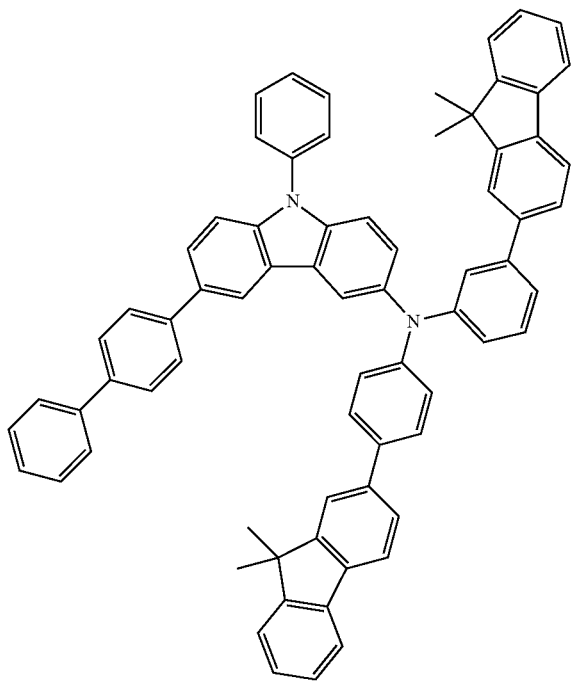
Structural Formula 79
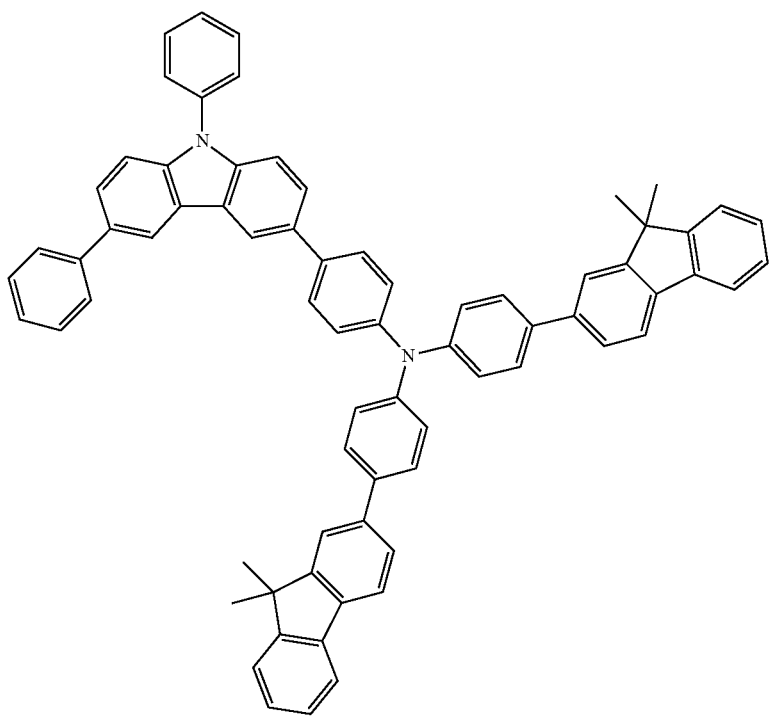

Structural Formula 80

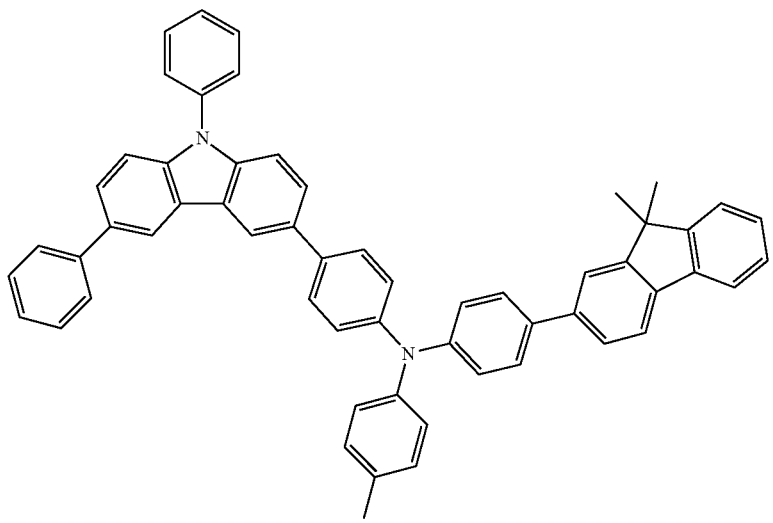

A second aspect of the present invention relates to an organic electronic device which comprises a first electrode, a second electrode, and one or more organic material layers that are disposed between the first electrode and the second electrode, wherein one or more layers of the organic material layers comprise the compound that is represented by Formula 1.

The compound that is represented by Formula 1 may be formed to the organic material layer by using a vacuum deposition method and a solution coating method when the organic light emitting device is manufactured. In connection with this, illustrative, but non-limiting, examples of the solution coating process comprise a spin coating process, a dip coating process, an inkjet printing process, a screen printing process, a spray process, and a roll coating process.

The organic electronic device of the present invention may be produced using known materials through a known process, modified only in that at least one layer of organic material layer(s) comprise the compound of the present invention, that is, the compound of Formula 1.

The organic material layer of the organic electronic device according to the present invention may have a single layer structure, or a multilayered structure in which two or more organic material layers are layered.

That is, in the organic electronic device, the organic material layer comprises at least one of a hole injection layer and a hole transport layer, and the hole injection layer and a hole transport layer comprise the compound represented by Formula 1.

In addition, the organic material layer comprises a light emitting layer, and the light emitting layer comprises the compound of Formula 1.

For example, the organic electronic device according to the present invention may have a structure that comprises a hole injection layer, a hole transport layer, a light emitting layer, an electron transport layer, and an electron injection layer as an organic material layer. However, the structure of the organic electronic device is not limited to this, but may comprise a smaller number of organic material layers.

In addition, the organic electronic device may be selected from the group consisting of an organic light emitting device, an organic phosphorescent device, an organic solar cell, an organic photoconductor (OPC), and an organic transistor.

The organic electronic device of the present invention may be produced, for example, by sequentially layering a first electrode, organic material layer(s), and a second electrode on a substrate. In connection with this, a physical vapor deposition (PVD) method, such as a sputtering method or an e-beam evaporation method, may be used, but the method is not limited to these.

MODE FOR INVENTION

The method for manufacturing the compound of Formula 1 and the manufacturing of an organic light emitting device using the same will be described in detail in Preparation Examples and Examples. However, the Preparation Examples and Examples are set forth to illustrate the present invention, but the scope of the present invention is not limited thereto.

PREPARATION EXAMPLE 1

Preparation of the Compound Represented by Structural Formula 1

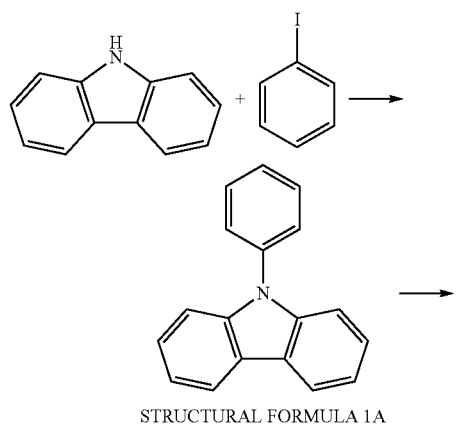

STRUCTURAL FORMULA 1A

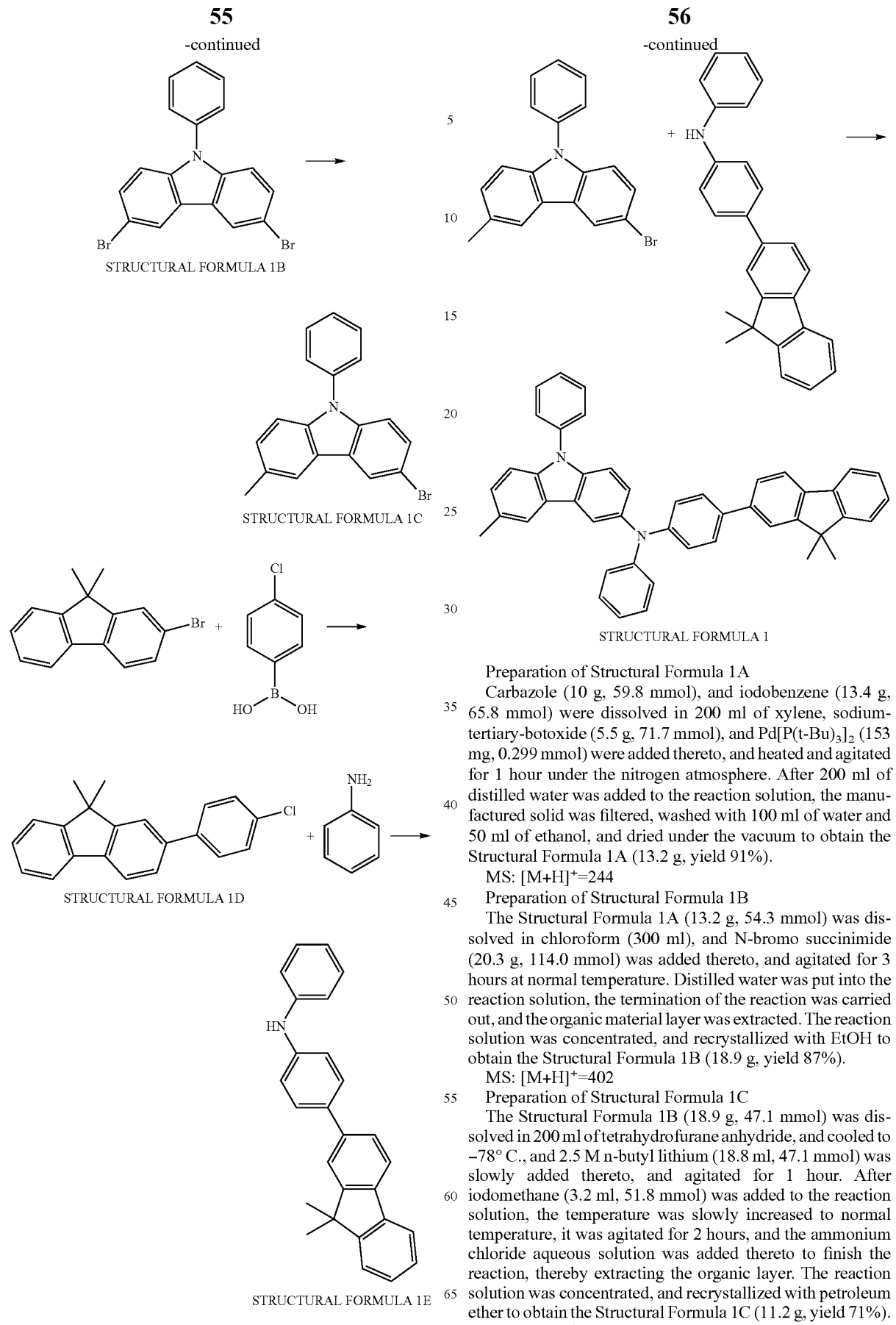

Preparation of Structural Formula 1A

Carbazole (10 g, 59.8 mmol), and iodobenzene (13.4 g, 65.8 mmol) were dissolved in 200 ml of xylene, sodium-tertiary-botoxide (5.5 g, 71.7 mmol), and Pd[P(t-Bu)$_3$]$_2$ (153 mg, 0.299 mmol) were added thereto, and heated and agitated for 1 hour under the nitrogen atmosphere. After 200 ml of distilled water was added to the reaction solution, the manufactured solid was filtered, washed with 100 ml of water and 50 ml of ethanol, and dried under the vacuum to obtain the Structural Formula 1A (13.2 g, yield 91%).

MS: [M+H]$^+$=244

Preparation of Structural Formula 1B

The Structural Formula 1A (13.2 g, 54.3 mmol) was dissolved in chloroform (300 ml), and N-bromo succinimide (20.3 g, 114.0 mmol) was added thereto, and agitated for 3 hours at normal temperature. Distilled water was put into the reaction solution, the termination of the reaction was carried out, and the organic material layer was extracted. The reaction solution was concentrated, and recrystallized with EtOH to obtain the Structural Formula 1B (18.9 g, yield 87%).

MS: [M+H]$^+$=402

Preparation of Structural Formula 1C

The Structural Formula 1B (18.9 g, 47.1 mmol) was dissolved in 200 ml of tetrahydrofurane anhydride, and cooled to −78° C., and 2.5 M n-butyl lithium (18.8 ml, 47.1 mmol) was slowly added thereto, and agitated for 1 hour. After iodomethane (3.2 ml, 51.8 mmol) was added to the reaction solution, the temperature was slowly increased to normal temperature, it was agitated for 2 hours, and the ammonium chloride aqueous solution was added thereto to finish the reaction, thereby extracting the organic layer. The reaction solution was concentrated, and recrystallized with petroleum ether to obtain the Structural Formula 1C (11.2 g, yield 71%).

MS: [M+H]$^+$=337

Preparation of Structural Formula 1D 2-bromo-9,9-dimethylfluorene (30 g, 109.8 mmol), and 4-chlorobenzene boronic acid (20.6 g, 131.8 mmol) were dissolved in 200 ml of tetrahydrofurane, 150 ml of 2M potassium carbonate aqueous solution and Pd(PPh$_3$)$_4$ (1.3 g, 1.1 mmol) were added thereto, and heated and agitated for 5 hours. After the temperature was lowered to normal temperature, the organic layer was extracted, concentrated, and recrystallized with ethanol to obtain the Structural Formula 1D (29.4 g, yield 88%).

MS: $[M+H]^+$=30

Preparation of Structural Formula 1E

Structural Formula 1D (10 g, 32.8 mmol), and aniline (2.8 ml, 31.2 mmol) were dissolved in 100 ml of toluene, sodium-tertiary-botoxide (3.5 g, 36.1 mmol), and Pd[P(t-Bu)$_3$]$_2$ (84 mg, 0.164 mmol) were added thereto, and heated and agitated for 1 hour under the nitrogen atmosphere. The organic layer in which 100 ml of distilled water was added to the reaction solution was extracted and purified through the column to obtain the Structural Formula 1E (8.2 g, yield 69%).

MS: $[M+H]^+$=362

Preparation of Structural Formula 1

Structural Formula 1C (11.2 g, 33.3 mmol), and Structural Formula 1E (11.4 g, 31.6 mmol) were dissolved in 150 ml of xylene, sodium-tertiary-botoxide (3.6 g, 37.9 mmol), and Pd[P(t-Bu)$_3$]$_2$ (81 mg, 0.158 mmol) were added thereto, and heated and agitated for 1 hour under the nitrogen atmosphere. The organic layer in which 100 ml of distilled water was added to the reaction solution was extracted, concentrated, and recrystallized with ethanol to obtain the Structural Formula 1 (14.9 g, yield 76%).

MS: $[M+H]^+$=618

PREPARATION EXAMPLE 2

Preparation of the Compound Represented by Structural Formula 14

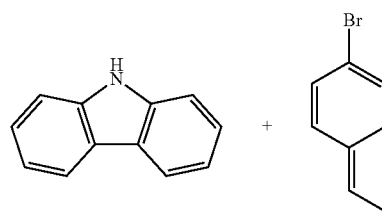

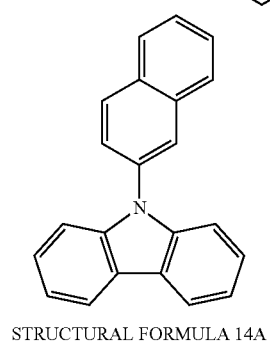

STRUCTURAL FORMULA 14A

-continued

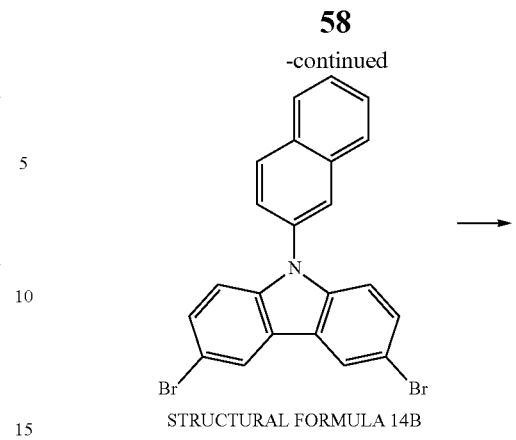

STRUCTURAL FORMULA 14B

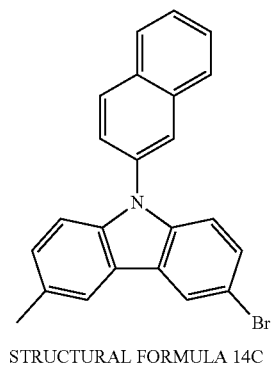

STRUCTURAL FORMULA 14C

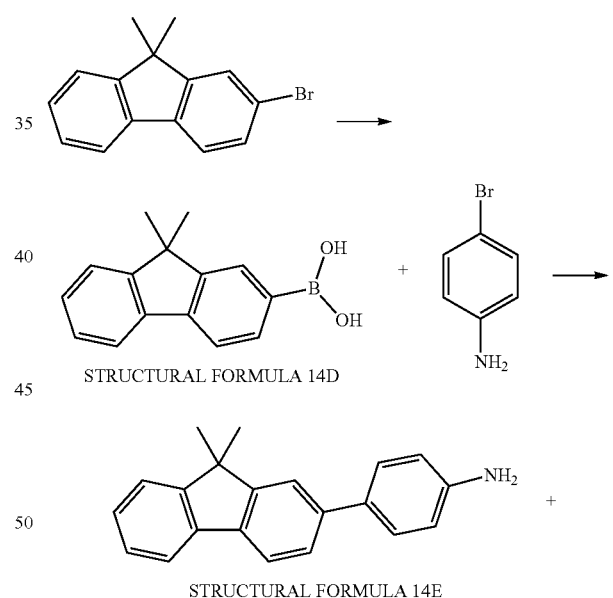

STRUCTURAL FORMULA 14D

STRUCTURAL FORMULA 14E

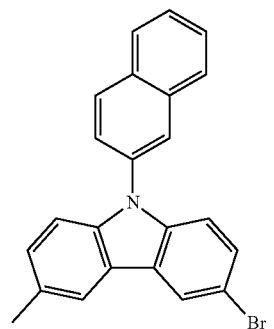

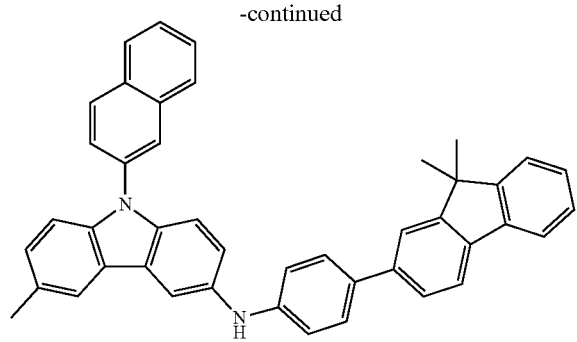

STRUCTURAL FORMULA 14F

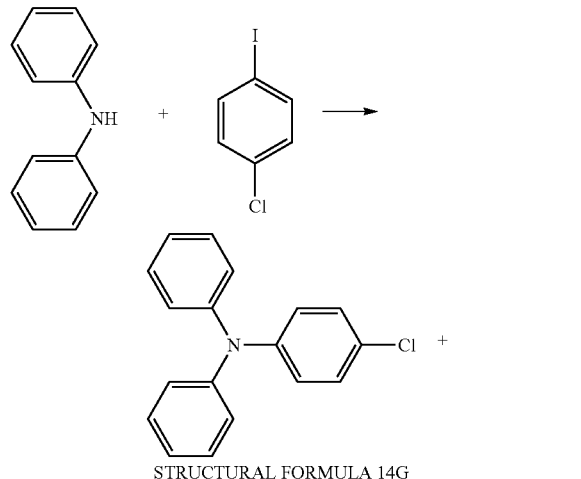

STRUCTURAL FORMULA 14G

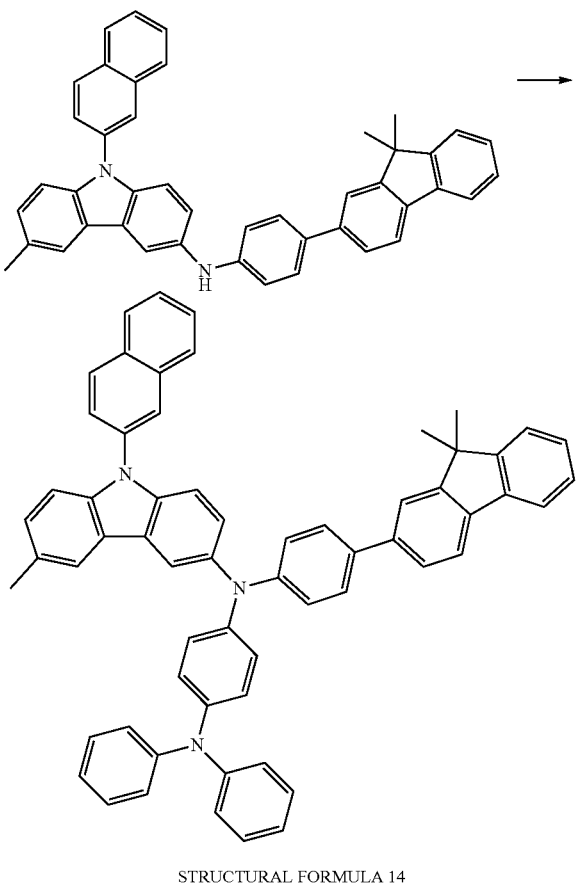

STRUCTURAL FORMULA 14

Preparation of Structural Formula 14A

The Structural Formula 14A was obtained by using the same method as the preparation method of the Structural Formula 1A, except that bromonaphthalene was used instead of iodobenzene.

MS: $[M+H]^+=294$

Preparation of Structural Formula 14B

The Structural Formula 14B was obtained by using the same method as the preparation method of the Structural Formula 1B, except that the Structural Formula 14A was used instead of the Structural Formula 1A.

MS: $[M+H]^+=452$

Preparation of Structural Formula 14C

The Structural Formula 14C was obtained by using the same method as the preparation method of the Structural Formula 1C, except that the Structural Formula 14B was used instead of the Structural Formula 1B.

MS: $[M+H]^+=387$

Preparation of Structural Formula 14D 2-bromo-9,9-dimethylfluorene (15 g, 54.9 mmol) was dissolved in 150 ml of tetrahydrofurane anhydride, and cooled to −78° C., and 2.5 M n-butyl lithium (24.2 ml, 60.4 mmol) was slowly added thereto, and agitated for 1 hour. Trimethyl borate (9.2 ml, 82.4 mmol) was added to the reaction solution, and agitated for 30 min, 6N HCl 50 ml was added thereto, the temperature was increased to normal temperature, and it was agitated for 1 hour. The organic layer was extracted, concentrated, and recrystallized with n-hexane to obtain the Structural Formula 14D (10 g, yield 77%).

MS: $[M+H]^+=239$

Preparation of Structural Formula 14E

The Structural Formula 14D (10 g, 42.0 mmol), and 4-bromoaniline (6.9 g, 39.9 mmol) were dissolved in 100 ml of tetrahydrofurane, 100 ml of 2M potassium carbonate aqueous solution and $Pd(PPh_3)_4$ (485 mg, 0.42 mmol) were added thereto, and heated and agitated for 5 hours. After the temperature was lowered to normal temperature, the organic layer was extracted, concentrated, and recrystallized with ethanol to obtain the Structural Formula 14E (10.4 g, yield 91%).

MS: $[M+H]^+=286$

Preparation of Structural Formula 14F

Structural Formula 14E (10.4 g, 36.4 mmol), and Structural Formula 14C (14.1 g, 36.4 mmol) were dissolved in 100 ml of xylene, sodium-tertiary-botoxide (4.2 g, 43.7 mmol), and $Pd[P(t-Bu)_3]_2$ (93 mg, 0.182 mmol) were added thereto, and heated and agitated for 1 hour under the nitrogen atmosphere. The organic layer in which 100 ml of distilled water was added to the reaction solution was extracted and purified through the column to obtain the Structural Formula 14F (16.6 g, yield 77%).

MS: $[M+H]^+=592$

Preparation of Structural Formula 14G

Diphenylamine (15 g, 88.6 mmol), 4-chloroiodobenzene (21.1 g, 88.6 mmol), cupper iodide (844 mg, 4.4 mmol), N,N'-dimethylethylenediamine (0.943 ml, 8.8 mmol), and potassium carbonate (14.7 g, 106.3 mmol) were added to 150 ml of xylene, and heated and agitated for 24 hours. After the temperature was lowered to normal temperature, the reaction solution was filtered by the cellite pad, concentrated, and recrystallized with methanol to obtain the Structural Formula 14G (20 g, yield 81%).

MS: $[M+H]^+=280$

Preparation of Structural Formula 14

Structural Formula 14F (10 g, 16.9 mmol), and Structural Formula 14 g (5.2 g, 18.6 mmol) were dissolved in 100 ml of xylene, sodium-tertiary-botoxide (1.9 g, 20.3 mmol), and Pd[P(t-Bu)$_3$]$_2$ (43 mg, 0.085 mmol) were added thereto, and heated and agitated for 1 hour under the nitrogen atmosphere. The organic layer in which 100 ml of distilled water was added to the reaction solution was extracted, concentrated, and recrystallized with methanol to obtain the Structural Formula 14 (11.1 g, yield 79%).

MS: [M+H]$^+$=835

PREPARATION EXAMPLE 3

Preparation of the Compound Represented by Structural Formula 18

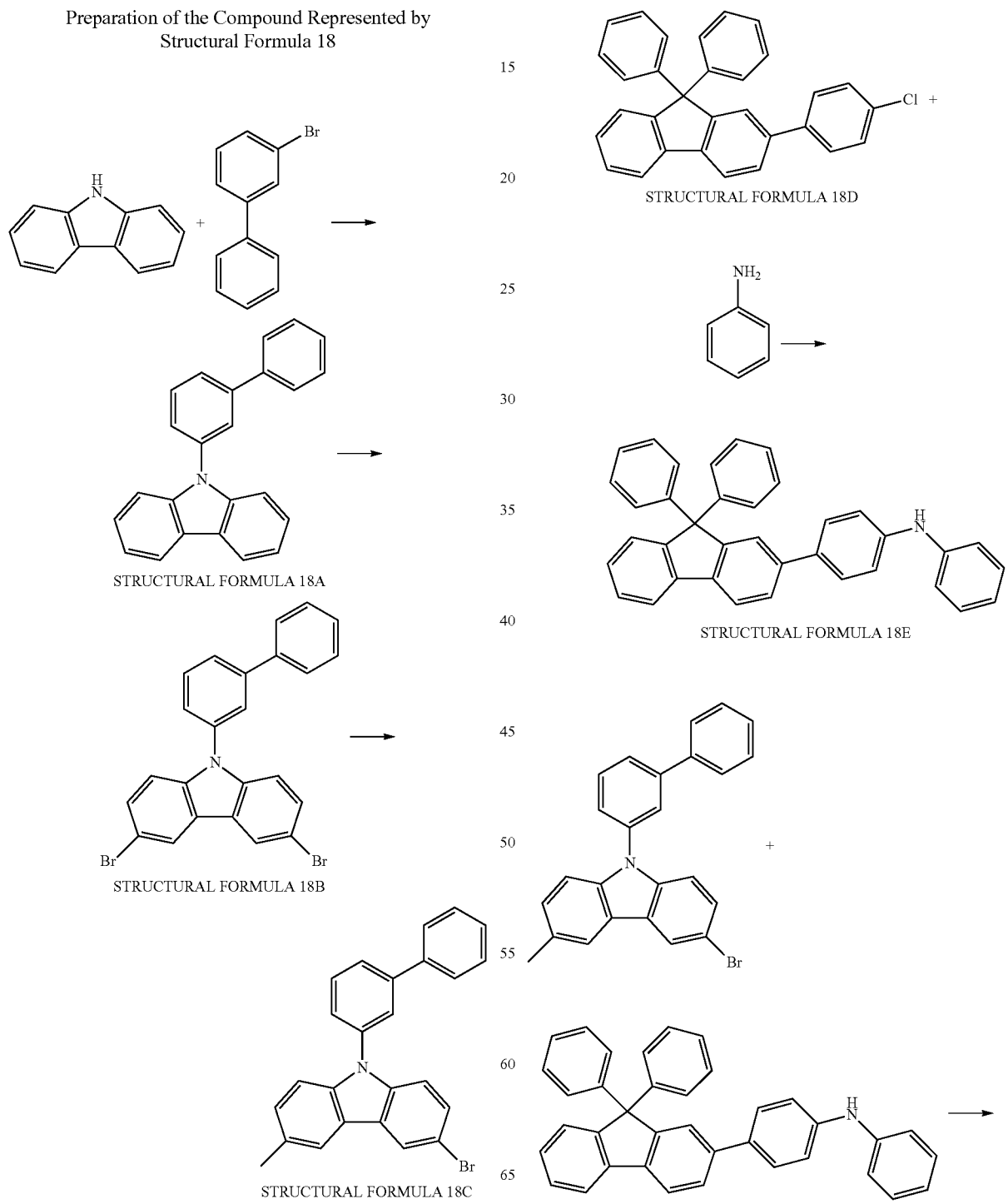

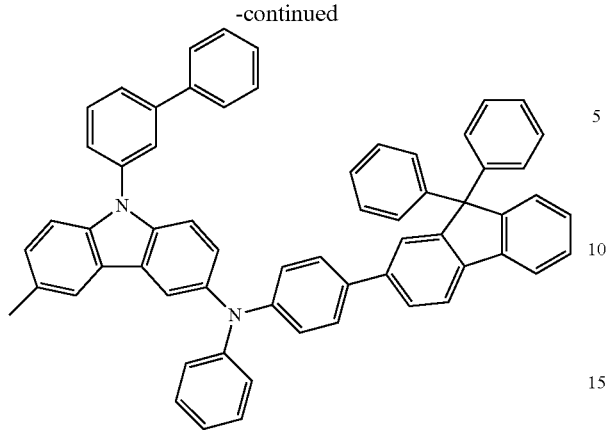

STRUCTURAL FORMULA 18

Preparation of Structural Formula 18A

The Structural Formula 18A was obtained by using the same method as the preparation method of the Structural Formula 1A, except that 3-bromobiphenyl was used instead of iodobenzene.

MS: $[M+H]^+=835$

Preparation of Structural Formula 18B

The Structural Formula 18B was obtained by using the same method as the preparation method of the Structural Formula 1B, except that the Structural Formula 18A was used instead of the Structural Formula 1A.

MS: $[M+H]^+=478$

Preparation of Structural Formula 18C

The Structural Formula 18C was obtained by using the same method as the preparation method of the Structural Formula 1C, except that the Structural Formula 18B was used instead of the Structural Formula 1B.

MS: $[M+H]^+=413$

Preparation of Structural Formula 18D 2-bromo-9,9-diphenylfluorene (15 g, 37.8 mmol), and 4-chlorobenzene boronic acid (6.5 g, 41.5 mmol) were dissolved in 150 ml of tetrahydrofurane, 100 ml of 2M potassium carbonate aqueous solution and Pd(PPh$_3$)$_4$ (437 mg, 0.38 mmol) were added thereto, and heated and agitated for 5 hours. After the temperature was lowered to normal temperature, the organic layer was extracted, concentrated, and recrystallized with ethanol to obtain the Structural Formula 18D (11.9 g, yield 73%).

MS: $[M+H]^+=430$

Preparation of Structural Formula 18E

Structural Formula 18D (11.9 g, 27.7 mmol), and aniline (2.4 ml, 26.4 mmol) were dissolved in 100 ml of toluene, sodium-tertiary-botoxide (3.0 g, 31.7 mmol), and Pd[P(t-Bu)$_3$]$_2$ (67 mg, 0.132 mmol) were added thereto, and heated and agitated for 1 hour under the nitrogen atmosphere. The organic layer in which 100 ml of distilled water was added to the reaction solution was extracted, concentrated, and recrystallized with methanol to obtain the Structural Formula 18E (8.3 g, yield 65%).

MS: $[M+H]^+=486$

Preparation of Structural Formula 18

Structural Formula 18E (8.3 g, 17.1 mmol), and Structural Formula 18C (7.0 g, 17.1 mmol) were dissolved in 100 ml of xylene, sodium-tertiary-botoxide (2.0 g, 20.5 mmol), and Pd[P(t-Bu)$_3$]$_2$ (44 mg, 0.085 mmol) were added thereto, and heated and agitated for 1 hour under the nitrogen atmosphere. The organic layer in which 100 ml of distilled water was added to the reaction solution was extracted, concentrated, and purified through column to obtain the Structural Formula 18 (10.5 g, yield 75%).

MS: $[M+H]^+=818$

PREPARATION EXAMPLE 4

Preparation of the Compound Represented by Structural Formula 21

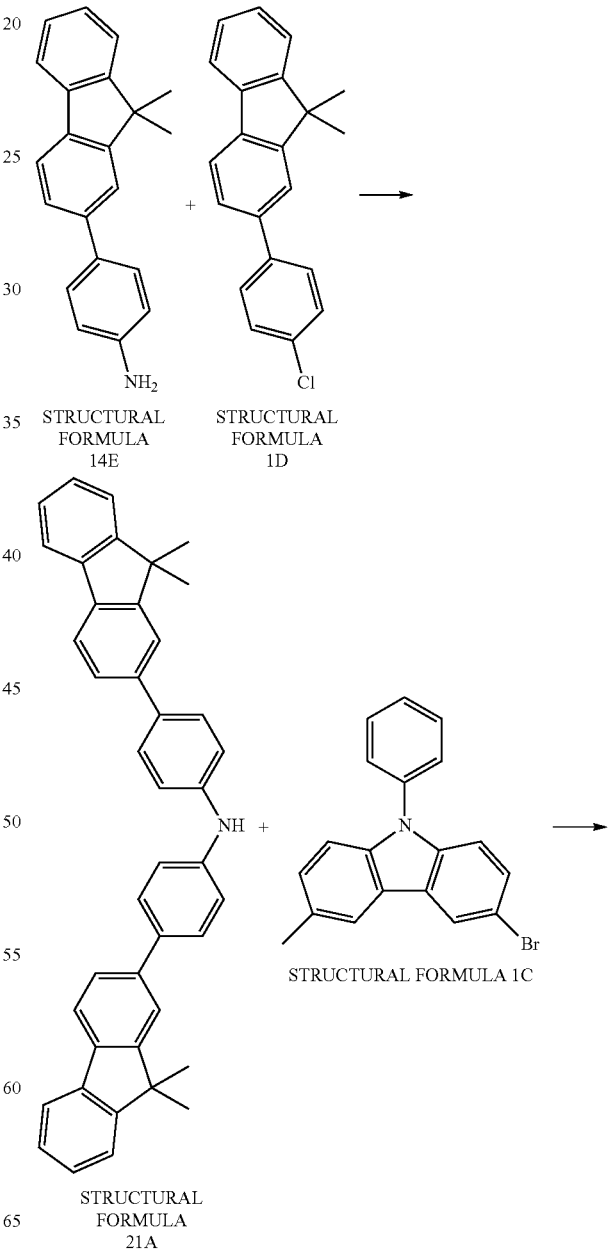

STRUCTURAL FORMULA 14E

STRUCTURAL FORMULA 1D

STRUCTURAL FORMULA 1C

STRUCTURAL FORMULA 21A

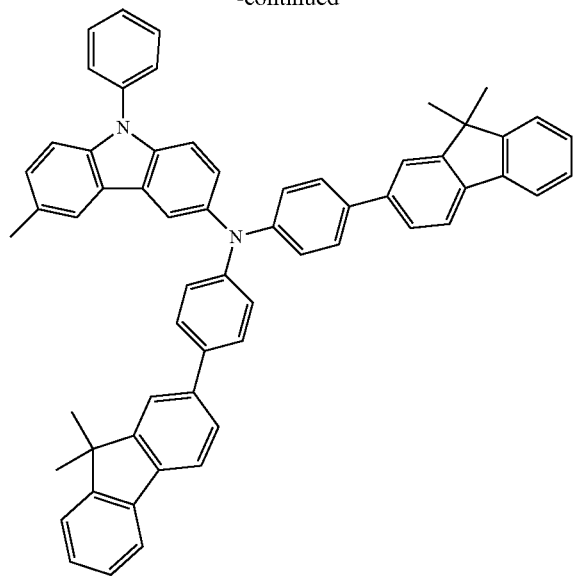

STRUCTURAL FORMULA 21

Preparation of Structural Formula 21A

Structural Formula 14E (10 g, 35.0 mmol), and Structural Formula 1D (10.7 g, 35.0 mmol) were dissolved in 150 ml of toluene, sodium-tertiary-botoxide (4.0 g, 42.0 mmol), and Pd[P(t-Bu)$_3$]$_2$ (89 mg, 0.175 mmol) were added thereto, and heated and agitated for 1 hour under the nitrogen atmosphere. The organic layer in which 100 ml of distilled water was added to the reaction solution was extracted, concentrated, and recrystallized with ethanol to obtain the Structural Formula 21A (14.7 g, yield 76%).

MS: [M+H]$^+$=554

Preparation of Structural Formula 21

Structural Formula 21A (14.7 g, 26.5 mmol), and Structural Formula 1C (8.9 g, 26.5 mmol) were dissolved in 150 ml of xylene, sodium-tertiary-botoxide (3.1 g, 31.8 mmol), and Pd[P(t-Bu)$_3$]$_2$ (68 mg, 0.133 mmol) were added thereto, and heated and agitated for 1 hour under the nitrogen atmosphere. The organic layer in which 100 ml of distilled water was added to the reaction solution was extracted, concentrated, and recrystallized with ethanol to obtain the Structural Formula 21 (16.3 g, yield 76%).

MS: [M+H]$^+$=809

PREPARATION EXAMPLE 5

Preparation of the Compound Represented by Structural Formula 27

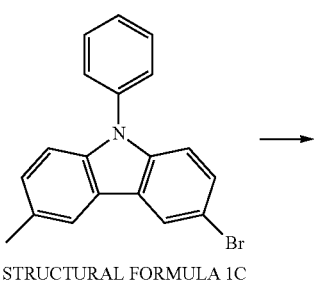

STRUCTURAL FORMULA 1C

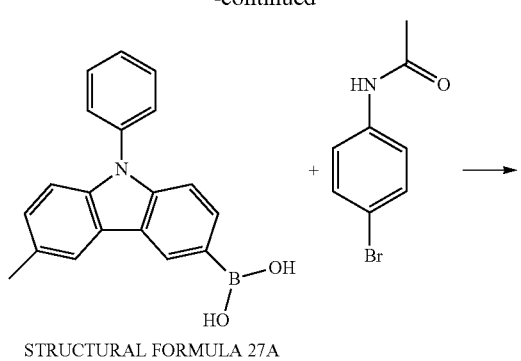

STRUCTURAL FORMULA 27A

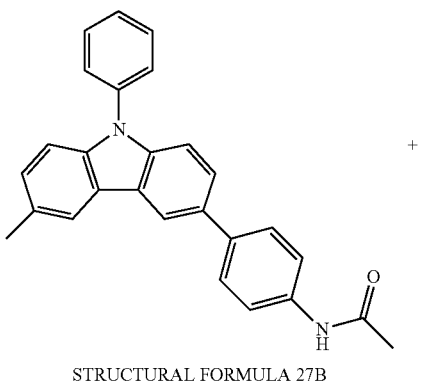

STRUCTURAL FORMULA 27B

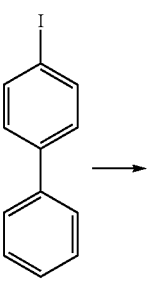

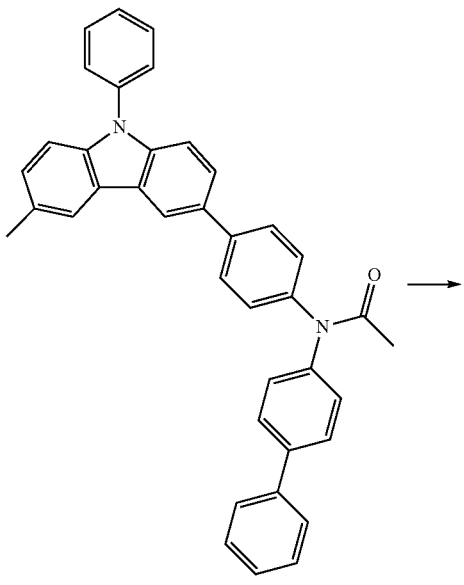

STRUCTURAL FORMULA 27C

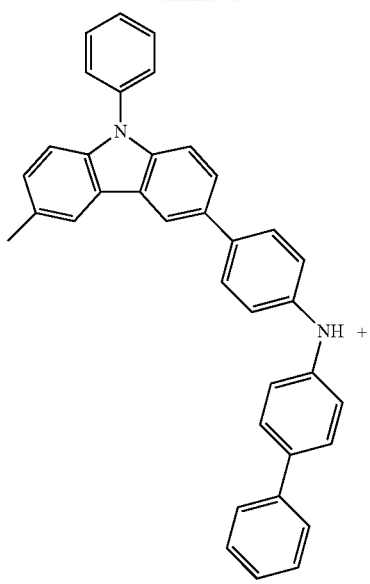

STRUCTURAL FORMULA 27D

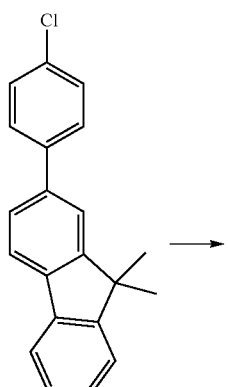

STRUCTURAL FORMULA 1D

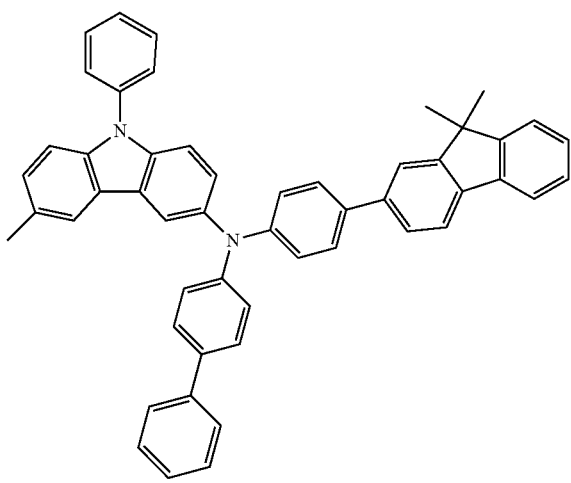

STRUCTURAL FORMULA 27

Preparation of Structural Formula 27A

The Structural Formula 27A was obtained by using the same method as the preparation method of the Structural Formula 14D, except that the Structural Formula 1C was used instead of 2-bromo-9,9-dimethylfluorene.

MS: $[M+H]^+=302$

Preparation of Structural Formula 27B

The Structural Formula 27A (15 g, 49.8 mmol), and 4-bromoaniline (10.1 g, 47.3 mmol) were dissolved in 100 ml of tetrahydrofurane, 100 ml of 2M potassium carbonate aqueous solution and Pd(PPh$_3$)$_4$ (575 mg, 0.50 mmol) were added thereto, and heated and agitated for 5 hours. After the temperature was lowered to normal temperature, the organic layer was extracted, concentrated, and recrystallized with ethanol to obtain the Structural Formula 27B (15.2 g, yield 78%).

MS: $[M+H]^+=391$

Preparation of Structural Formula 27C

Structural Formula 27B (15 g, 38.4 mmol), 4-iodobiphenyl (12.9 g, 46.1 mmol), cupper iodide (366 mg, 1.9 mmol), N,N'-dimethylethylenediamine (0.409 ml, 3.8 mmol), and potassium carbonate (6.4 g, 46.1 mmol) were added to 150 ml of xylene, and heated and agitated for 24 hours. After the temperature was lowered to normal temperature, the reaction solution was filtered by the cellite pad, concentrated, and recrystallized with methanol to obtain the Structural Formula 27C (16.9 g, yield 81%).

MS: $[M+H]^+=543$

Preparation of Structural Formula 27D

After Structural Formula 27C (16.9 g, 31.1 mmol) was dissolved in 50 ml of tetrahydrofurane and 50 ml of ethanol, an excessive amount of potassium hydroxide was put thereinto and agitated at normal temperature for 1 hour. After the reaction solution was concentrated, it was completely dissolved in 100 ml of chloroform, 100 ml of water was put thereinto, and it was agitated at normal temperature for 10 min. The organic layer was extracted, concentrated, and recrystallized with petroleum ether to obtain Structural Formula 27D (15 g, yield 96%).

MS: $[M+H]^+=501$

Preparation of Structural Formula 27

Structural Formula 27D (15 g, 30.0 mmol), and Structural Formula 1D (9.1 g, 30.0 mmol) were dissolved in 100 ml of xylene, sodium-tertiary-botoxide (3.5 g, 36.0 mmol), and Pd[P(t-Bu)$_3$]$_2$ (77 mg, 0.15 mmol) were added thereto, and heated and agitated for 1 hour under the nitrogen atmosphere. The organic layer in which 100 ml of distilled water was added to the reaction solution was extracted, concentrated, and purified through column to obtain the Structural Formula 27 (15.7 g, yield 68%).

MS: $[M+H]^+=770$

PREPARATION EXAMPLE 6
Preparation of the Compound Represented by Structural Formula 33
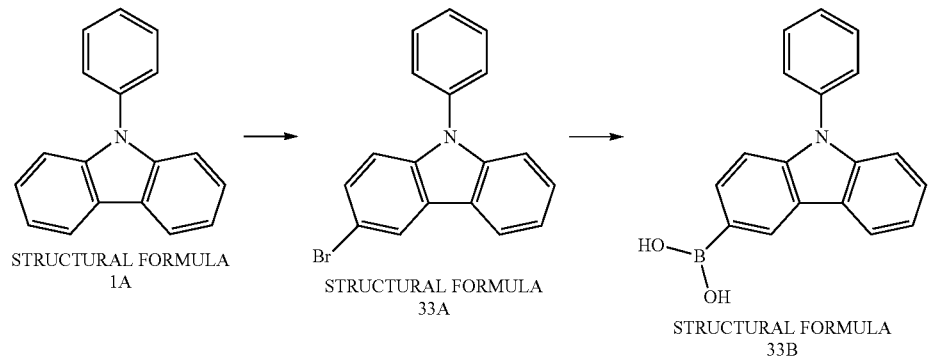
STRUCTURAL FORMULA 1A → STRUCTURAL FORMULA 33A → STRUCTURAL FORMULA 33B
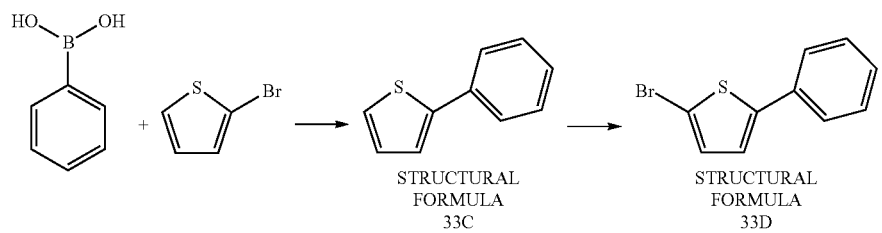
STRUCTURAL FORMULA 33C → STRUCTURAL FORMULA 33D
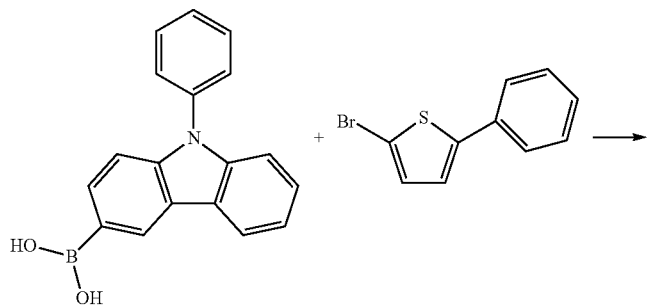
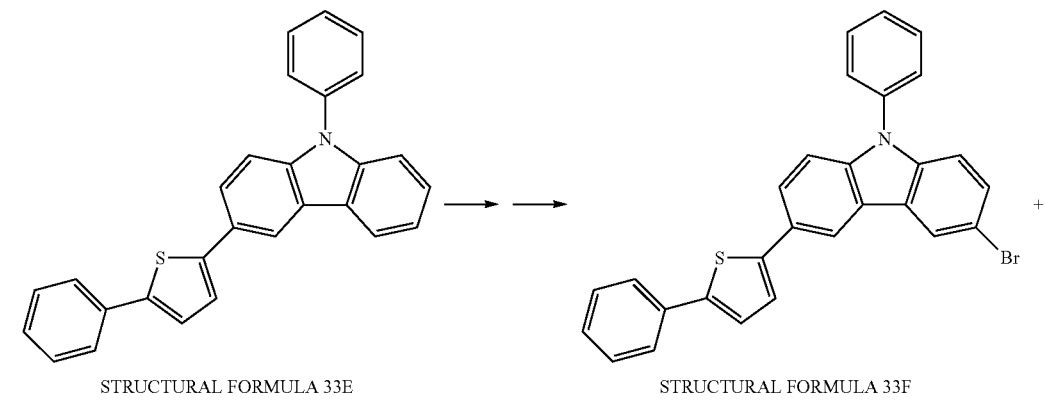
STRUCTURAL FORMULA 33E → STRUCTURAL FORMULA 33F

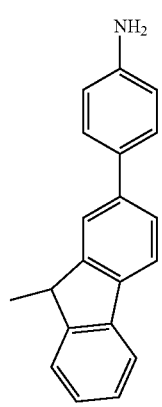

STRUCTURAL FORMULA 14E

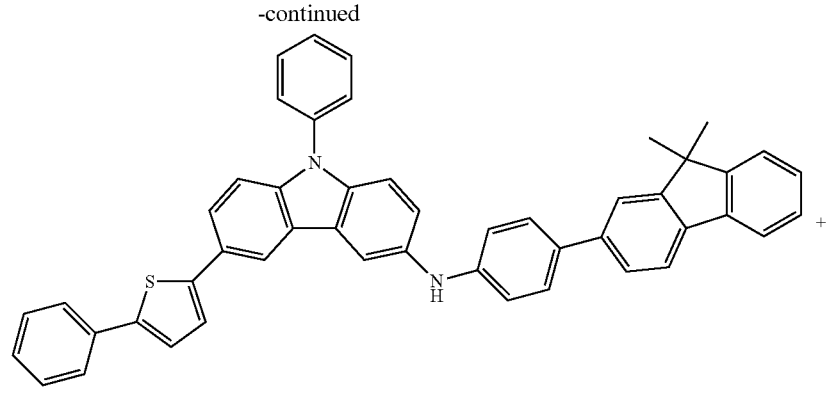

STRUCTURAL FORMULA 33G

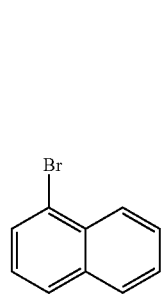

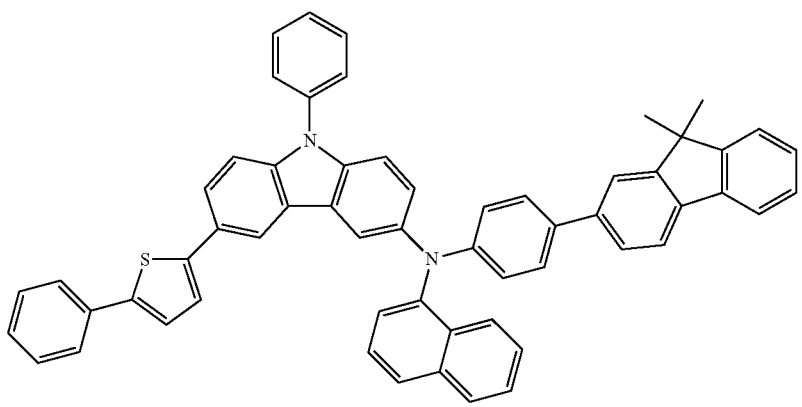

STRUCTURAL FORMULA 33

Preparation of Structural Formula 33A

The Structural Formula 1A (15 g, 61.6 mmol) was dissolved in chloroform (300 ml), and N-bromo succinimide (11.0 g, 61.6 mmol) was added thereto, and agitated for 1 hour at normal temperature. Distilled water was put into the reaction solution, the termination of the reaction was carried out, and the organic material layer was extracted. The reaction solution was concentrated, and recrystallized with n-hexane to obtain the Structural Formula 33A (17 g, yield 86%).

MS: $[M+H]^+=323$

Preparation of Structural Formula 33B

The Structural Formula 33B was obtained by using the same method as the preparation method of the Structural Formula 14D, except that the Structural Formula 1A was used instead of 2-bromo-9,9-dimethylfluorene.

MS: $[M+H]^+=288$

Preparation of Structural Formula 33C

Phenyl boronic acid (15 g, 123.0 mmol), 2-bromothiophene (11.3 ml, 116.9 mmol) were dissolved in 150 ml of tetrahydrofurane, 100 ml of 2M potassium carbonate aqueous solution and $Pd(PPh_3)_2$ (1.4 g, 1.2 mmol) were added thereto, and heated and agitated for 5 hours. After the temperature was lowered to normal temperature, the organic layer was extracted, concentrated, and recrystallized with n-hexane to obtain the Structural Formula 33C (17.4 g, yield 93%).

MS: $[M+H]^+=161$

Preparation of Structural Formula 33D

The Structural Formula 33D was obtained by using the same method as the preparation method of the Structural Formula 33A, except that the Structural Formula 33C was used instead of the Structural Formula 1A.

MS: $[M+H]^+=240$

Preparation of Structural Formula 33E

The Structural Formula 33E was obtained by using the same method as the preparation method of the Structural Formula 27B, except that the Structural Formula 33B was used instead of the Structural Formula 27A and the Structural Formula 33D was used instead of 4-bromoacetanilide.

MS: $[M+H]^+=402$

Preparation of Structural Formula 33F

The Structural Formula 33E (15 g, 37.4 mmol) was dissolved in chloroform (200 ml), and N-bromo succinimide (7.0 g, 39.2 mmol) was added thereto, and agitated for 1 hour at normal temperature. Distilled water was put into the reaction solution, the termination of the reaction was carried out, and the organic material layer was extracted. The reaction solution was concentrated, and recrystallized with ethanol to obtain the Structural Formula 33F (16 g, yield 89%).

MS: $[M+H]^+=481$

Preparation of Structural Formula 33G

The Structural Formula 33G was obtained by using the same method as the preparation method of the Structural Formula 14F, except that the Structural Formula 33F was used instead of the Structural Formula 14C.

MS: $[M+H]^+=686$

Preparation of Structural Formula 33

Structural Formula 33 g (10 g, 14.6 mmol), and 1-bromonaphthalene (2.2 ml, 16.1 mmol) were dissolved in 150 ml of xylene, sodium-tertiary-botoxide (1.7 g, 17.5 mmol), and Pd[P(t-Bu)$_3$]$_2$ (37 mg, 0.073 mmol) were added thereto, and heated and agitated for 1 hour under the nitrogen atmosphere. The organic layer in which 100 ml of distilled water was added to the reaction solution was extracted, concentrated, and purified through column to obtain the Structural Formula 33 (8.5 g, yield 72%).

MS: [M+H]$^+$=812

PREPARATION EXAMPLE 7

Preparation of the Compound Represented by Structural Formula 48

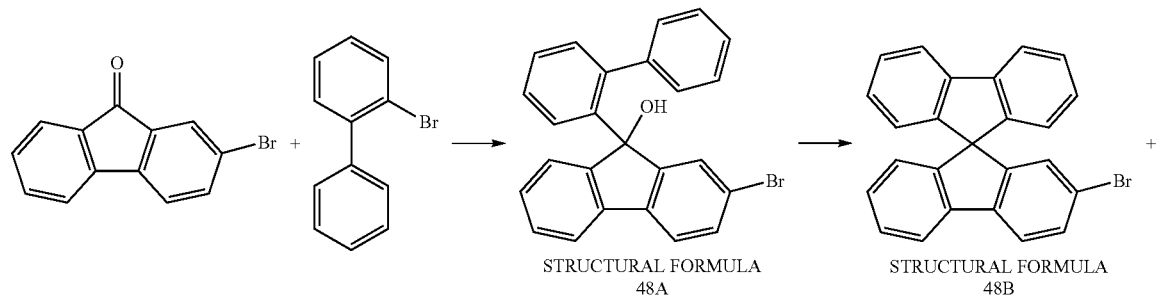

STRUCTURAL FORMULA 48A

STRUCTURAL FORMULA 48B

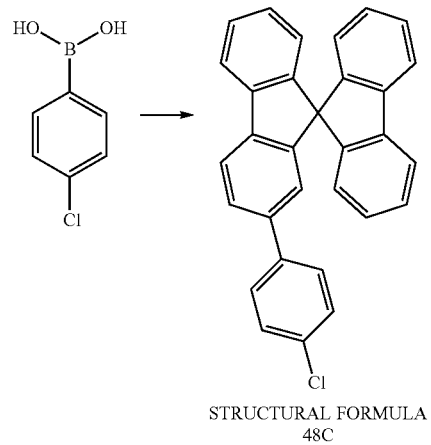

STRUCTURAL FORMULA 48C

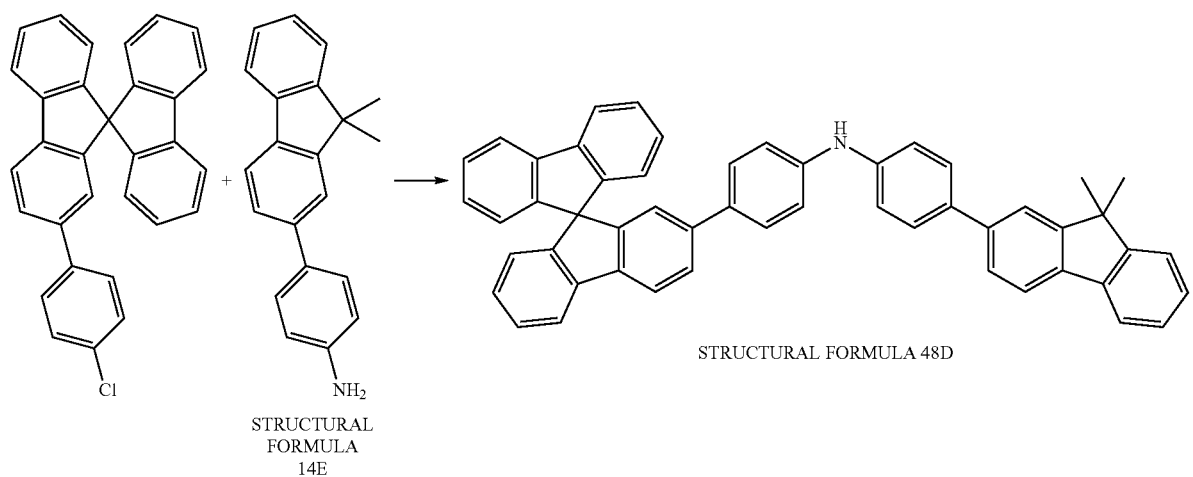

STRUCTURAL FORMULA 14E

STRUCTURAL FORMULA 48D

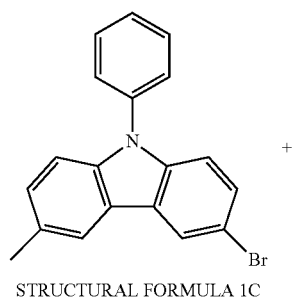

STRUCTURAL FORMULA 1C

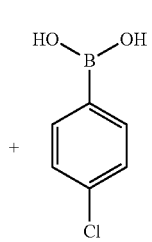

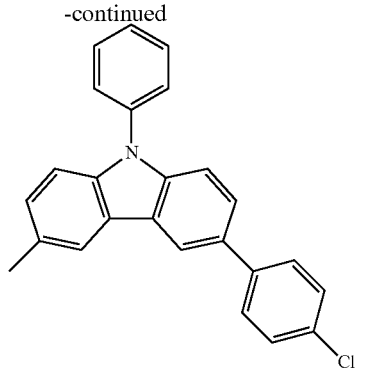

STRUCTURAL FORMULA 48E

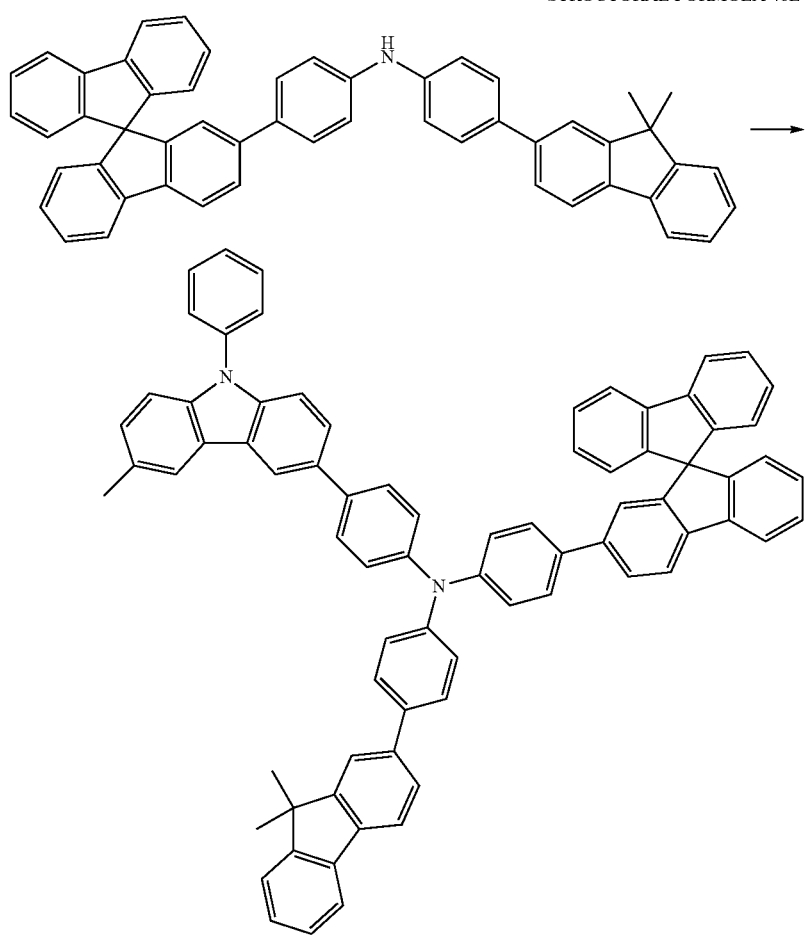

STRUCTURAL FORMULA 48

Preparation of Structural Formula 48A 2-bromobiphenyl (15 ml, 87.0 mmol) was dissolved in 250 ml of tetrahydrofurane anhydride, and cooled to −78° C., and 2.5 M n-butyl lithium (36.6 ml, 91.4 mmol) was slowly added thereto, and agitated for 1 hour. After 2-bromofluorenone (21.4 g, 82.7 mmol) was added to the reaction solution, the temperature was increased to normal temperature, and it was agitated for 3 hours. After the reaction was completed by putting the ammonium chloride aqueous solution, the organic layer was extracted, concentrated, and recrystallized with petroleum ether to obtain the Structural Formula 48A (27.3 g, yield 80%).

MS: $[M+H]^+$=413, 398

Preparation of Structural Formula 48B

Structural Formula 48A (27.3 g, 66.1 mmol) was added to 200 ml of glacial acetic acid, and heated, and 0.1 ml of sulfuric acid was added thereto, and heated and agitated for 1 hour. The solid that was generated after the temperature was lowered to normal temperature was filtered, washed with 300 ml of water, and 100 ml of ethanol, and dried to obtain Structural Formula 48B (25.4 g, yield 97%).

MS: $[M+H]^+$=396

Preparation of Structural Formula 48C 4-chlorobenzene boronic acid (10 g, 63.9 mmol), and Structural Formula 48B (24 g, 60.7 mmol) were dissolved in 150 ml of tetrahydrofurane, 100 ml of 2M potassium carbonate aqueous solution and Pd(PPh$_3$)$_4$ (701 mg, 0.607 mmol) were added thereto, and heated and agitated for 5 hours. After the temperature was lowered to normal temperature, the organic layer was extracted, concentrated, and recrystallized with ethanol to obtain the Structural Formula 48C (20.4 g, yield 79%).

MS: [M+H]$^+$=428

Preparation of Structural Formula 48D

The Structural Formula 48D was obtained by using the same method as the preparation method of the Structural Formula 14F, except that the Structural Formula 48C was used instead of the Structural Formula 14C.

MS: [M+H]$^+$=676

Preparation of Structural Formula 48E 4-chlorobenzene boronic acid (15 g, 95.9 mmol), and Structural Formula 1C (30.6 g, 91.1 mmol) were dissolved in 350 ml of tetrahydrofurane, 200 ml of 2M potassium carbonate aqueous solution and Pd(PPh$_3$)$_4$ (1.1 g, 0.911 mmol) were added thereto, and heated and agitated for 5 hours. After the temperature was lowered to normal temperature, the organic layer was extracted, concentrated, and recrystallized with ethanol to obtain the Structural Formula 48E (25.6 g, yield 76%).

MS: [M+H]$^+$=368

Preparation of Structural Formula 48

The Structural Formula 48D (15 g, 22.2 mmol), and the Structural Formula 48E (8.2 g, 22.2 mmol) were dissolved in 200 ml of xylene, sodium-tertiary-botoxide (2.6 g, 26.6 mmol), and Pd[P(t-Bu)$_3$]$_2$ (57 mg, 0.111 mmol) were added thereto, and heated and agitated for 1 hour under the nitrogen atmosphere. The organic layer in which 100 ml of distilled water was added to the reaction solution was extracted, concentrated, and purified through column to obtain the Structural Formula 48 (16.1 g, yield 72%).

MS: [M+H]$^+$=1008

PREPARATION EXAMPLE 8

Preparation of the Compound Represented by Structural Formula 56

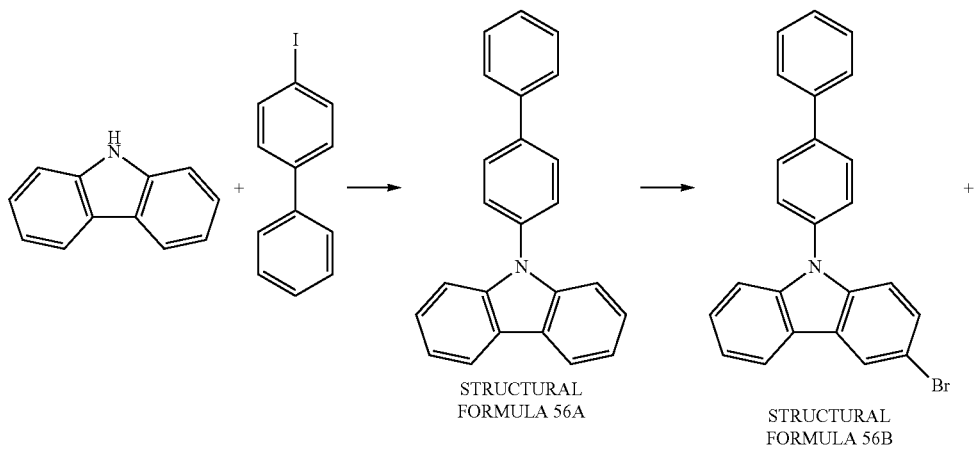

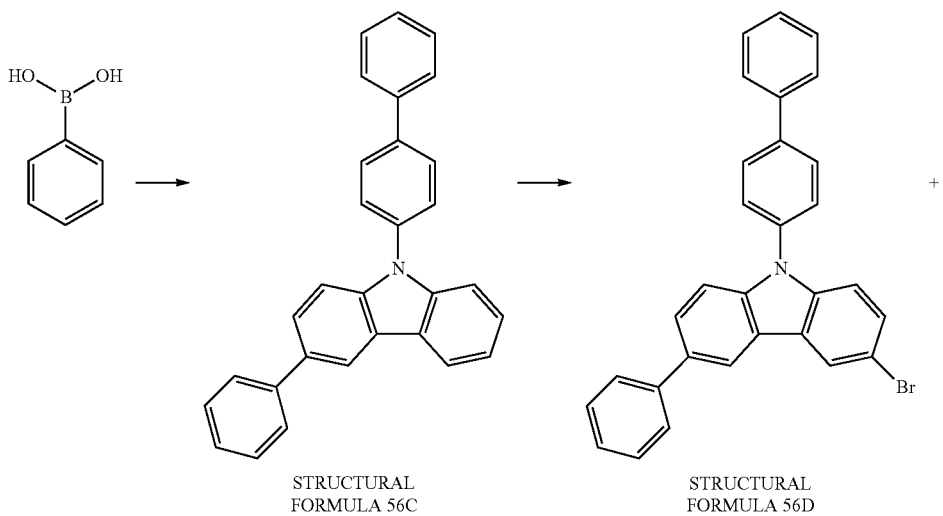

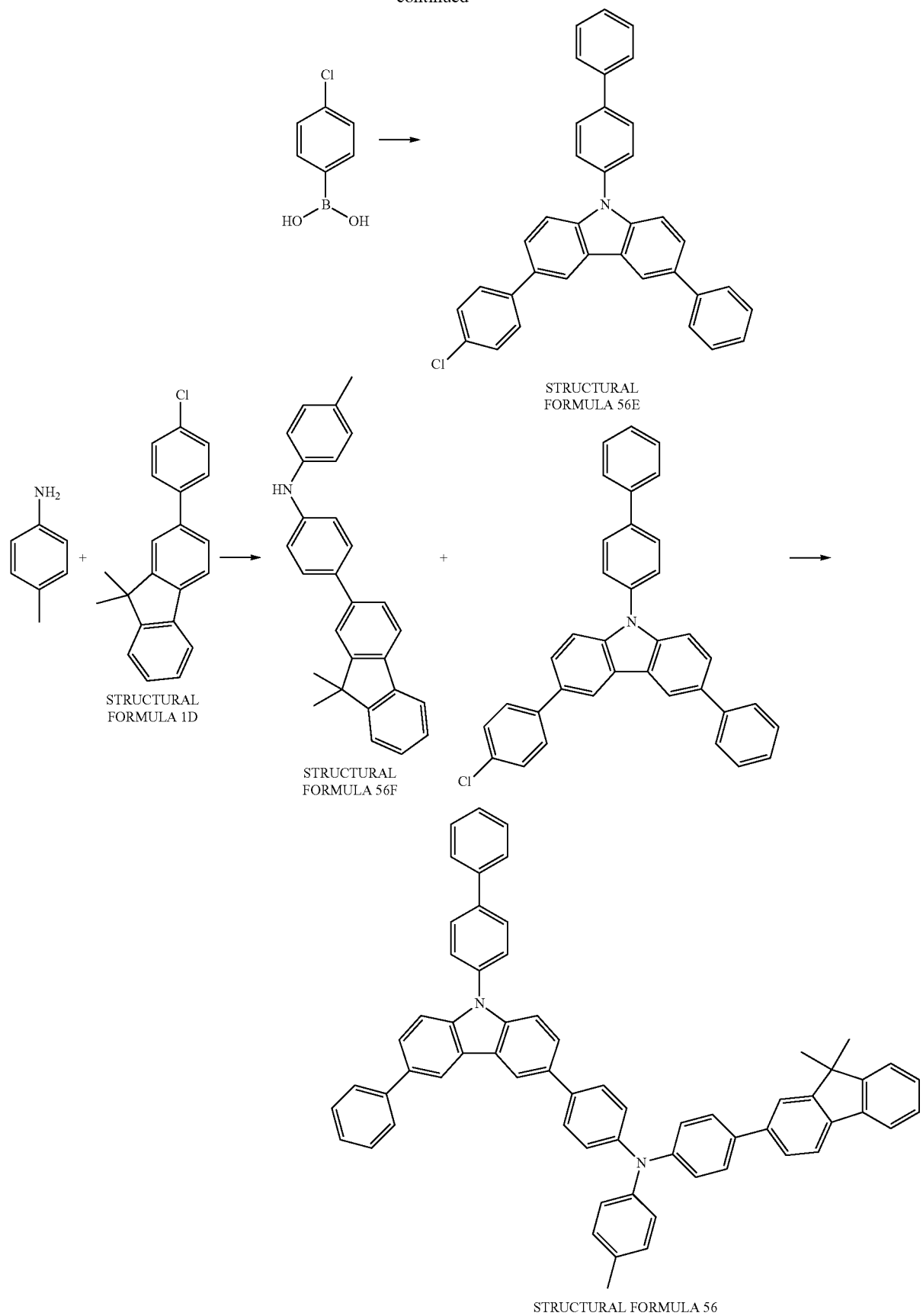

Preparation of Structural Formula 56A

The Structural Formula 56A was obtained by using the same method as the preparation method of the Structural Formula 1A, except that iodobiphenyl was used instead of iodobenzene.

MS: $[M+H]^+=320$

Preparation of Structural Formula 56B

The Structural Formula 56B was obtained by using the same method as the preparation method of the Structural Formula 33A, except that the Structural Formula 56A was used instead of the Structural Formula 1A.

MS: $[M+H]^+=399$

Preparation of Structural Formula 56C

The Structural Formula 56C was obtained by using the same method as the preparation method of the Structural Formula 33C, except that the Structural Formula 56B was used instead of 2-bromothiophene.

MS: $[M+H]^+=396$

Preparation of Structural Formula 56D

The Structural Formula 56D was obtained by using the same method as the preparation method of the Structural Formula 33A, except that the Structural Formula 56C was used instead of the Structural Formula 1A.

MS: $[M+H]^+=475$

Preparation of Structural Formula 56E

The Structural Formula 56E was obtained by using the same method as the preparation method of the Structural Formula 1D, except that the Structural Formula 56D was used instead of 2-bromo-9,9-dimethylfluorene.

MS: $[M+H]^+=507$

Preparation of Structural Formula 56F

Structural Formula 1D (10 g, 32.8 mmol), and p-toluidine (3.6 ml, 32.8 mmol) were dissolved in 200 ml of toluene, sodium-tertiary-botoxide (3.8 g, 39.4 mmol), and Pd[P(t-Bu)$_3$]$_2$ (84 mg, 0.164 mmol) were added thereto, and heated and agitated for 1 hour under the nitrogen atmosphere. The organic layer in which 100 ml of distilled water was added to the reaction solution was extracted, concentrated, and recrystallized with petroleum ether to obtain the Structural Formula 56F (9.1 g, yield 74%).

MS: $[M+H]^+=376$

Preparation of Structural Formula 56

Structural Formula 56E (12.3 g, 24.2 mmol), and Structural Formula 56F (9.1 g, 24.2 mmol) were dissolved in 200 ml of xylene, sodium-tertiary-botoxide (2.8 g, 29.0 mmol), and Pd[P(t-Bu)$_3$]$_2$ (62 mg, 0.121 mmol) were added thereto, and heated and agitated for 1 hour under the nitrogen atmosphere. The organic layer in which 200 ml of distilled water was added to the reaction solution was extracted, concentrated, and purified through column to obtain the Structural Formula 56 (15.0 g, yield 74%).

MS: $[M+H]^+=846$

PREPARATION EXAMPLE 9

Preparation of the Compound Represented by Structural Formula 59

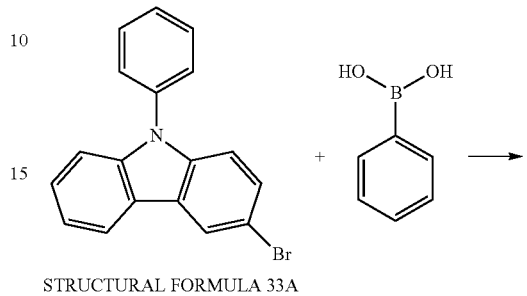

STRUCTURAL FORMULA 33A

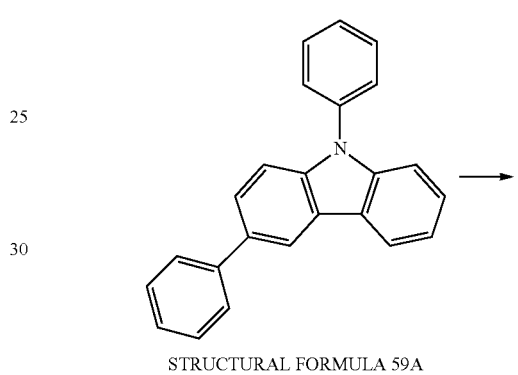

STRUCTURAL FORMULA 59A

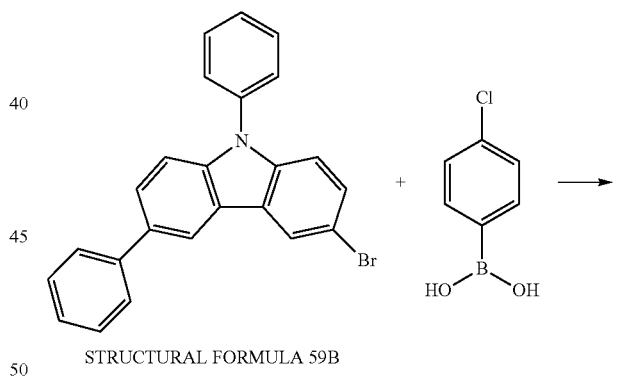

STRUCTURAL FORMULA 59B

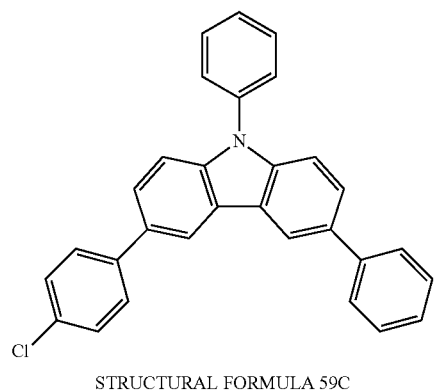

STRUCTURAL FORMULA 59C

-continued

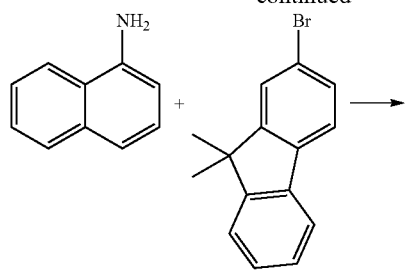

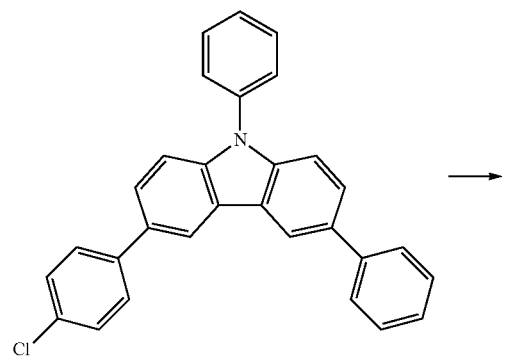

STRUCTURAL FORMULA 59D

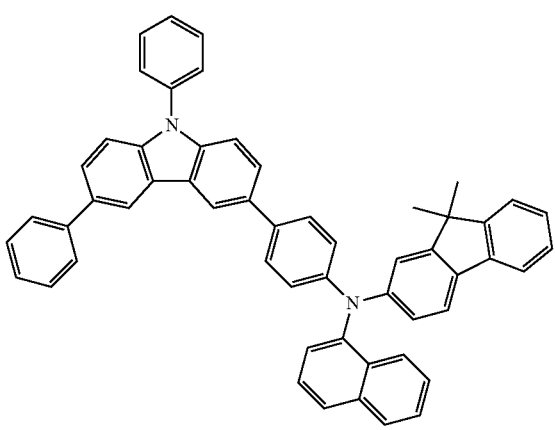

STRUCTURAL FORMULA 59

Preparation of Structural Formula 59A

The Structural Formula 51A was obtained by using the same method as the preparation method of the Structural Formula 33C, except that the Structural Formula 33A was used instead of 2-bromothiophene.

MS: $[M+H]^+=320$

Preparation of Structural Formula 59B

The Structural Formula 59B was obtained by using the same method as the preparation method of the Structural Formula 33A, except that the Structural Formula 59A was used instead of the Structural Formula 1A.

MS: $[M+H]^+=399$

Preparation of Structural Formula 59C

The Structural Formula 59C was obtained by using the same method as the preparation method of the Structural Formula 48E, except that the Structural Formula 59B was used instead of the Structural Formula 1C.

MS: $[M+H]^+=431$

Preparation of Structural Formula 59D 1-aminonaphthalene (15 g, 104.8 mmol), and 2-bromo-9,9-dimethylfluorene (28.6 g, 104.8 mmol) were dissolved in 200 ml of toluene, sodium-tertiary-botoxide (12.1 g, 125.8 mmol), and Pd[P(t-Bu)$_3$]$_2$ (268 mg, 0.524 mmol) were added thereto, and heated and agitated for 1 hour under the nitrogen atmosphere. The organic layer in which 200 ml of distilled water was added to the reaction solution was extracted, concentrated, and purified through column to obtain the Structural Formula 59D (29.5 g, yield 84%).

MS: $[M+H]^+=336$

Preparation of Structural Formula 59

Structural Formula 59C (10 g, 23.3 mmol), and Structural Formula 59D (7.8 g, 23.3 mmol) were dissolved in 150 ml of xylene, sodium-tertiary-botoxide (2.7 g, 28.0 mmol), and Pd[P(t-Bu)$_3$]$_2$ (60 mg, 0.117 mmol) were added thereto, and heated and agitated for 1 hour under the nitrogen atmosphere. The organic layer in which 150 ml of distilled water was added to the reaction solution was extracted, concentrated, and purified through column to obtain the Structural Formula 59 (12.4 g, yield 73%).

MS: $[M+H]^+=730$

PREPARATION EXAMPLE 10
Preparation of the Compound Represented by Structural Formula 75
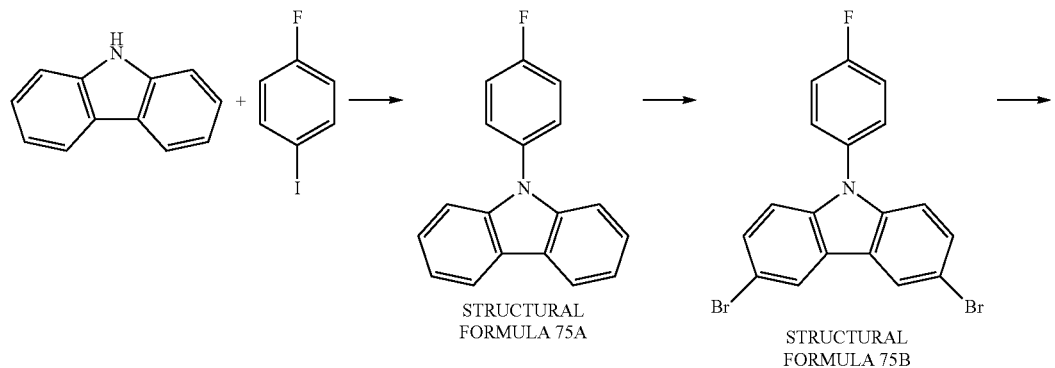
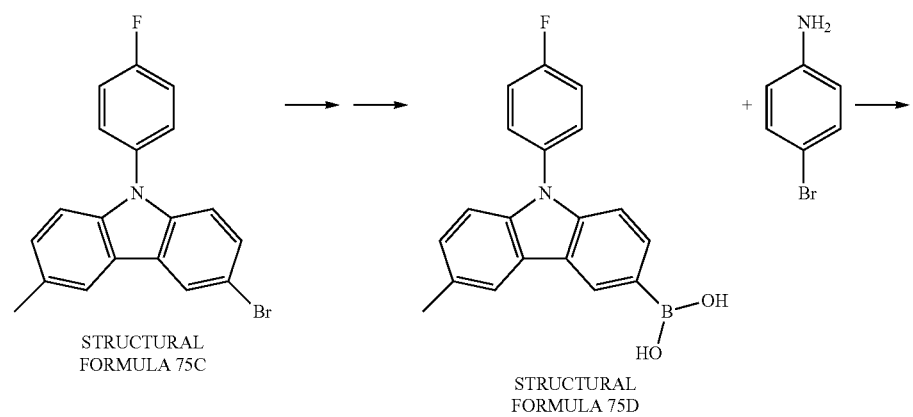
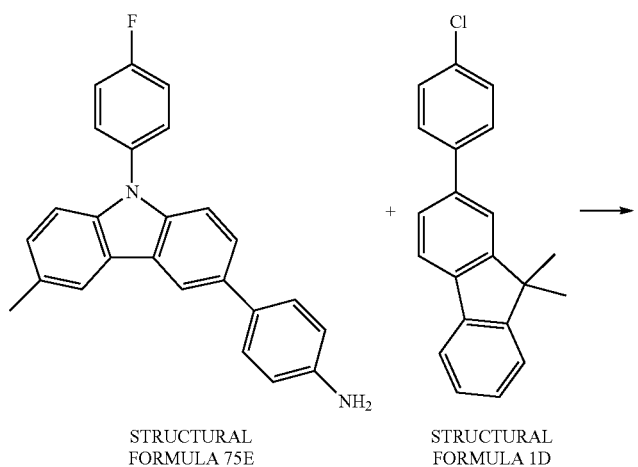

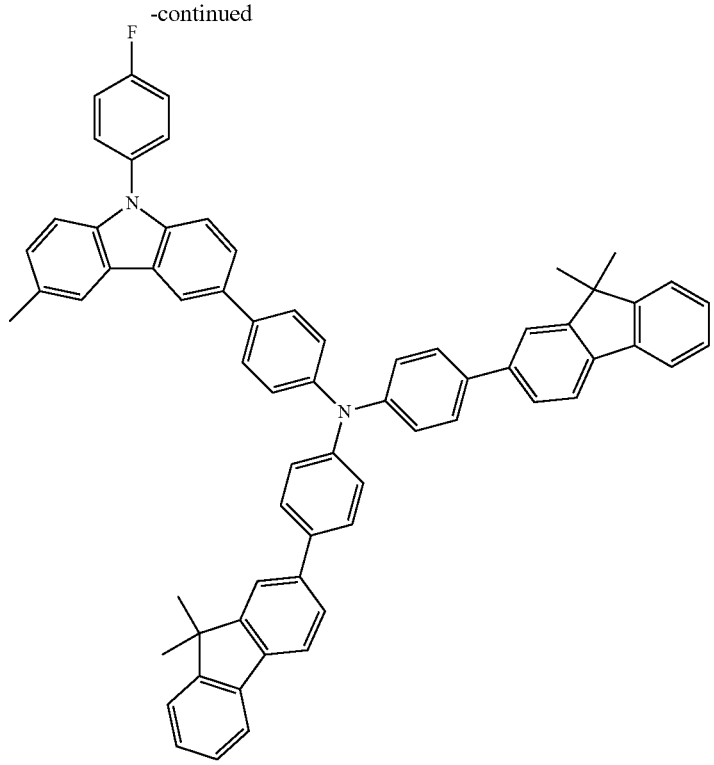

STRUCTURAL FORMULA 75

Preparation of Structural Formula 75A

The Structural Formula 75A was obtained by using the same method as the preparation method of the Structural Formula 1A, except that 4-fluoroiodobenzene was used instead of iodobenzene.

MS: $[M+H]^+=262$

Preparation of Structural Formula 75B

The Structural Formula 75B was obtained by using the same method as the preparation method of the Structural Formula 1B, except that the Structural Formula 75A was used instead of the Structural Formula 1A.

MS: $[M+H]^+=420$

Preparation of Structural Formula 75C

The Structural Formula 75C was obtained by using the same method as the preparation method of the Structural Formula 1C, except that the Structural Formula 75B was used instead of the Structural Formula 1B.

MS: $[M+H]^+=355$

Preparation of Structural Formula 75D

The Structural Formula 75D was obtained by using the same method as the preparation method of the Structural Formula 14D, except that the Structural Formula 75C was used instead of 2-bromo-9,9-dimethylfluorene.

MS: $[M+H]^+=320$

Preparation of Structural Formula 75E

The Structural Formula 75E was obtained by using the same method as the preparation method of the Structural Formula 14E, except that the Structural Formula 75D was used instead of the Structural Formula 14D.

MS: $[M+H]^+=367$

Preparation of Structural Formula 75

Structural Formula 75E (15 g, 40.9 mmol), and Structural Formula 1D (26.2 g, 86.0 mmol) were dissolved in 300 ml of xylene, sodium-tertiary-botoxide (9.4 g, 98.2 mmol), and Pd[P(t-Bu)$_3$]$_2$ (209 mg, 0.409 mmol) were added thereto, and heated and agitated for 1 hour under the nitrogen atmosphere. The organic layer in which 200 ml of distilled water was added to the reaction solution was extracted, concentrated, and purified through column to obtain the Structural Formula 75 (29.8 g, yield 81%).

MS: $[M+H]^+=903$

EXAMPLE 1

A glass substrate (7059 glass) on which a thin film of ITO (indium tin oxide) was coated to a thickness of 1,000 Å was immersed in distilled water having a detergent dissolved therein to wash the substrate with ultrasonic waves. The detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was carried out by using solvents such as isopropyl alcohol, acetone and methanol, and the resultant product was dried.

On the ITO transparent electrode thus prepared, hexanitrile hexaazatriphenylene was coated to thicknesses of 500 Å by thermal vacuum deposition to form a hole injecting layer. After the Structural Formula 1 (400 Å) that was the material transporting the holes and synthesized in the above Preparation Example was deposited under the vacuum state thereon, the host H1 and the dopant D1 compound were deposited under the vacuum state in a thickness of 300 Å as a light emitting layer. Thereafter, the E1 compound (300 Å) was deposited by heating under the vacuum as the electron injection and the transport layer. On the electron transport layer, lithium fluoride (LiF) in a thickness of 12 Å and aluminum in a thickness of 2,000 Å were subsequently deposited to form a cathode, thereby manufacturing the organic light emitting device.

NPB was used as a comparative example of the hole transport layer.

In the above process, the deposition speed of the organic substance was maintained at 1 Å/sec, that of lithium fluoride was maintained at 0.2 Å/sec, and that of aluminum was maintained at 3 to 7 Å/sec.

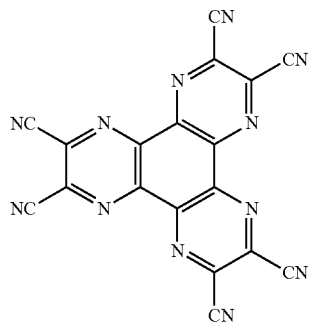

[hexanitrile hexaazatriphenylene]

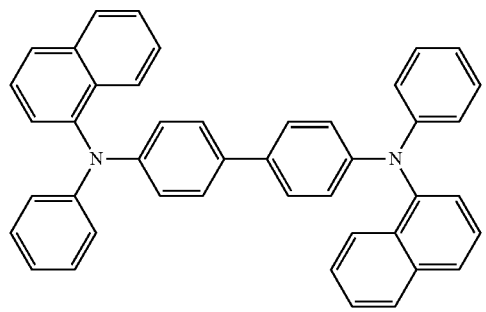

[NPB]

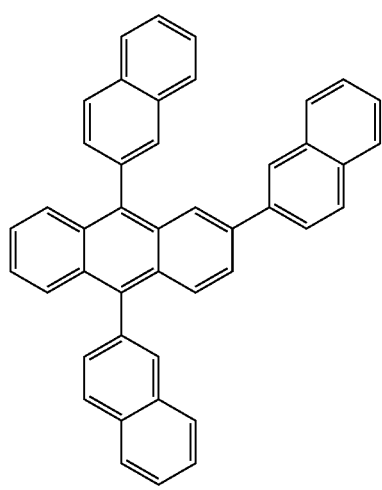

[H1]

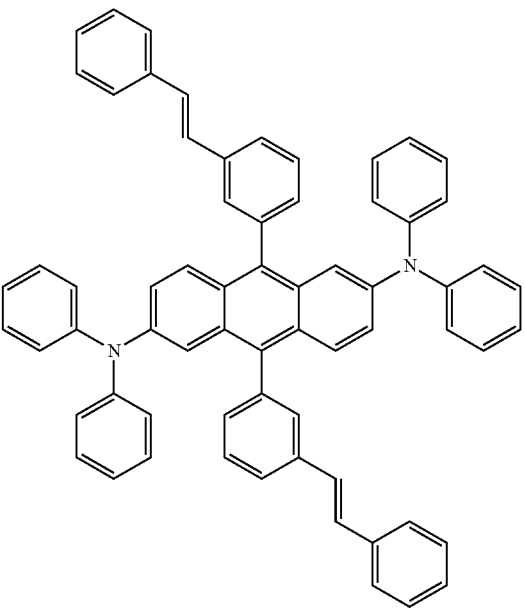

[D1]

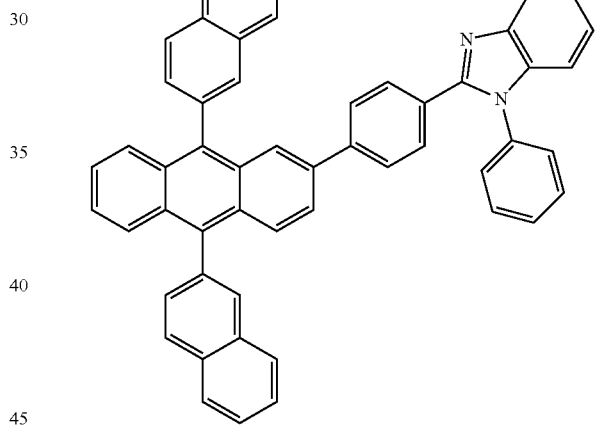

[E1]

EXAMPLE 2

The same experiment was conducted, except that Structural Formula 14 was used instead of Structural Formula 1 that was synthesized in Preparation Example as the hole transport layer in Example 1.

EXAMPLE 3

The same experiment was conducted, except that Structural Formula 18 was used instead of Structural Formula 1 that was synthesized in Preparation Example as the hole transport layer in Example 1.

EXAMPLE 4

The same experiment was conducted, except that Structural Formula 21 was used instead of Structural Formula 1 that was synthesized in Preparation Example as the hole transport layer in Example 1.

EXAMPLE 5

The same experiment was conducted, except that Structural Formula 27 was used instead of Structural Formula 1 that was synthesized in Preparation Example as the hole transport layer in Example 1.

EXAMPLE 6

The same experiment was conducted, except that Structural Formula 33 was used instead of Structural Formula 1 that was synthesized in Preparation Example as the hole transport layer in Example 1.

EXAMPLE 7

The same experiment was conducted, except that Structural Formula 48 was used instead of Structural Formula 1 that was synthesized in Preparation Example as the hole transport layer in Example 1.

EXAMPLE 8

The same experiment was conducted, except that Structural Formula 56 was used instead of Structural Formula 1 that was synthesized in Preparation Example as the hole transport layer in Example 1.

EXAMPLE 9

The same experiment was conducted, except that Structural Formula 59 was used instead of Structural Formula 1 that was synthesized in Preparation Example as the hole transport layer in Example 1.

EXAMPLE 10

The same experiment was conducted, except that Structural Formula 75 was used instead of Structural Formula 1 that was synthesized in Preparation Example as the hole transport layer in Example 1.

COMPARATIVE EXAMPLE 1

The same experiment was conducted, except that NPB was used instead of Structural Formula 1 that was synthesized in Preparation Example as the hole transport layer in Example 1.

Like the above Examples, the experiment results of the organic light emitting device that was prepared by using the compound as the hole transport layer material are described in Table 1.

TABLE 1

| Experimental Example 100 mA/cm$^2$ | HTL material | voltage (V) | Current efficiency (cd/A) | Color coordinate (x, y) |
| --- | --- | --- | --- | --- |
| Comparative Example | NPB | 8.19 | 25.92 | (0.314, 0.650) |
| Example 1 | Structural Formula 1 | 8.51 | 26.63 | (0.316, 0.652) |
| Example 2 | Structural Formula 14 | 8.28 | 28.88 | (0.317, 0.650) |
| Example 3 | Structural Formula 18 | 8.31 | 26.59 | (0.315, 0.653) |
| Example 4 | Structural Formula 21 | 8.28 | 28.21 | (0.318, 0.652) |
| Example 5 | Structural Formula 27 | 8.09 | 29.01 | (0.317, 0.652) |
| Example 6 | Structural Formula 33 | 8.45 | 28.90 | (0.319, 0.656) |
| Example 7 | Structural Formula 48 | 8.21 | 28.34 | (0.319, 0.657) |
| Example 8 | Structural Formula 56 | 8.10 | 28.84 | (0.318, 0.657) |
| Example 9 | Structural Formula 59 | 8.42 | 28.55 | (0.317, 0.651) |
| Example 10 | Structural Formula 75 | 8.12 | 29.02 | (0.314, 0.653) |

A compound derivative of Formula according to the present invention may act as a hole injection, hole transport, electron injection and transport, or light emitting material in an organic light emitting device and an organic electronic device, and the device according to the present invention shows excellent properties in terms of efficiency, a driving voltage, and stability.

The invention claimed is:

1. A compound that is represented by the following Formula 1:

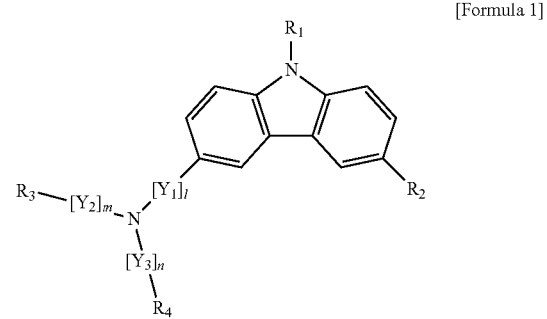

[Formula 1]

wherein l, m and n are each independently an integer in the range of 0 to 5, $Y_1$ to $Y_3$ are each independently selected from the group consisting of $C_{2-40}$ alkenylene group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{6-40}$ arylene group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{4-40}$ divalent hetero ring group that is unsubstituted or substituted by one or more substituent groups selected from the group consisting of halogen group, alkyl group, alkenyl group, alkoxy group, substituted or unsubstituted arylamine group, substituted or unsubstituted aryl group, substituted or unsubstituted arylalkyl group, substituted or unsubstituted arylalkenyl group, substituted or unsubstituted hetero ring group, nitrile group and acetylene group and has O, N or S as a heteroatom; divalent amine group that is substituted by one or more substituent groups selected from the group consisting of alkyl group, alkenyl group, substituted or unsubstituted aryl group, substituted or unsubstituted arylalkyl group, substituted or unsubstituted arylalkenyl group; fluorenylene group that is unsubstituted or substituted by one or more substituent groups selected from the group consisting of alkyl group, alkenyl group, substituted or unsubstituted aryl group, substituted or unsubstituted arylalkyl group, substituted or unsubstituted arylalkenyl group; amide group; ester group; silane group and germanium group, $R_1$, $R_3$ and $R_4$ are each independently selected from the group consisting of $C_{1-40}$ alkyl group that is unsubstituted or substituted by one or more substituent groups selected from the group consisting of alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{1-40}$ alkoxy group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{2-40}$ alkenyl group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{6-40}$ aryl group that is unsubstituted or substituted by one or more substituent groups selected from the group consisting of halogen group, alkyl group, alkenyl group, alkoxy group, substituted or unsubstituted arylamine group, substituted or unsubstituted aryl group, substituted or unsubstituted arylalkyl group, substituted or unsubstituted arylalkenyl group, substituted or unsubstituted hetero ring group, nitrile group and acetylene group; $C_{4-40}$ hetero ring group that is unsubstituted or substituted by one or more substituent groups selected from the group consisting of halogen group, alkyl group, alkenyl group, alkoxy group, substituted or unsubstituted arylamine group, substituted or unsubstituted aryl group, substituted or unsubstituted arylalkyl group, substituted or unsubstituted arylalkenyl group, substituted or unsubstituted hetero ring group, nitrile group and acetylene group and has O, N or S as a heteroatom; amine group that is unsubstituted or substituted by one or more substituent groups selected from the group consisting of alkyl group, alkenyl group, substituted or unsubstituted aryl group, substituted or unsubstituted arylalkyl group, substituted or unsubstituted arylalkenyl group; fluorenyl group that is substituted by one or more substituent groups selected from the group consisting of alkyl group, alkenyl group, substituted or unsubstituted aryl group, substituted or unsubstituted arylalkyl group, substituted or unsubstituted arylalkenyl group; bisspirofluorenyl group; nitrile group; nitro group; silane group and germanium group, $R_2$ is selected from the group consisting of $C_{1-40}$ alkyl group that is unsubstituted or substituted by one or more substituent groups selected from the group consisting of alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{1-40}$ alkoxy group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{6-40}$ aryl group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{4-40}$ hetero ring group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group and has O, N or S as a heteroatom; fluorenyl group that is substituted by one or more substituent groups selected from the group consisting of alkyl group, alkenyl group, substituted or unsubstituted aryl group, substituted or unsubstituted arylalkyl group, and substituted or unsubstituted arylalkenyl group; bisspirofluorenyl group; nitrile group; nitro group; silane group; germanium group and halogen group, at least one of $R_3$ or $R_4$ comprises the structure of the following Formula 2,

[Formula 2]

wherein $R_5$ to $R_7$ are each independently selected from the group consisting of hydrogen; halogen group; $C_{1-40}$ alkyl group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{1-40}$ alkoxy group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{2-40}$ alkenyl group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{6-40}$ aryl group that is unsubstituted or substituted by one or more substituent groups selected from the group consisting of halogen group, alkyl group, alkenyl group, alkoxy group, substituted or unsubstituted aryl group, substituted or unsubstituted arylalkyl group, substituted or unsubstituted arylalkenyl group, substituted or unsubstituted hetero ring group, nitrile group and acetylene group; $C_{4-40}$ hetero ring group that is unsubstituted or substituted by one or more substituent groups selected from the group consisting of halogen group, alkyl group, alkenyl group, alkoxy group, substituted or unsubstituted arylamine group, substituted or unsubstituted aryl group, substituted or unsubstituted arylalkyl group, substituted or unsubstituted arylalkenyl group, substituted or unsubstituted hetero ring group, nitrile group and acetylene group and has O, N or S as a heteroatom; amine group that is substituted by one or more substituent groups selected from the group consisting of alkyl group, alkenyl group, substituted or unsubstituted aryl group, substituted or unsubstituted arylalkyl group, substituted or unsubstituted arylalkenyl group; nitrile group; nitro group; silane group and germanium group, and they may form an aliphatic or hetero condensation ring in conjunction with adjacent groups.

2. The compound according to claim 1, wherein $Y_1$ to $Y_3$ are each independently selected from the group consisting of $C_{6-20}$ arylene group that is unsubstituted or substituted by one or more substituent groups selected from the group consisting of halogen group, $C_{1-20}$ alkyl group, $C_{6-20}$ aryl group, $C_{7-20}$ arylalkyl group and $C_{4-20}$ hetero ring group; $C_{4-20}$ divalent hetero ring group that is unsubstituted or substituted by one or more substituent groups selected from the group consisting of halogen group, $C_{1-20}$ alkyl group, $C_{6-20}$ arylamine group, $C_{6-20}$ aryl group, $C_{7-20}$ arylalkyl group and $C_{4-20}$ hetero ring group and has O, N or S as a heteroatom; and fluorenylene group that is unsubstituted or substituted by one or more substituent groups selected from the group consisting of $C_{1-20}$ alkyl group, $C_{6-20}$ aryl group and $C_{7-20}$ arylalkyl group.

3. The compound according to claim 1, wherein $Y_1$ to $Y_3$ are each independently selected from the divalent group consisting of phenylene, biphenylene, terphenylene, stilbene, naphthylene, anthracene, phenanthrene, pyrene, perylene, fluorene, thiophene, furane, pyrol, imidazole, thiazol, oxazole, oxadiazole, triazole, pyridine, pyradazine, quinoline, isoquinoline and acrydine.

4. The compound according to claim 1, wherein $R_1$, $R_3$ and $R_4$ are each independently selected from the group consisting of $C_{1-20}$ alkyl group that is unsubstituted or substituted by one or more substituent groups selected from the group consisting of $C_{1-20}$ alkyl group, $C_{6-20}$ aryl group, $C_{7-20}$ arylalkyl group and $C_{4-20}$ hetero ring group; $C_{6-20}$ aryl group that is unsubstituted or substituted by one or more substituent groups selected from the group consisting of halogen group, $C_{1-20}$ alkyl group, $C_{6-20}$ arylamine group, $C_{6-20}$ aryl group, $C_{7-20}$ arylalkyl group and $C_{4-20}$ hetero ring group; $C_{4-20}$ hetero ring group that is unsubstituted or substituted by one or more substituent groups selected from the group consisting of halogen group, $C_{1-20}$ alkyl group, $C_{6-20}$ arylamine group, $C_{6-20}$ aryl group, $C_{7-20}$ arylalkyl group and $C_{4-20}$ hetero ring group and has O, N or S as a heteroatom; amine group that is substituted by one or more substituent groups selected from the group consisting of $C_{1-20}$ alkyl group, $C_{6-20}$ aryl group and $C_{7-20}$ arylalkyl group; fluorenyl group that is substituted by $C_{1-20}$ alkyl group or $C_{6-20}$ aryl group; bisspirofluorenyl group; cyano group; nitro group; and silane group that is substituted by $C_{6-20}$ aryl group, and $R_5$ to $R_7$ are each independently selected from the group consisting of hydrogen; halogen group; $C_{1-20}$ alkyl group that is unsubstituted or substituted by one or more substitutent groups selected from the group consisting of halogen group, $C_{1-20}$ alkyl group, $C_{6-20}$ aryl group, $C_{7-20}$ arylalkyl group and $C_{4-20}$ hetero ring group; $C_{6-20}$ aryl group that is unsubstituted or substituted by one or more substituent groups selected from the group consisting of halogen group, $C_{1-20}$ alkyl group, $C_{6-20}$ aryl group, $C_{7-20}$ arylalkyl group and $C_{4-20}$ hetero ring group; and $C_{4-40}$ hetero ring group that is unsubstituted or substituted by one or more substituent groups selected from the group consisting of halogen group, $C_{1-20}$ alkyl group, $C_{6-20}$ arylamine group, $C_{6-20}$ aryl group, $C_{7-20}$ arylalkyl group and $C_{4-20}$ hetero ring group and has O, N or S as a heteroatom, and they may form an aliphatic or hetero condensation ring in conjunction with adjacent groups.

5. The compound according to claim 1, wherein $R_2$ is selected from the group consisting of $C_{1-20}$ alkyl group that is unsubstituted or substituted by one or more substituent groups selected from the group consisting of $C_{1-20}$ alkyl group, $C_{6-20}$ aryl group, $C_{7-20}$ arylalkyl group and $C_{4-20}$ hetero ring group; $C_{6-20}$ aryl group that is unsubstituted or substituted by one or more substituent groups selected from the group consisting of halogen group, $C_{1-20}$ alkyl group, $C_{6-20}$ aryl group, $C_{7-20}$ arylalkyl group and $C_{4-20}$ hetero ring group; $C_{4-20}$ hetero ring group that is unsubstituted or substituted by one or more substituent groups selected from the group consisting of halogen group, $C_{1-20}$ alkyl group, $C_{6-20}$ aryl group, $C_{7-20}$ arylalkyl group and $C_{4-20}$ hetero ring group and has O, N or S as a heteroatom; fluorenyl group that is substituted by $C_{1-20}$ alkyl group or $C_{6-20}$ aryl group; bisspirofluorenyl group; cyano group; nitro group; silane group that is unsubstituted or substituted by $C_{6-20}$ aryl group; and halogen group.

6. The compound according to claim 1, wherein $R_1$ to $R_7$ are each independently selected from the group consisting of phenyl group, biphenyl group, terphenyl group, stilbene, naphthyl group, anthracenyl group, phenanthrene group, pyrenyl group, perylenyl group, fluorene group, thiophene group, furane group, pyrol group, imidazole group, thiazol group, oxazole group, oxadiazole group, triazole group, pyridyl group, pyradazine group, quinolinyl group, isoquinoline group and acrydyl group.

7. The compound according to claim 1, wherein $R_2$ is selected from the group consisting of alkyl group that is selected from the group consisting of methyl group, ethyl group and propyl group; aryl group that is selected from the group consisting of phenyl group, biphenyl group and naphthyl group; fluorenyl group; and bisspirofluorenyl group.

8. The compound according to claim 1, wherein $R_2$ is selected from the group consisting of hetero ring that is selected from the group consisting of thiophene group and furane group; alkoxy group that is selected from the group consisting of methoxy group and ethoxy group; cyano group; nitro group; silane group; and halogen group.

9. The compound according to claim 1, wherein the structure of Formula 2 is any one of the following Structural Formulas
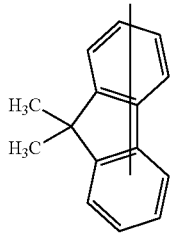 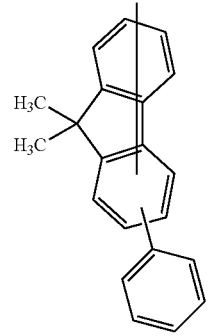 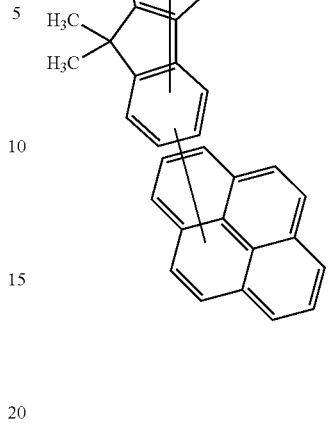 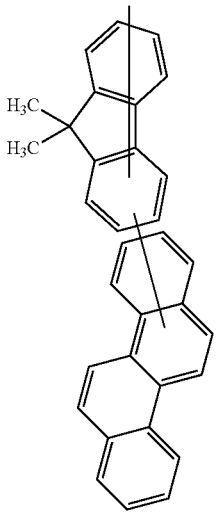
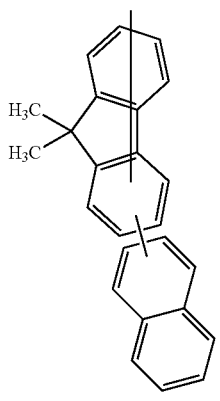 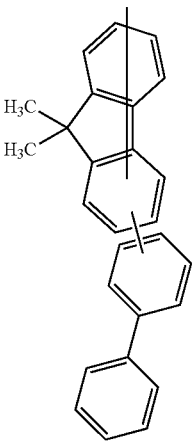 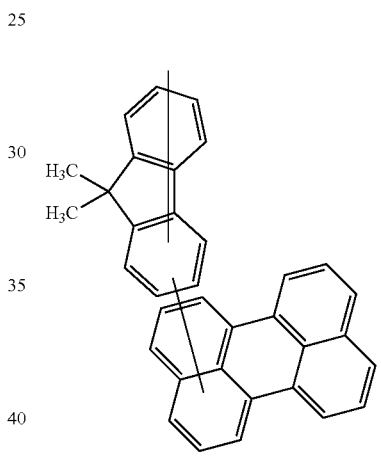 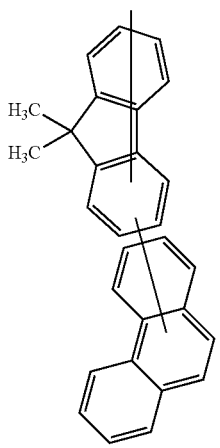
-continued
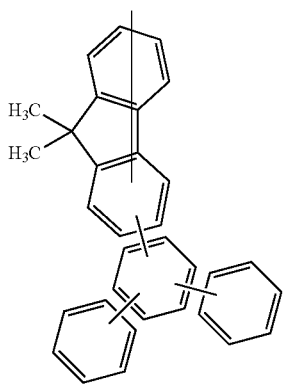 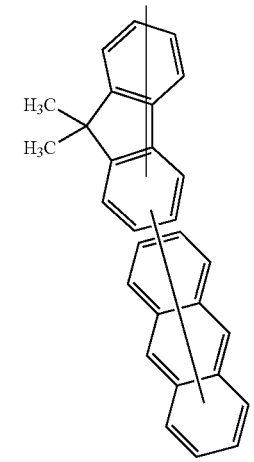 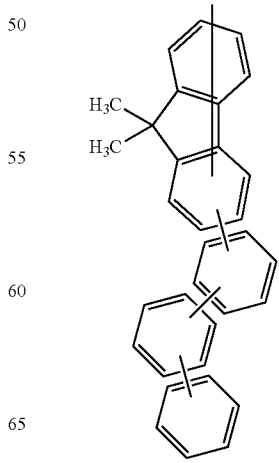 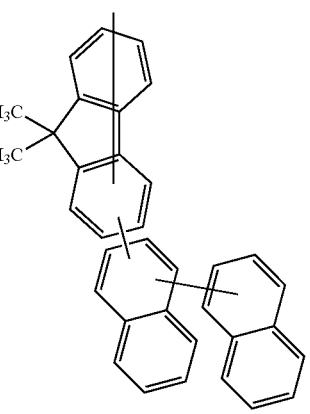

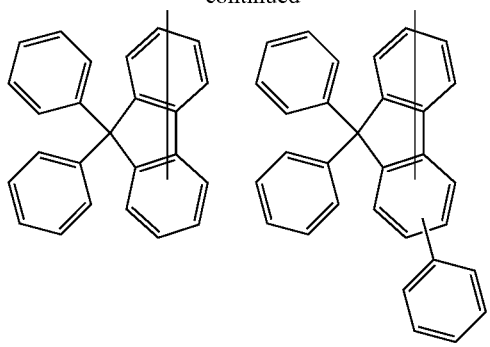
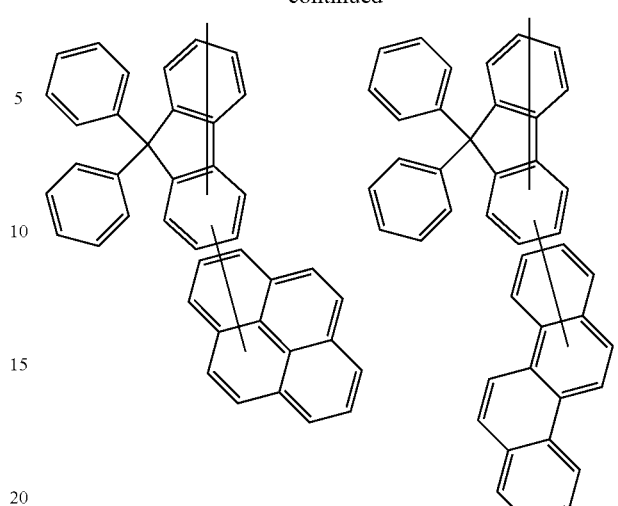
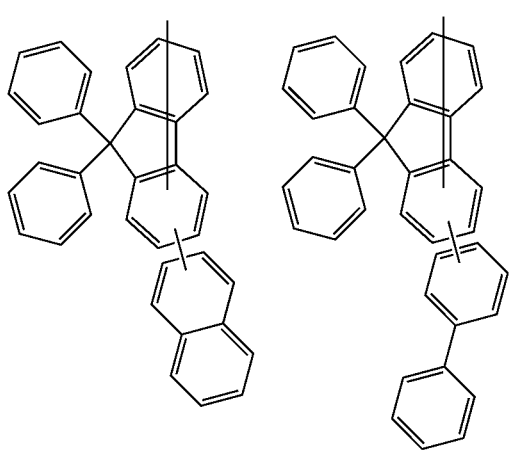
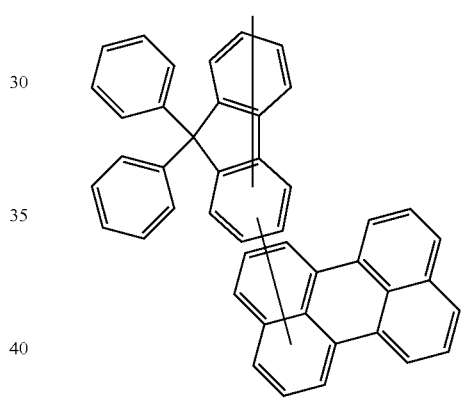
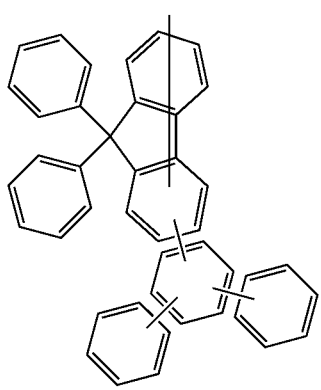
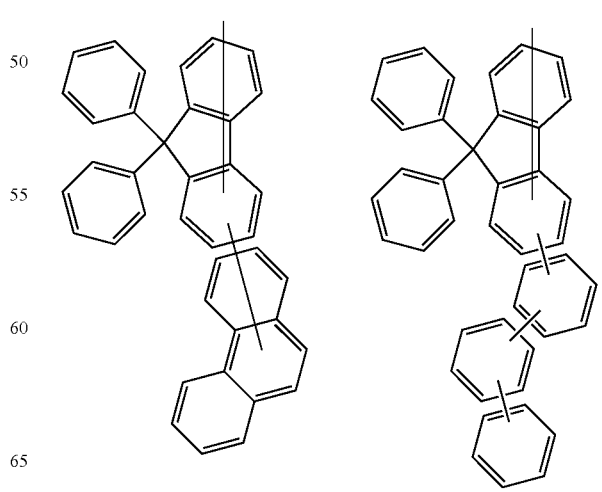
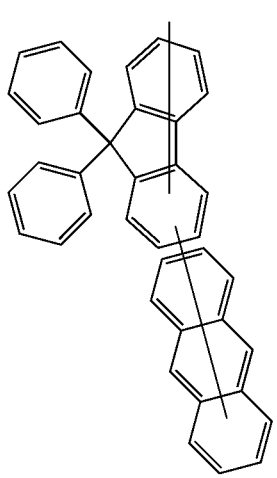

101
-continued
102
-continued
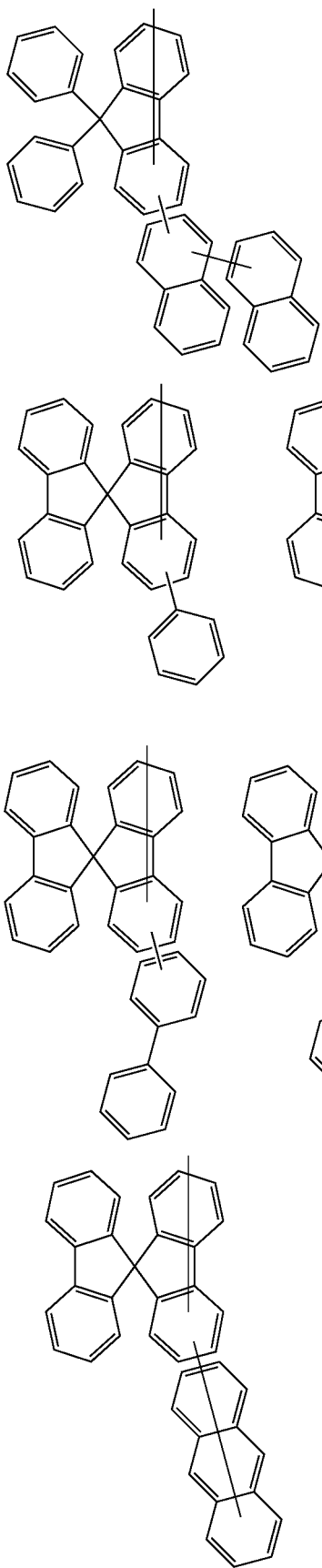
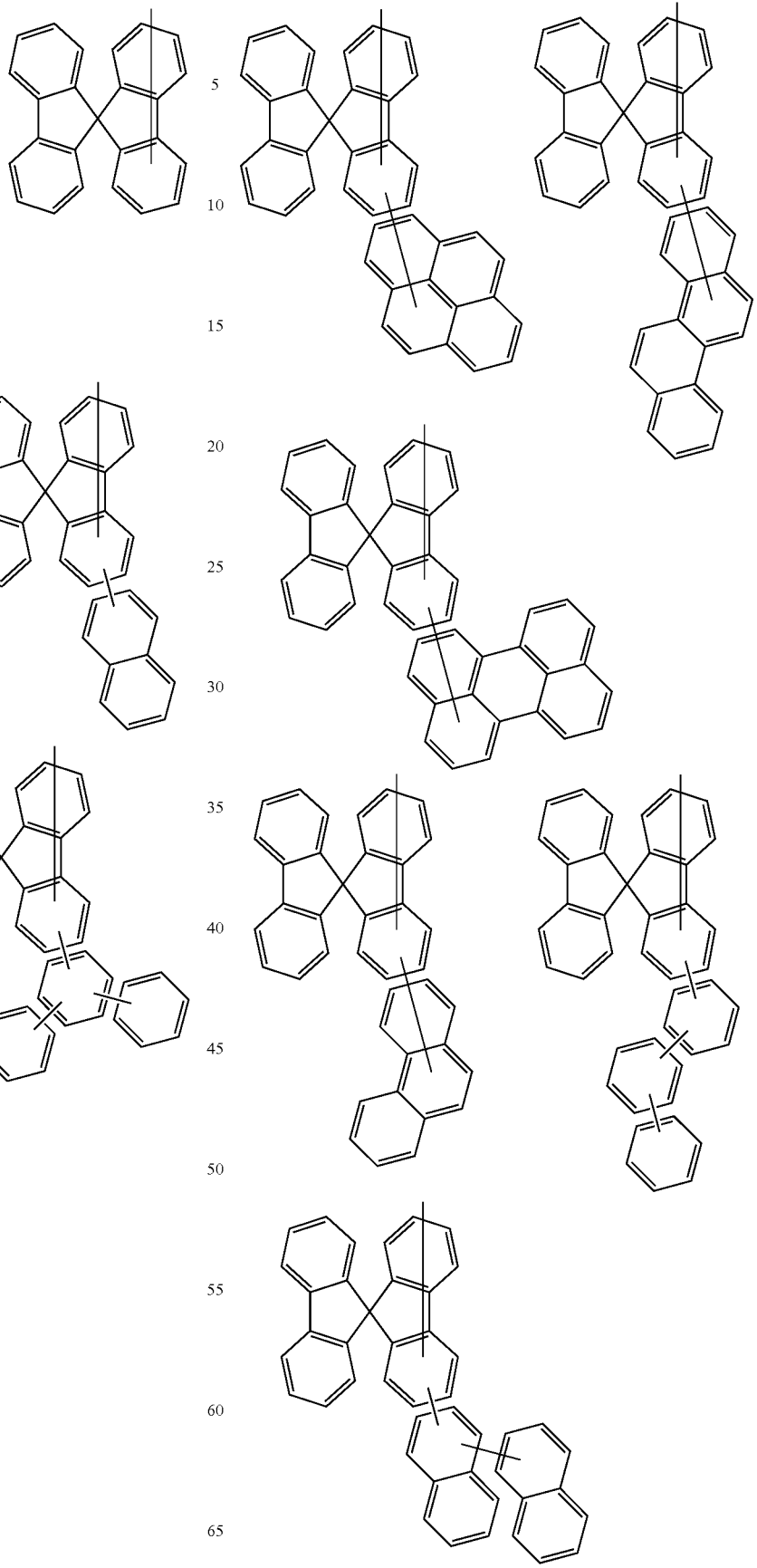

10. The compound according to claim 1, wherein the compound is a compound that is represented by any one of the following Structural Formulas 1 to 80
Structural Formula 1
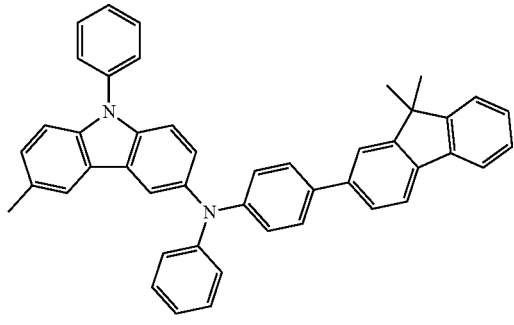
Structural Formula 2
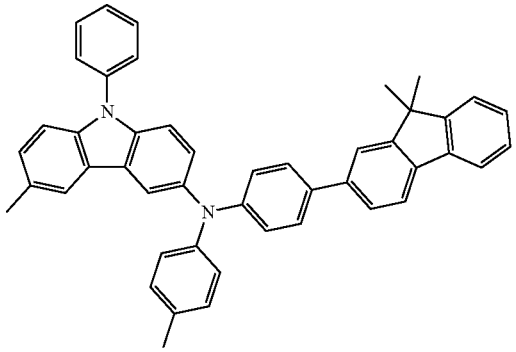
Structural Formula 3
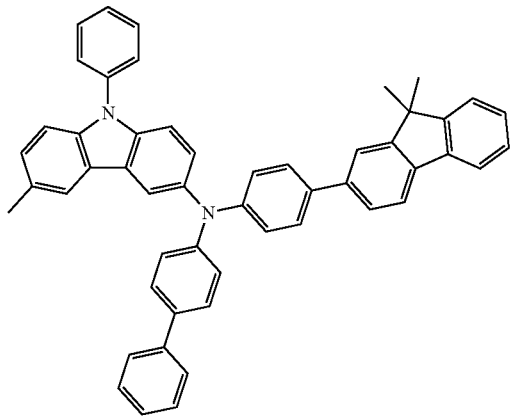
Structural Formula 4
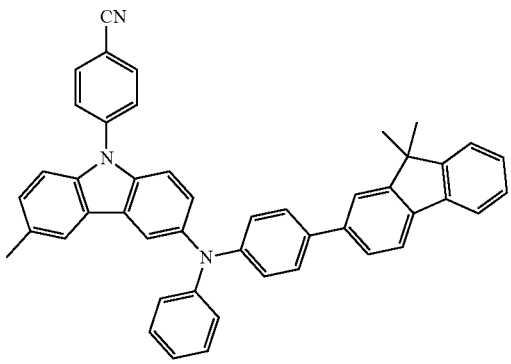
Structural Formula 5
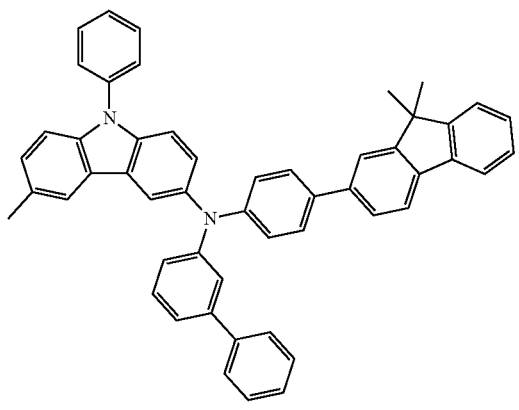
Structural Formula 6
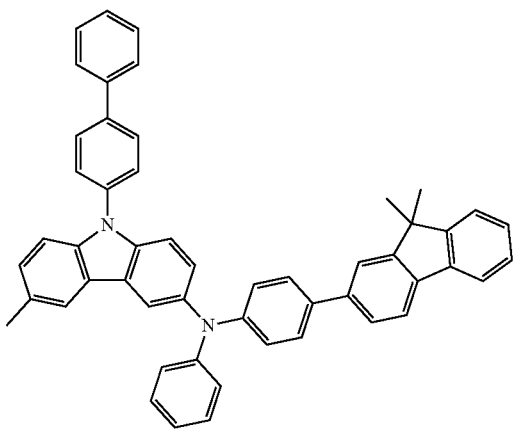

-continued
Structural Formula 7
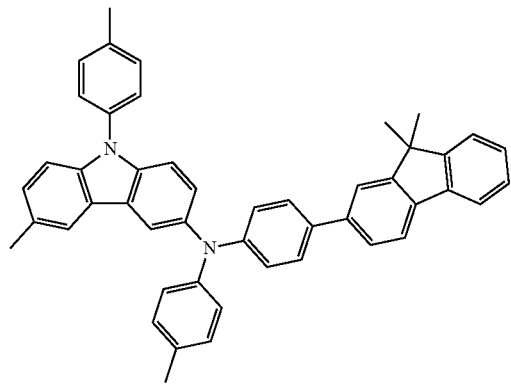
Structural Formula 8
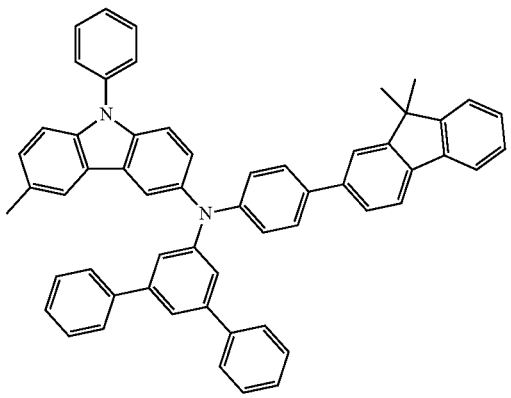
Structural Formula 9
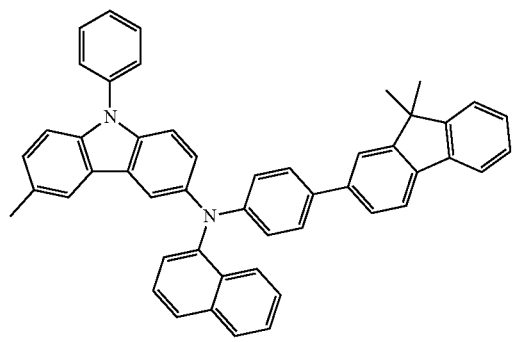
Structural Formula 10
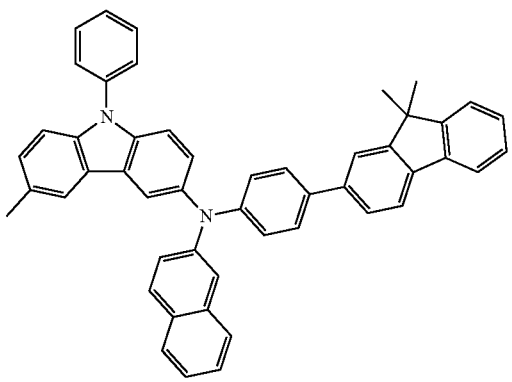
Structural Formula 11
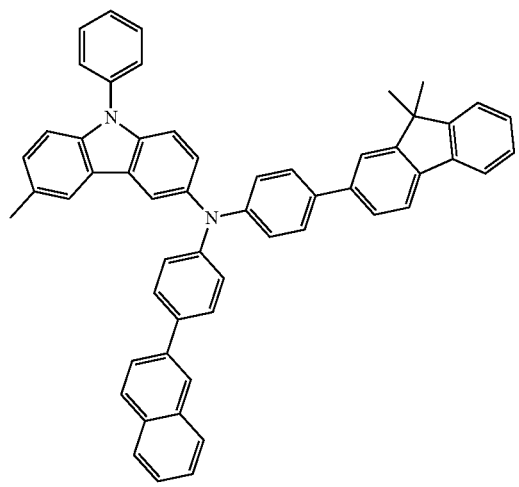
Structural Formula 12
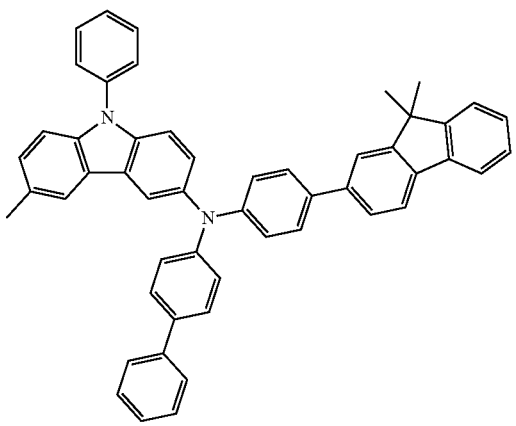

-continued
Structural Formula 13
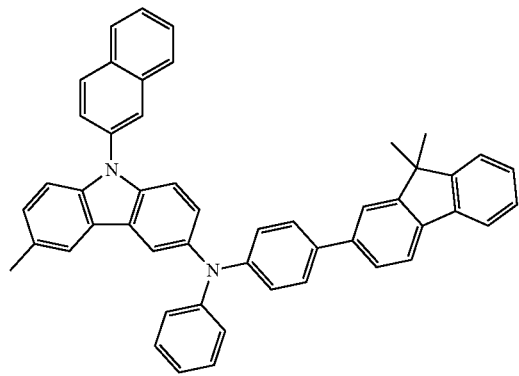
Structural Formula 14
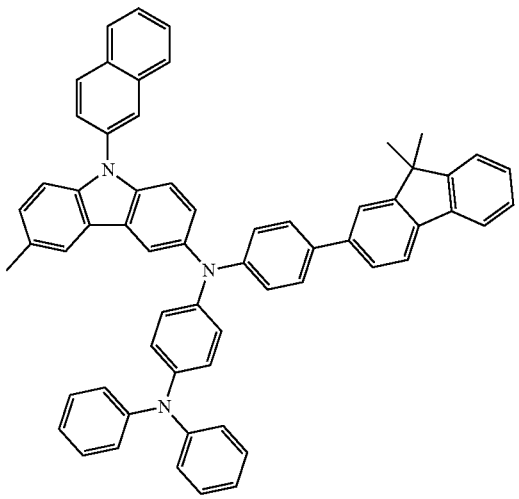
Structural Formula 15
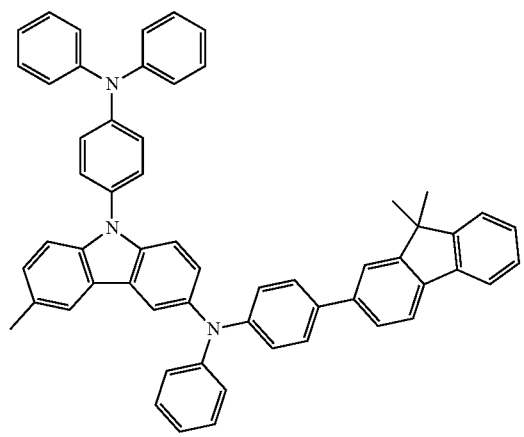
Structural Formula 16
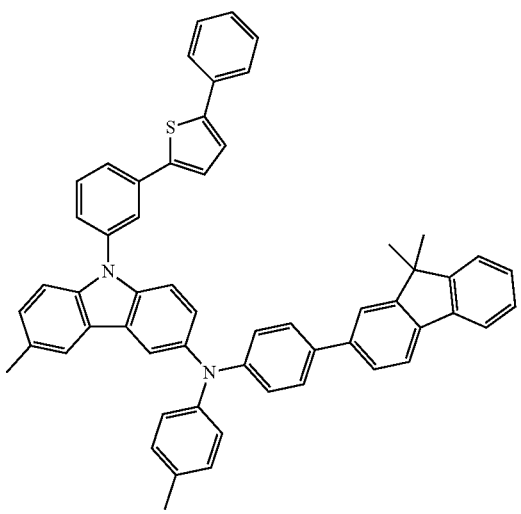
Structural Formula 17
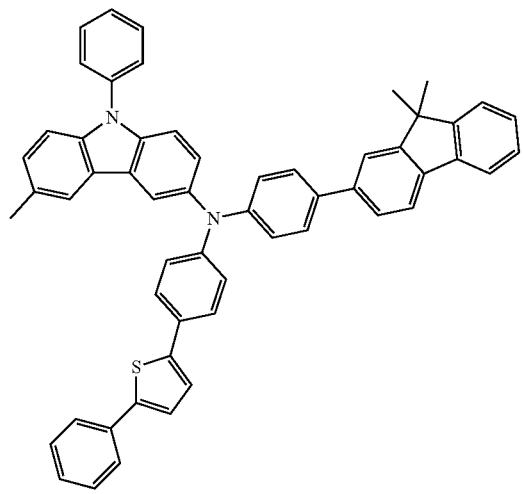
Structural Formula 18
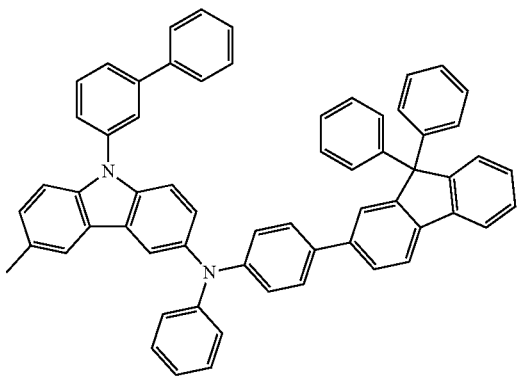

-continued
Structural Formula 19
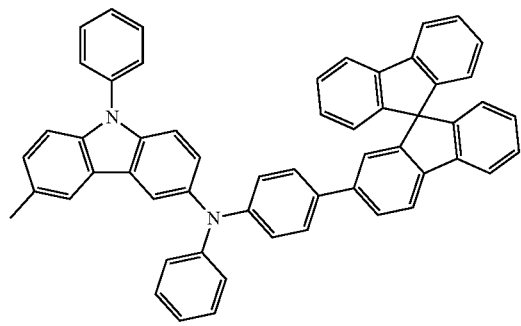
Structural Formula 20
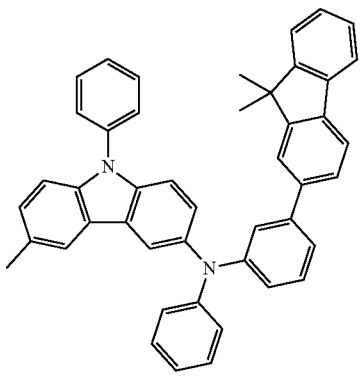
Structural Formula 21
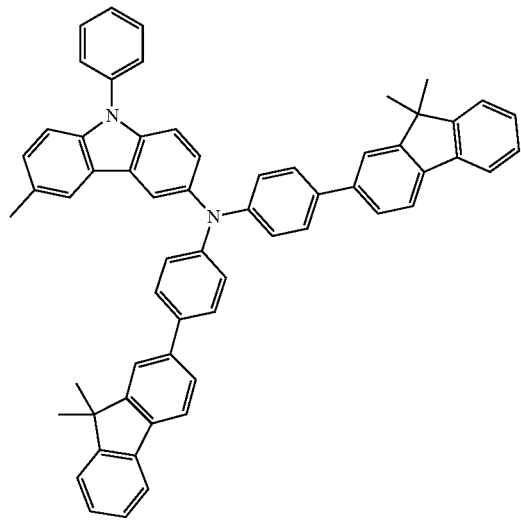
Structural Formula 22
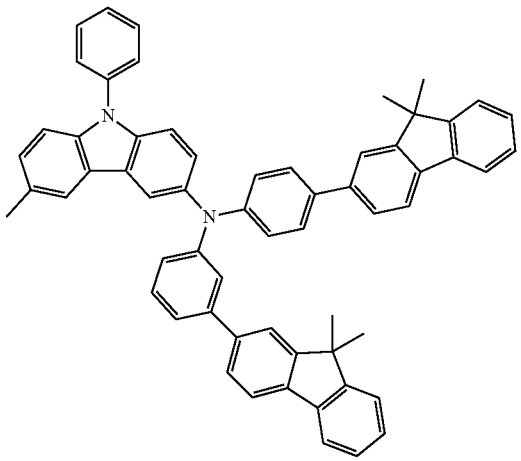
Structural Formula 23
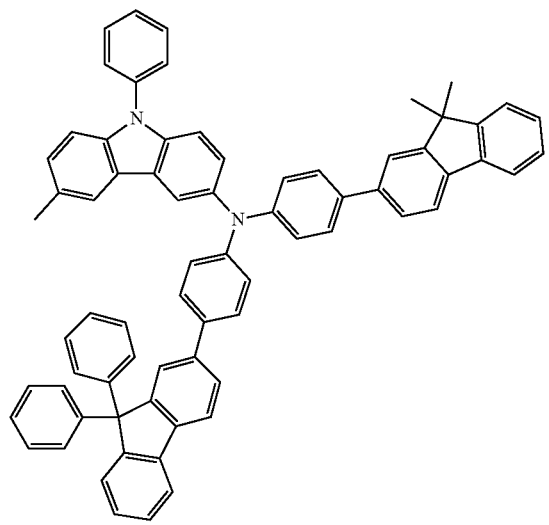
Structural Formula 24
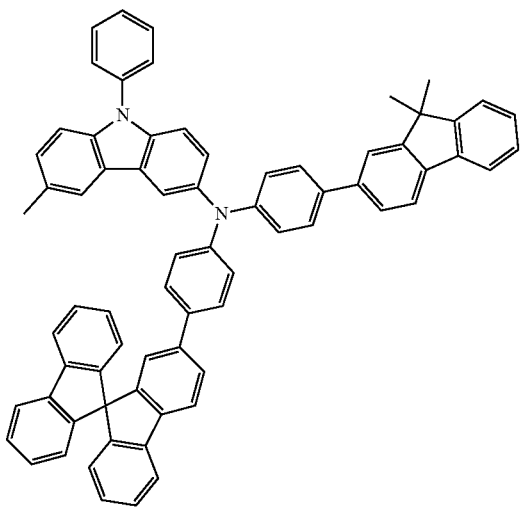

-continued
Structural Formula 25
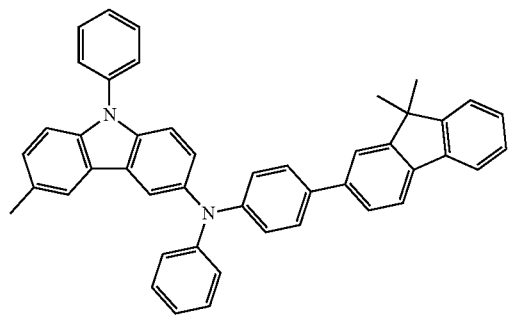
Structural Formula 26
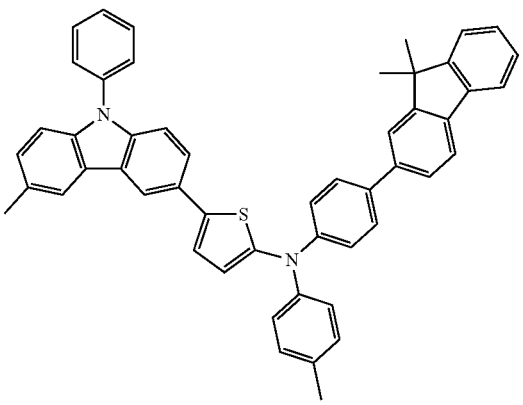
Structural Formula 27
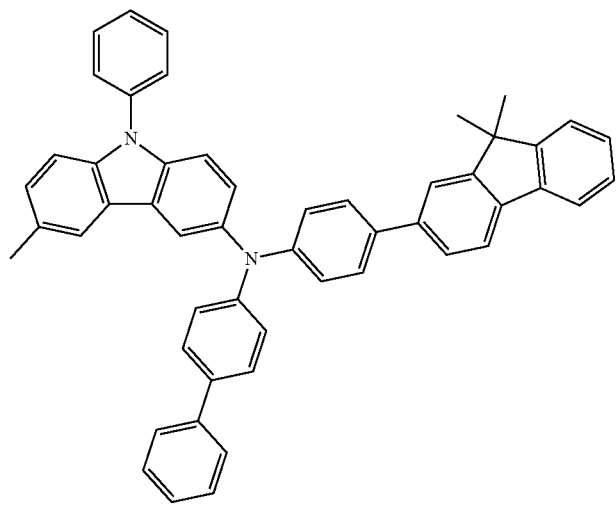
Structural Formula 28
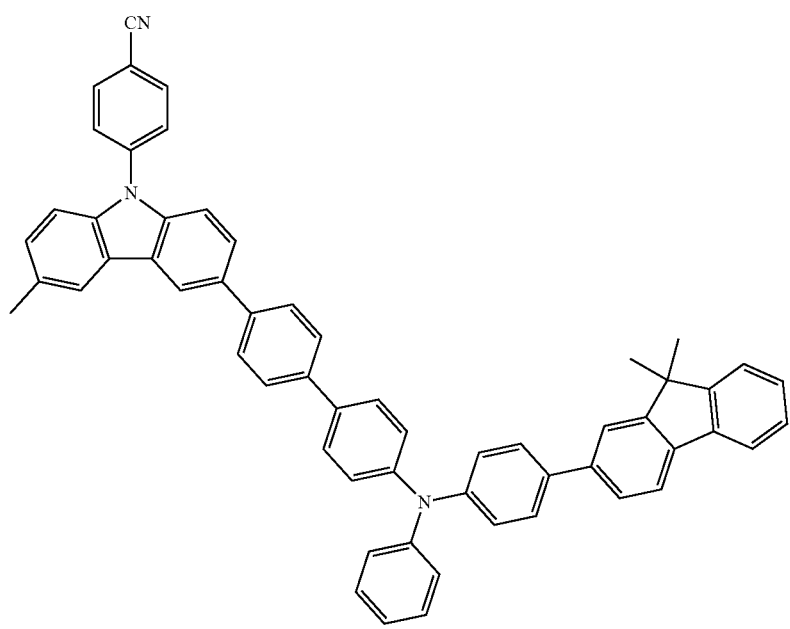

-continued
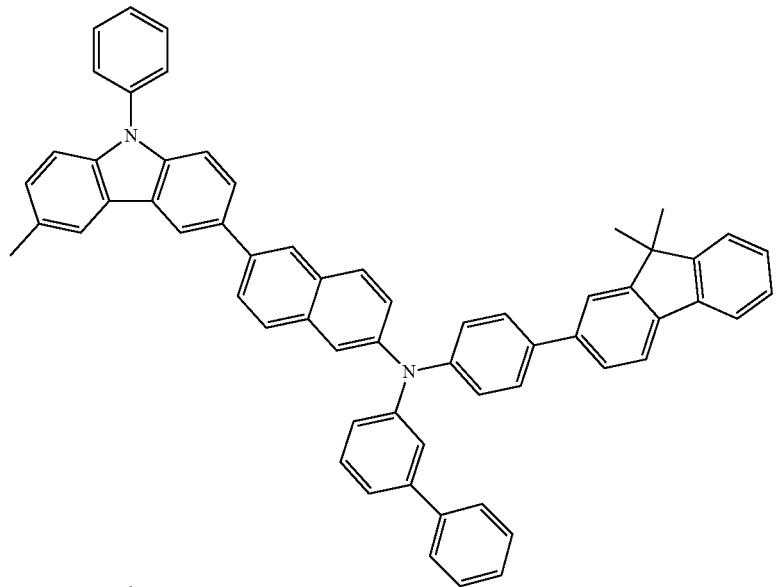
Structural Formula 29
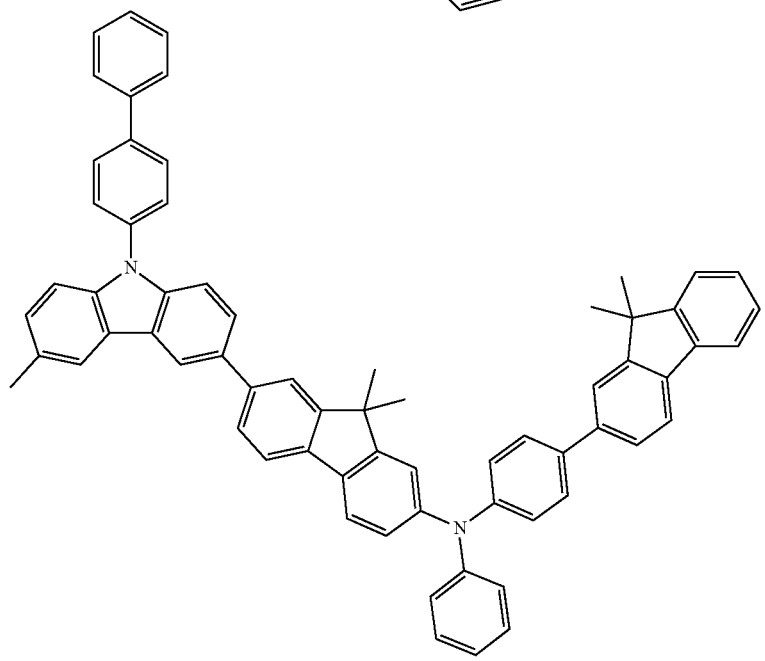
Structural Formula 30
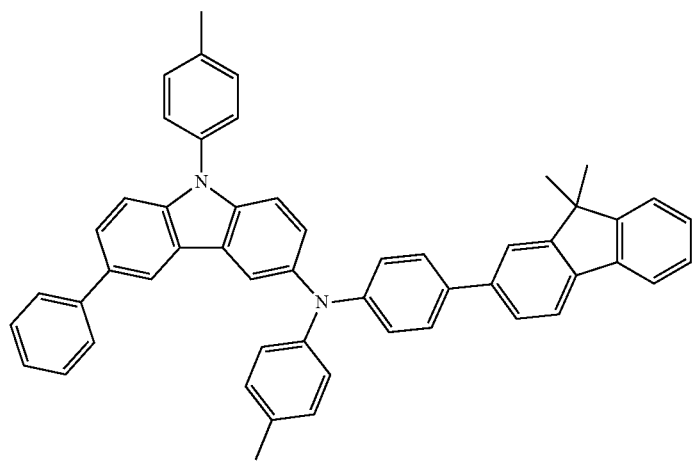
Structural Formula 31

Structural Formula 32
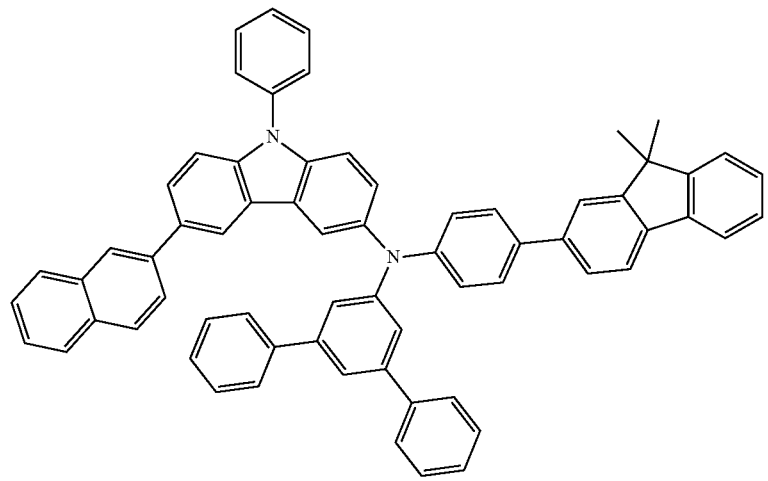
Structural Formula 33
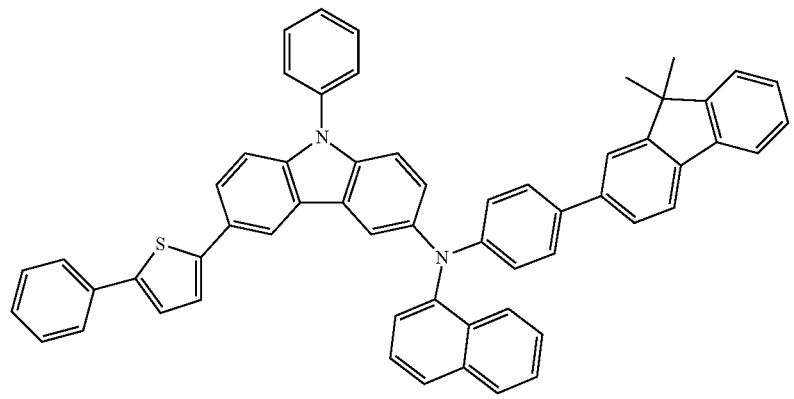
Structural Formula 34
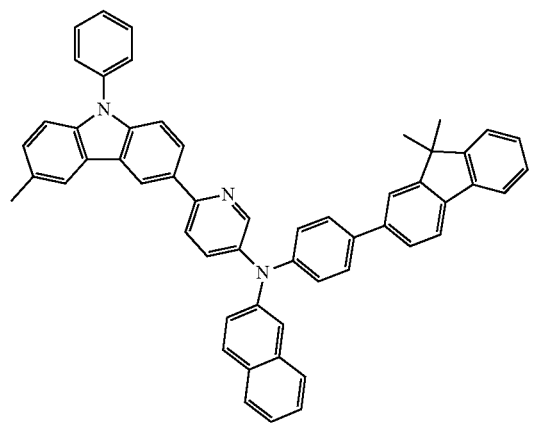
Structural Formula 35
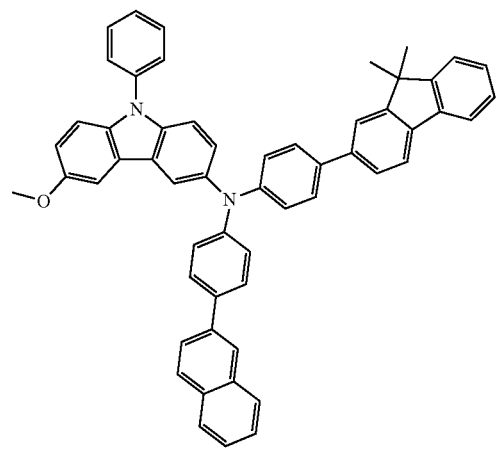

Structural Formula 36
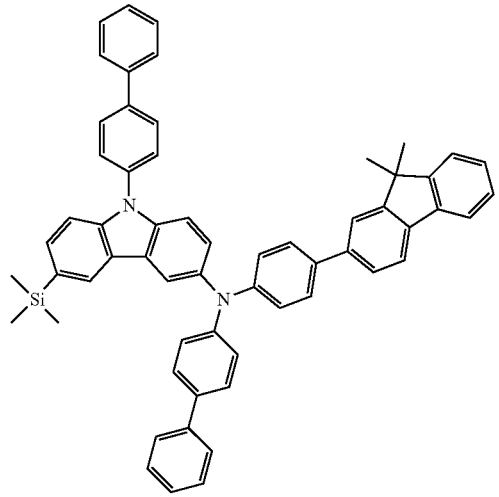
Structural Formula 38
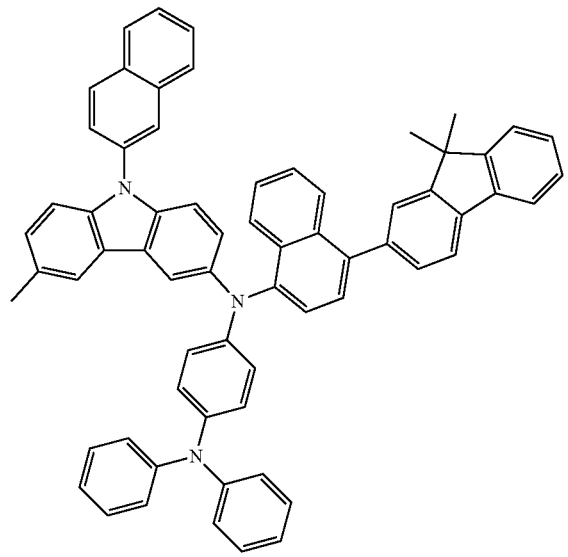
Structural Formula 39
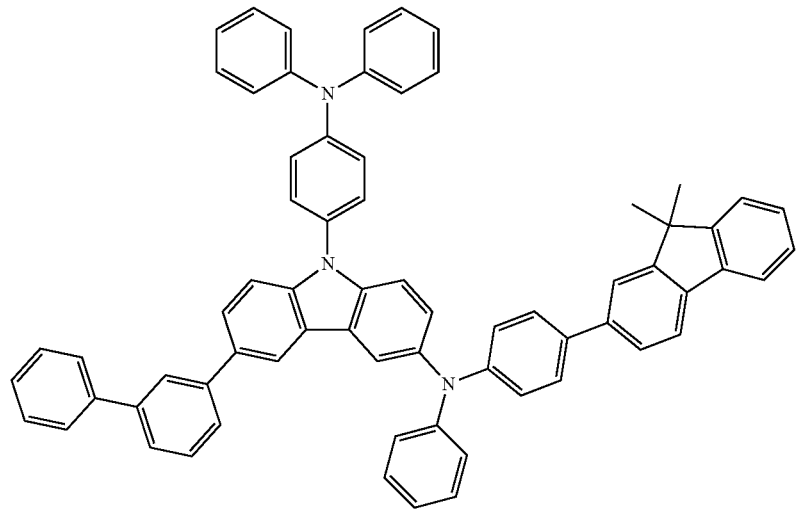

Structural Formula 40
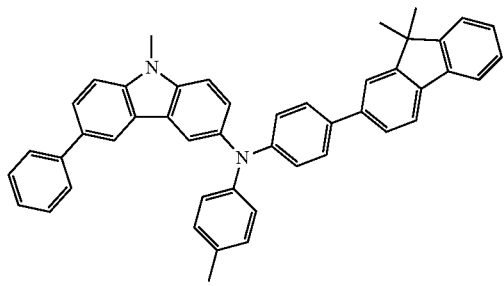
Structural Formula 41
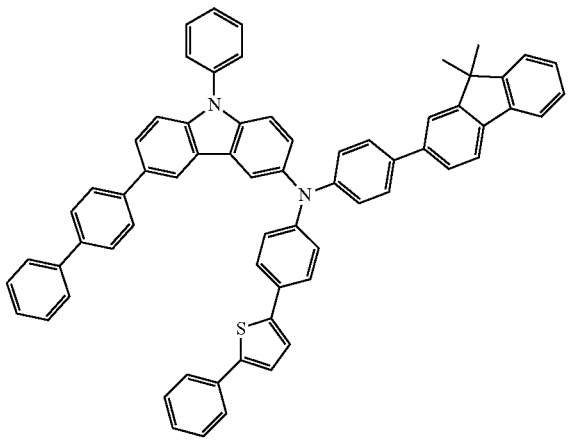
Structural Formula 42
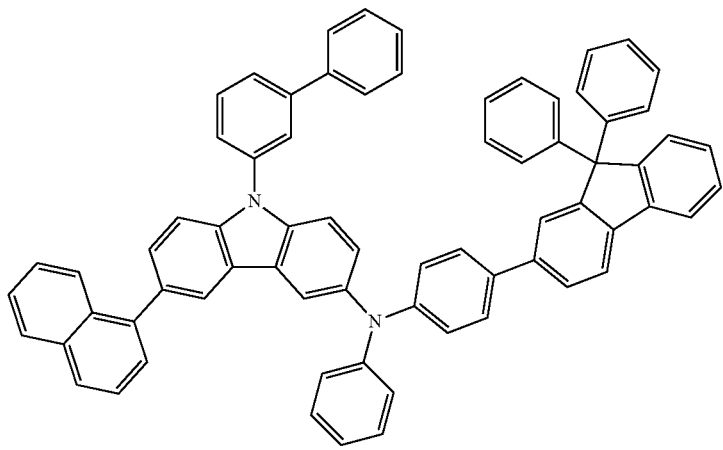
Structural Formula 43
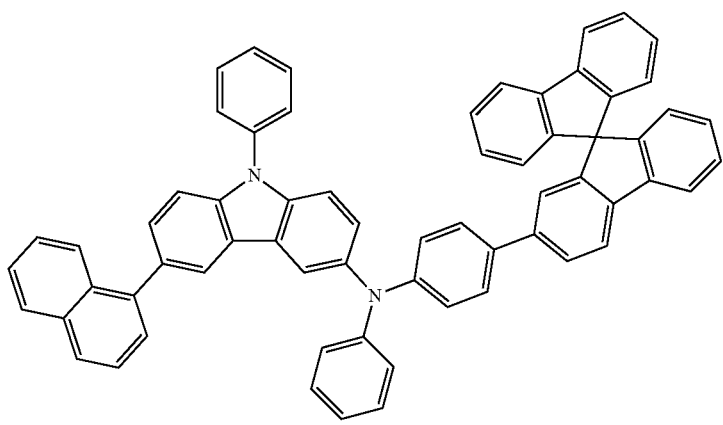

Structural Formula 44
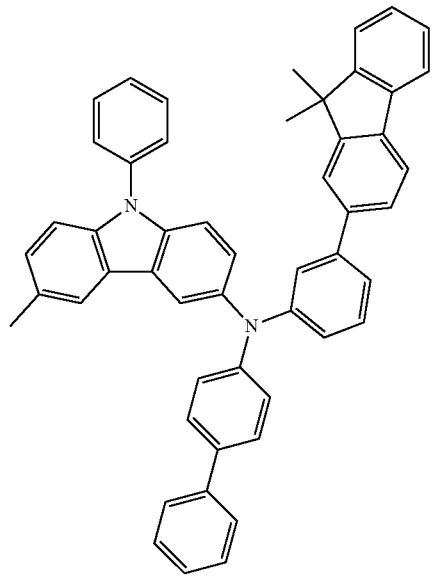
Structural Formula 45
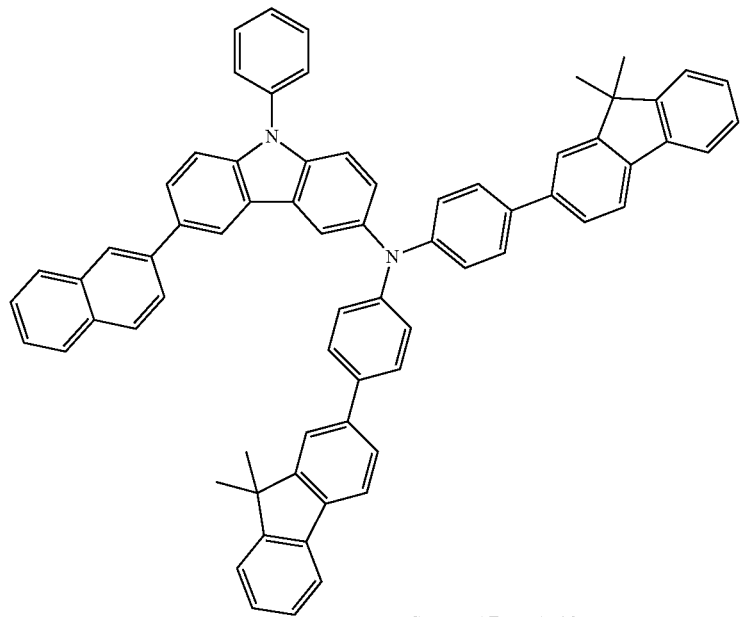
Structural Formula 46
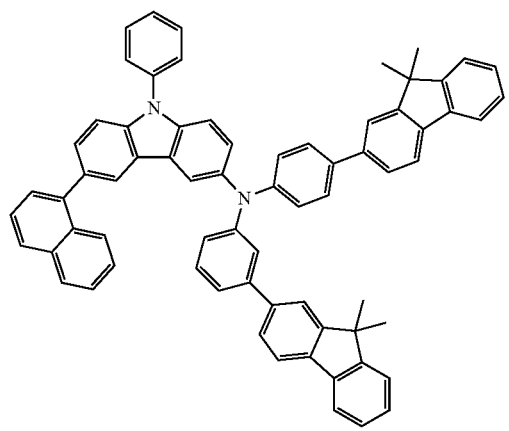
Structural Formula 47
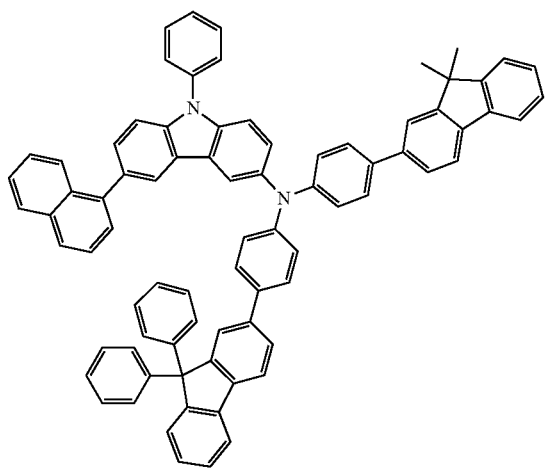

Structural Formula 48
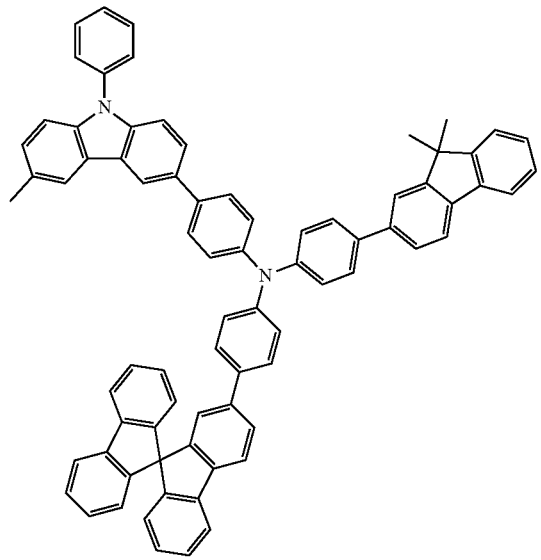
Structural Formula 49
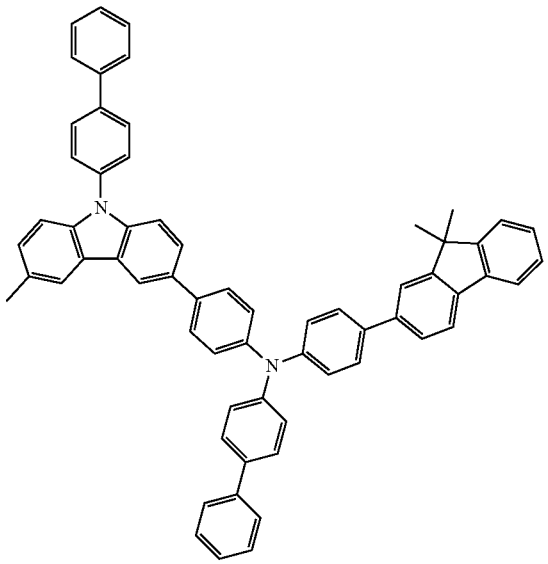
Structural Formula 50
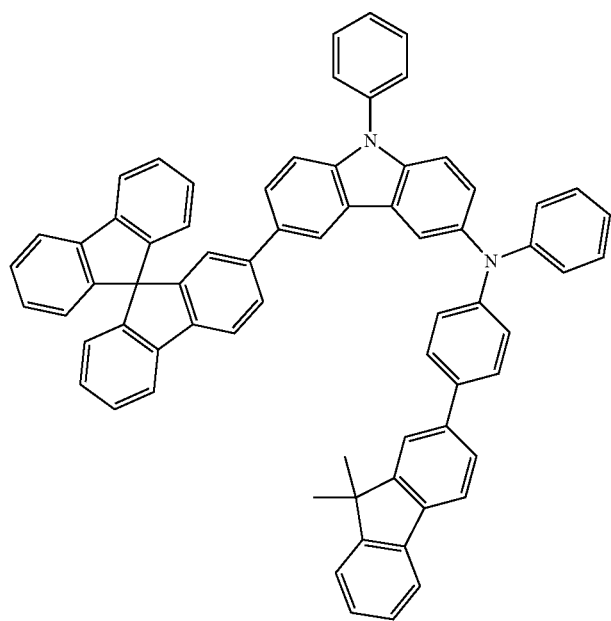

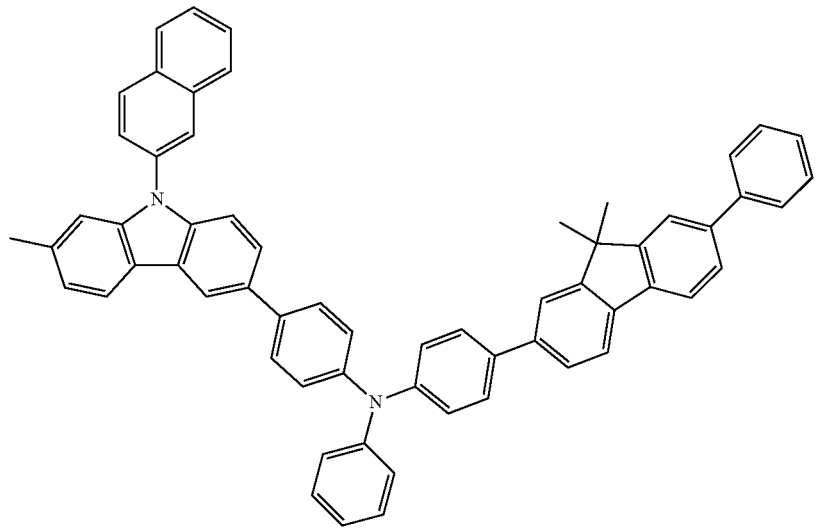
Structural Formula 51
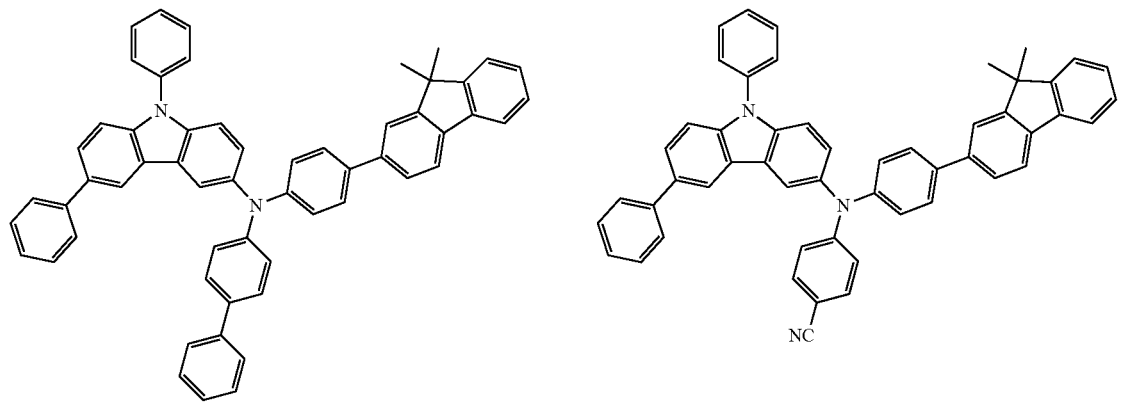
Structural Formula 52
Structural Formula 53
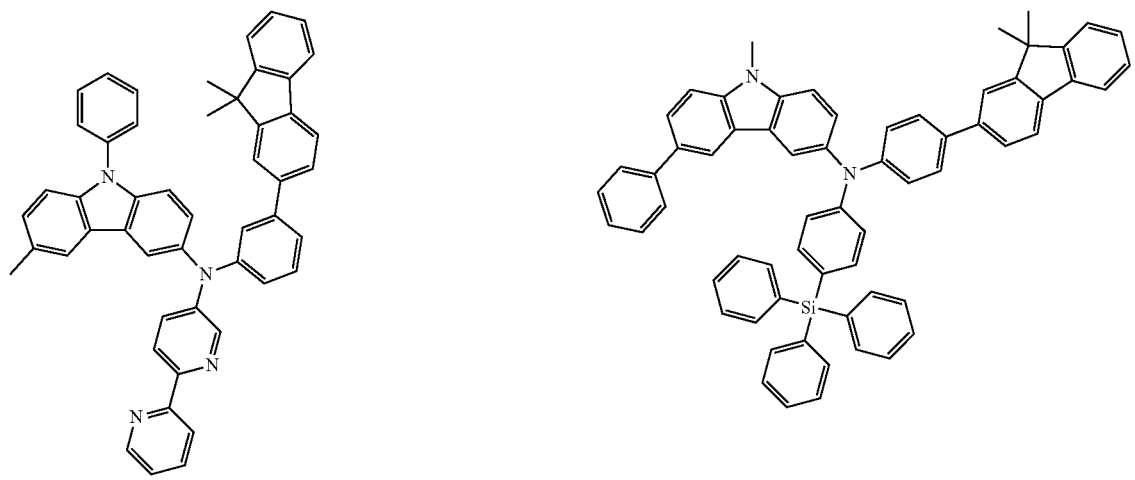
Structural Formula 54
Structural Formula 55

Structural Formula 56
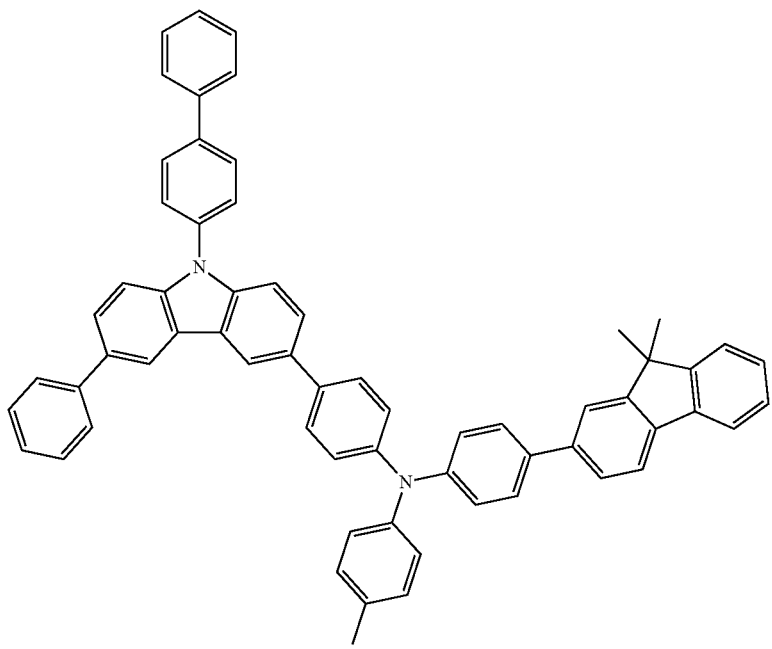
Structural Formula 57
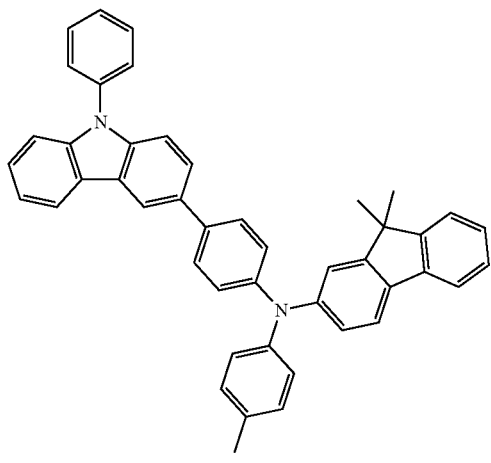
Structural Formula 58
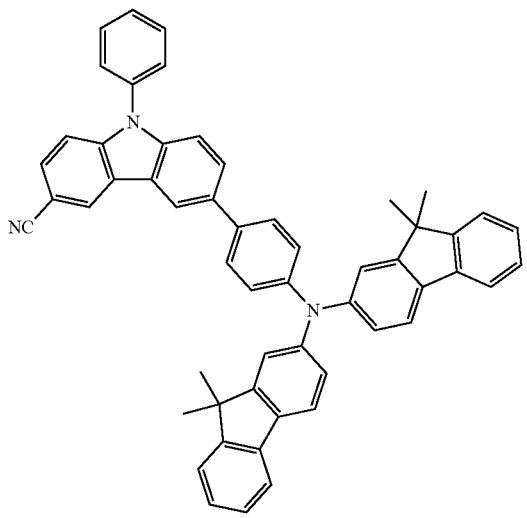

Structural Formula 59
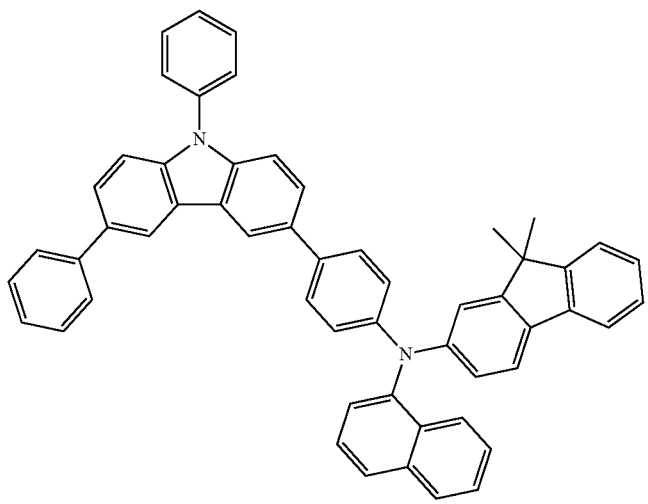
Structural Formula 60
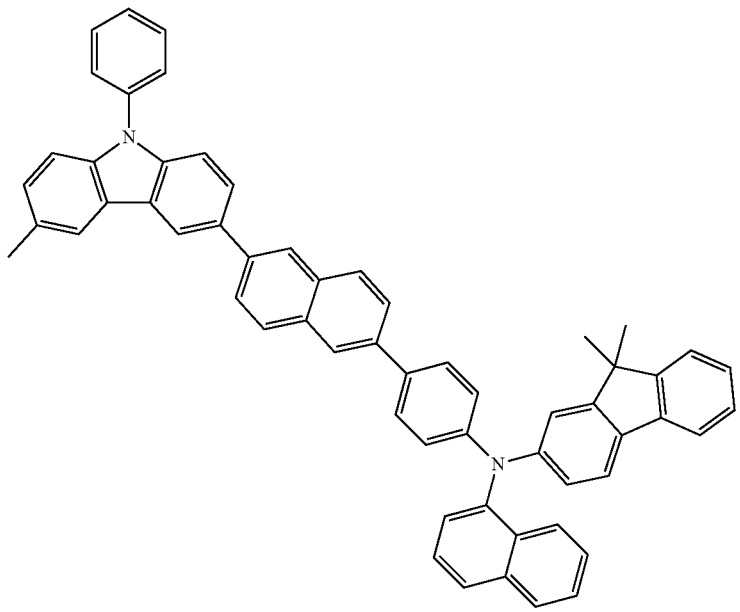
Structural Formula 61
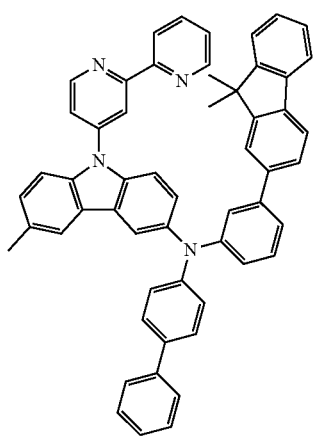
Structural Formula 62
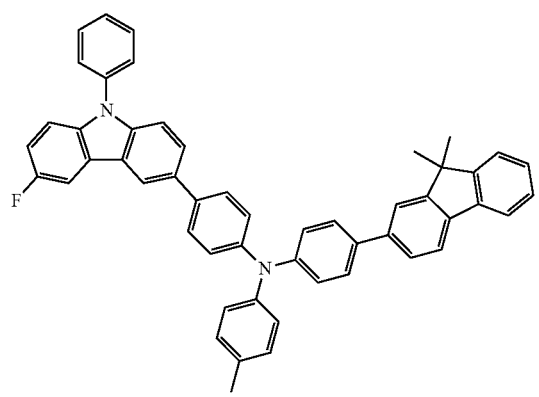

-continued
Structural Formula 63
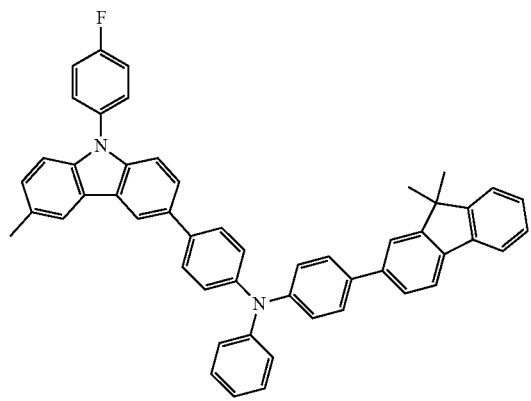
Structural Formula 64
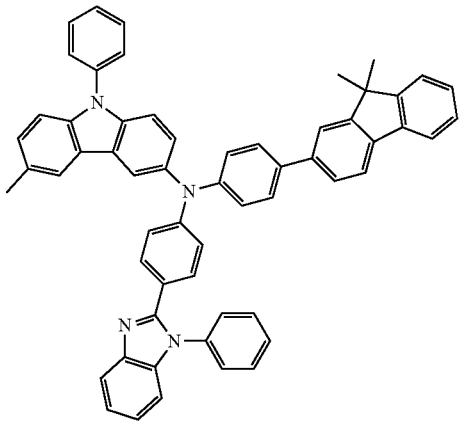
Structural Formula 65
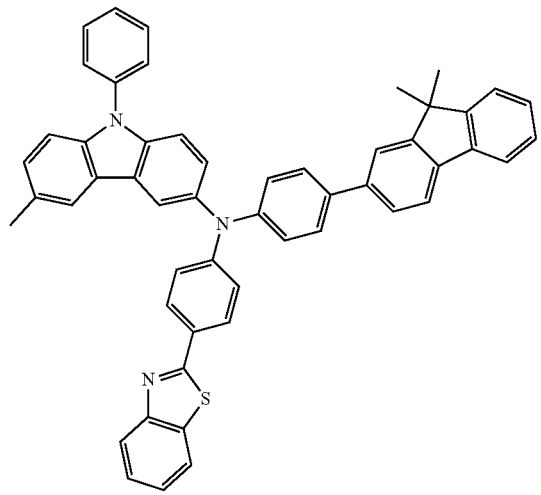
Structural Formula 66
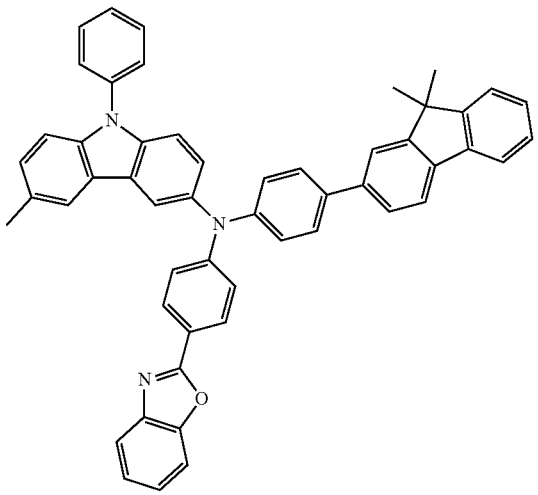
Structural Formula 67
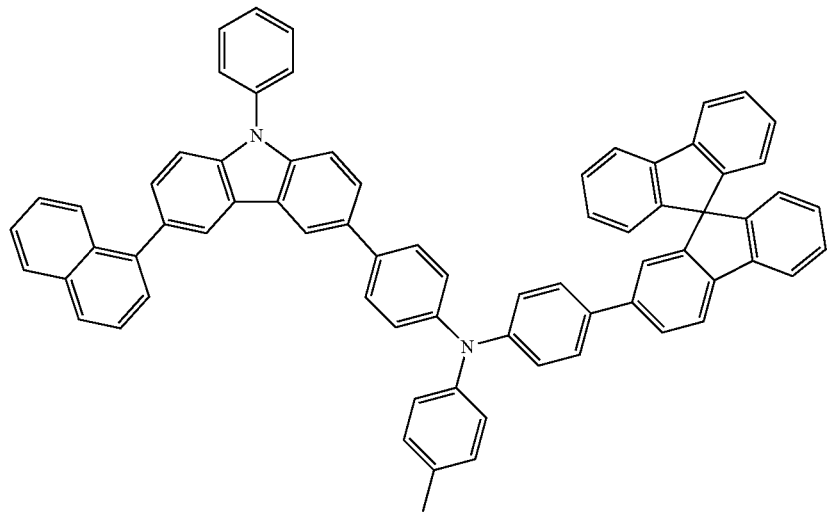

Structural Formula 68
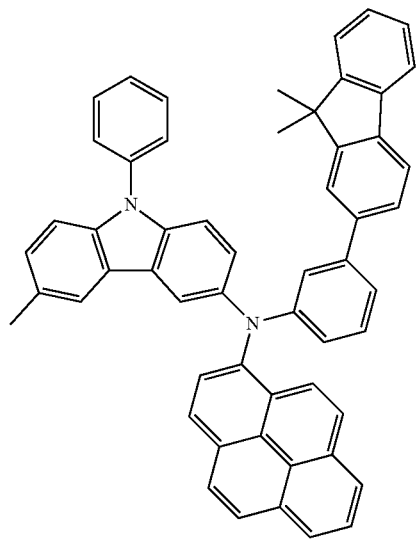
Structural 69
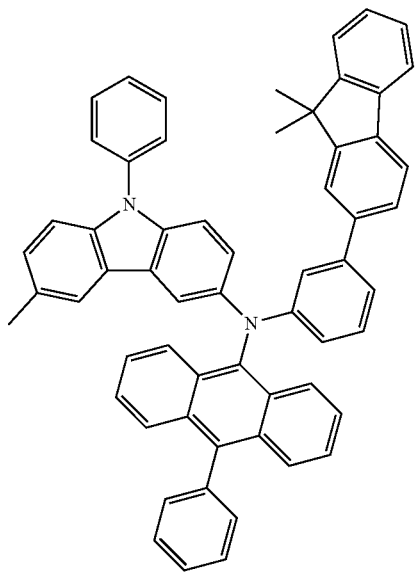
Structural Formula 70
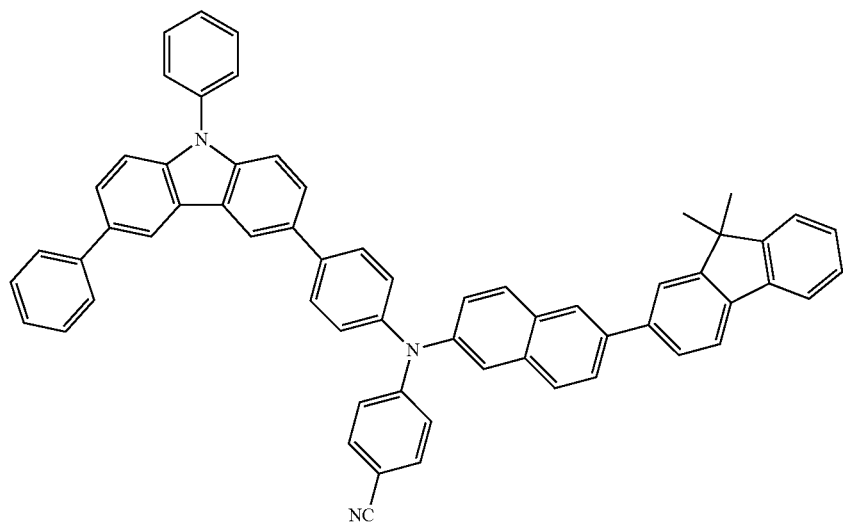
Structural Formula 71
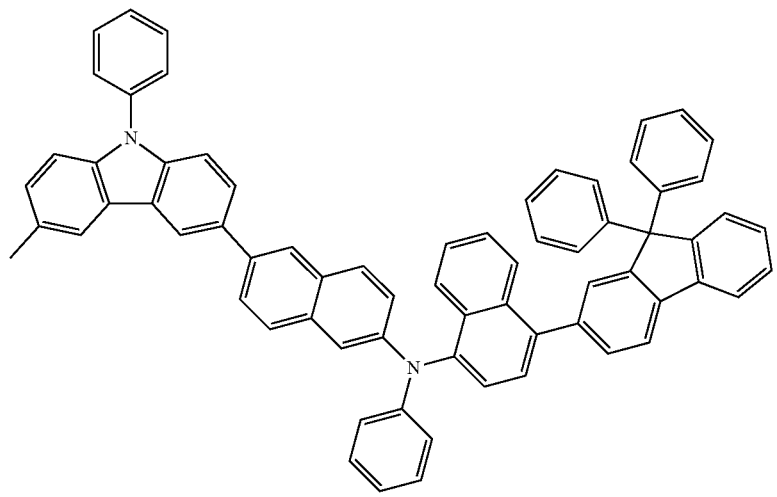

Structural Formula 72
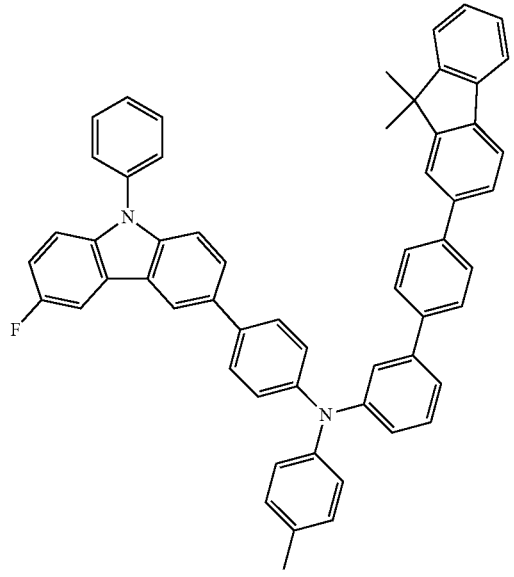
Structural Formula 73
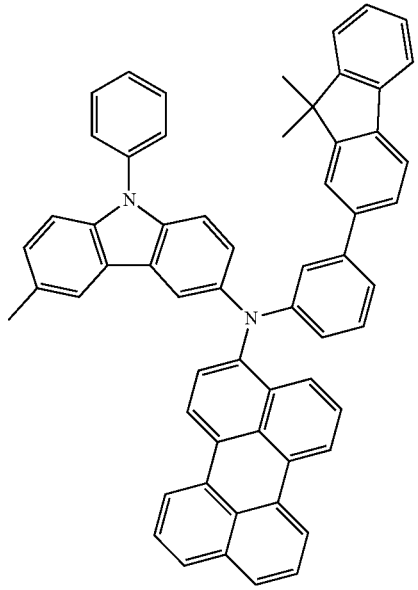
Structural Formula 74
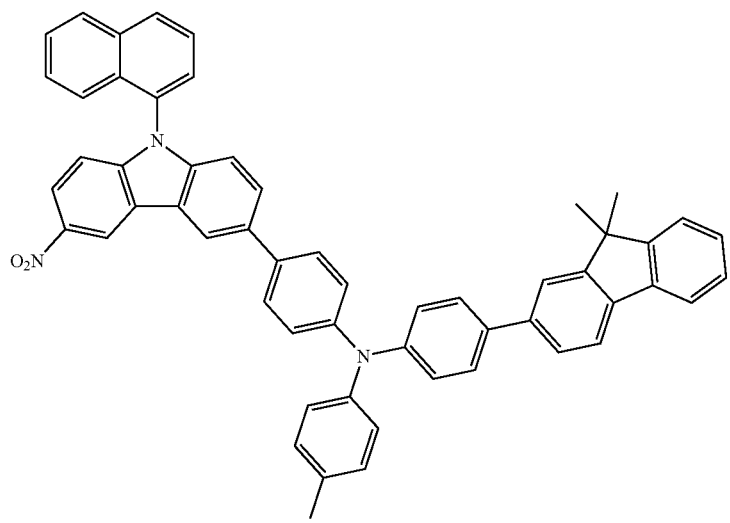

-continued
Structural Formula 75
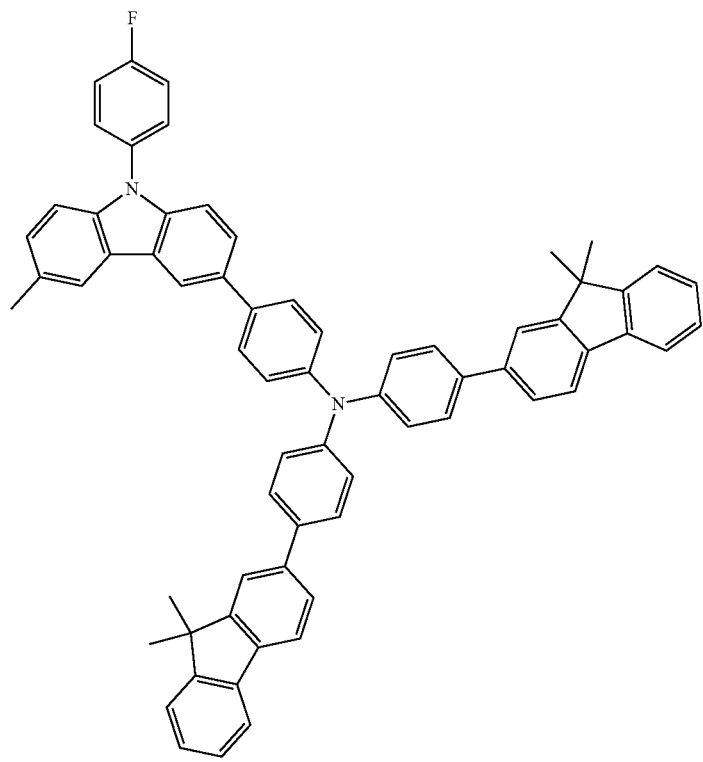
Structural Formula 76
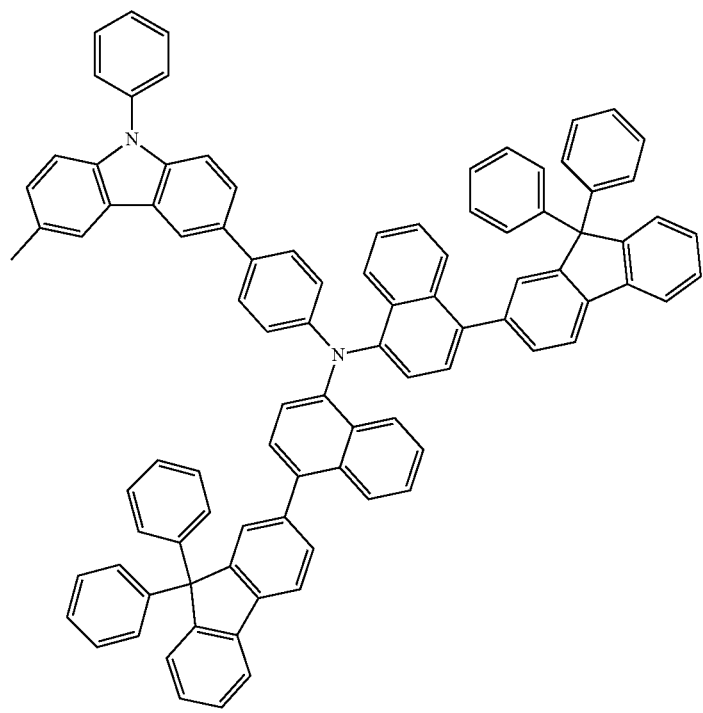

-continued
Structual Formula 77
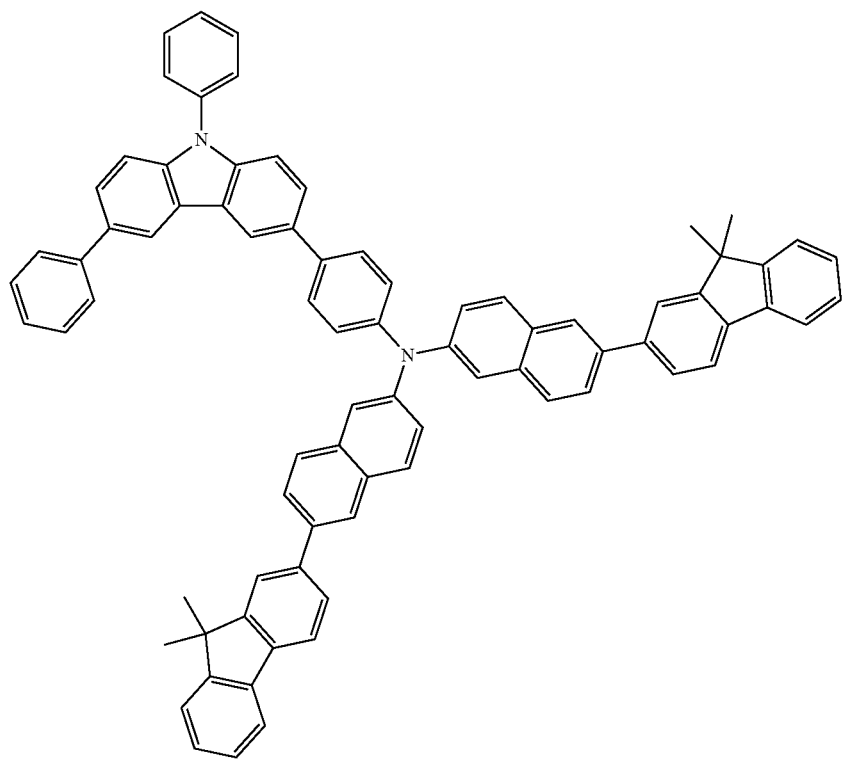
Structural Formula 78
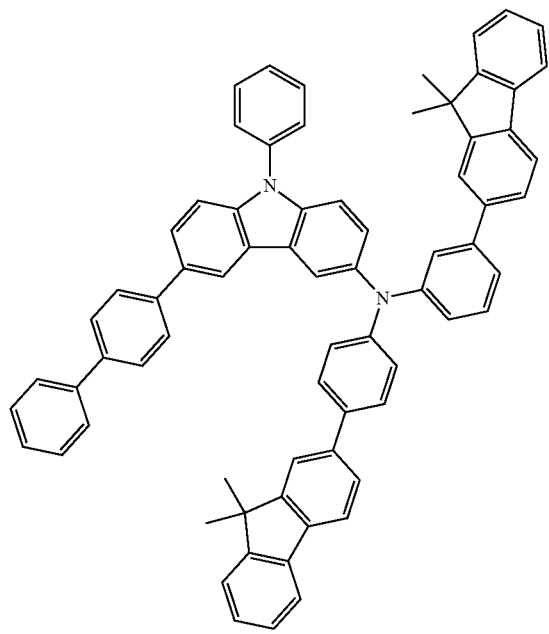

Structural Formula 79

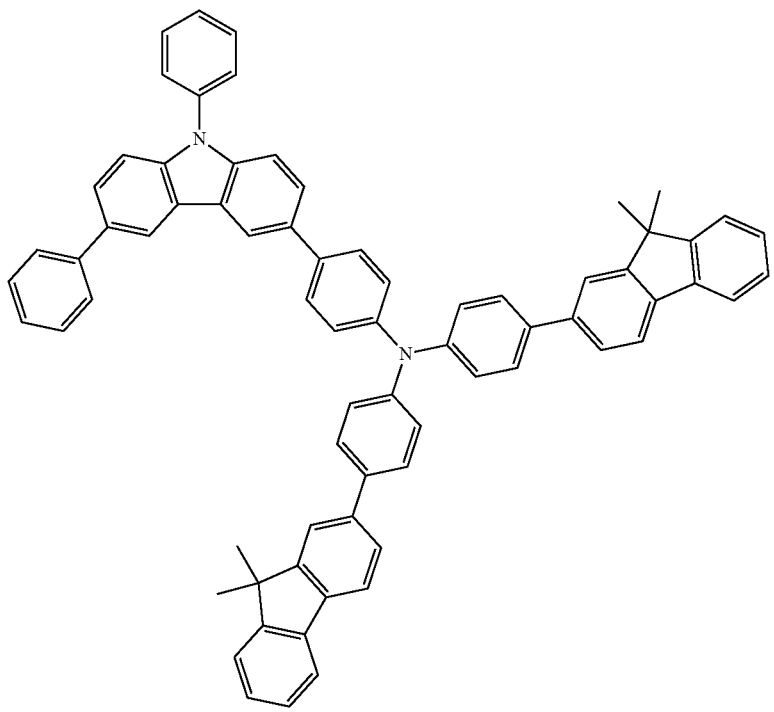

Structural Formula 80

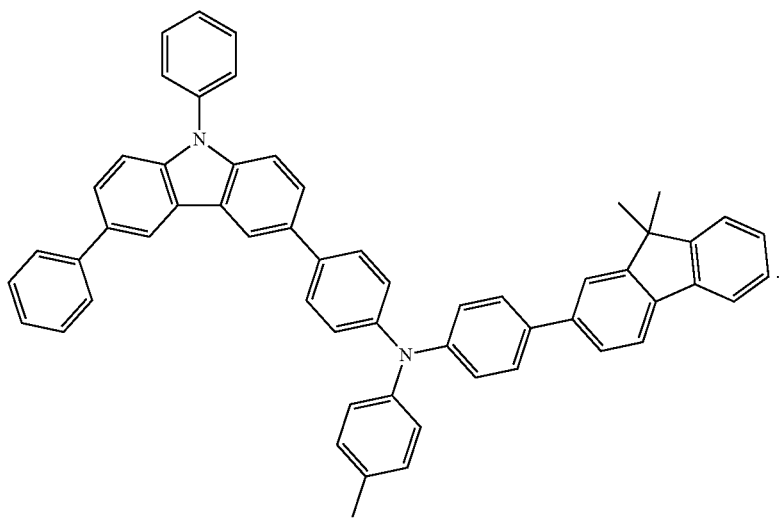

11. An organic electronic device which comprises a first electrode, a second electrode, and one or more organic material layers that are disposed between the first electrode and the second electrode, wherein one or more layers of the organic material layers comprise the compound according to claim 1.

12. The organic electronic device according to claim 11, wherein the organic material layer comprises at least one of a hole injection layer and a hole transport layer, and the hole injection layer or a hole transport layer comprises the compound represented by Formula 1.

13. The organic electronic device according to claim 11, wherein the organic material layer comprises a light emitting layer, and the light emitting layer comprises the compound of Formula 1.

14. The organic electronic device according to claim 11, wherein the organic electronic device is selected from the group consisting of an organic light emitting device, an organic phosphorescent device, an organic solar cell, an organic photoconductor (OPC), and an organic transistor.

15. An organic electronic device which comprises a first electrode, a second electrode, and one more organic material layers that are disposed between the first electrode and the second electrode, wherein one or more layers of the organic material layers comprise the compound according to claim 9.

16. An organic electronic device which comprises a first electrode, a second electrode, and one or more organic material layers that are disposed between the first electrode and the second electrode, wherein one or more layer of the organic material layers comprise the compound according to claim 10.

* * * * *